(12) United States Patent
Rezvani et al.

(10) Patent No.: US 12,310,988 B2
(45) Date of Patent: May 27, 2025

(54) BCMA CHIMERIC ANTIGEN RECEPTORS AND USES THEREOF

(71) Applicants: Board of Regents, The University of Texas System, Austin, TX (US); Takeda Pharmaceutical Company Limited, Osaka (JP)

(72) Inventors: Katy Rezvani, Houston, TX (US); Rafet Basar, Houston, TX (US); Paul Lin, Houston, TX (US); Michael David Curley, Cambridge, MA (US); LeeAnn Talarico, Cambridge, MA (US); Prashanth Vishwanath, Cambridge, MA (US); James Wilson Meador, III, Cambridge, MA (US)

(73) Assignees: Board of Regents, The University of Texas System, Austin, TX (US); Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 18/638,229

(22) Filed: Apr. 17, 2024

(65) Prior Publication Data
US 2024/0350543 A1    Oct. 24, 2024

Related U.S. Application Data

(60) Provisional application No. 63/496,823, filed on Apr. 18, 2023.

(51) Int. Cl.
| | | |
|---|---|---|
| *A61K 35/17* | (2025.01) |
| *A61K 9/00* | (2006.01) |
| *A61K 40/11* | (2025.01) |
| *A61K 40/15* | (2025.01) |
| *A61K 40/42* | (2025.01) |
| *A61P 35/00* | (2006.01) |
| *C07K 14/54* | (2006.01) |
| *C07K 14/705* | (2006.01) |
| *C07K 14/725* | (2006.01) |
| *C07K 16/28* | (2006.01) |
| *C07K 19/00* | (2006.01) |
| *C12N 15/62* | (2006.01) |
| *C12N 15/85* | (2006.01) |

(52) U.S. Cl.
CPC ............ *A61K 35/17* (2013.01); *A61K 9/0019* (2013.01); *A61K 40/11* (2025.01); *A61K 40/15* (2025.01); *A61K 40/4215* (2025.01); *A61P 35/00* (2018.01); *C07K 14/5443* (2013.01); *C07K 14/7051* (2013.01); *C07K 14/70521* (2013.01); *C07K 16/2878* (2013.01); *C12N 15/85* (2013.01); *A61K 2239/13* (2023.05); *A61K 2239/21* (2023.05); *A61K 2239/22* (2023.05); *C07K 2317/53* (2013.01); *C07K 2317/565* (2013.01); *C07K 2317/622* (2013.01); *C07K 2319/03* (2013.01); *C12N 15/62* (2013.01)

(58) Field of Classification Search
CPC .......................... A61K 35/17; A61K 39/4611; A61K 39/4613; A61K 2239/21; A61K 2239/22; C07K 2317/53; C07K 2317/565; C07K 2317/622
See application file for complete search history.

(56) References Cited

U.S. PATENT DOCUMENTS

| | | | |
|---|---|---|---|
| 2017/0283500 A1* | 10/2017 | Wiltzius | ................... A61P 11/06 |
| 2018/0002397 A1* | 1/2018 | Shah | .................. A61K 39/4613 |
| 2024/0180968 A1* | 6/2024 | Gavin | .................. C12N 5/0646 |

FOREIGN PATENT DOCUMENTS

| | | | | |
|---|---|---|---|---|
| WO | WO-2021055349 A1 * | 3/2021 | ........... A61K 31/519 |
| WO | 2022/060806 A1 | 3/2022 | |
| WO | 2023/280307 A1 | 1/2023 | |
| WO | 2023/288185 A2 | 1/2023 | |
| WO | WO-2023068382 A2 * | 4/2023 | ......... A61K 39/4613 |

OTHER PUBLICATIONS

Almagro et al., Frontiers in Immunology, 2018, 8: 1751, pp. 1-19.*
Murphy et al., Journal of Immunological Methods, 2018, 463: 127-133.*
Herold et al. (Science Reports, 2017, 7(1):12276, pp. 1-17.*
Leninger et al., Inducing conformational preference of the membrane protein transporter EmrE through conservative mutations. Elife. Oct. 22, 2019;8:e48909, pp. 1-16.*
"International Search Report" for International Application No. PCT/IB2024/053759 dated Jul. 5, 2024 (5 pages).
Duong, et al., "Engineering T Cell Function using Chimeric Antigen Receptors Identified Using a DNA Library Approach", PLOS One, vol. 8, No. 5, XP055664591 DOI: 10.1371/journal.pone.0063037, May 7, 2013, p. e63037.
He, et al., "The Implementation of TNFRSF Co-Stimulatory Domains in CAR-T Cells for Optimal Functional Activity", Cancers, vol. 14, No. 2, p. 299XP093118067, CH, ISSN: 2072-6694, DOI: 10.3390/cancers14020299, 2022.
Kulemzin et al., "Engineering Chimeric Antigen Receptors", Acta Naturae, pp. 6-14XP055552237, DOI: 10.32607/20758251-2017-9-1-6-14 Retrieved from the Internet: URL:https://www.ncbi.nlm.nih.gov/pmc/articles/PCT5406655/pdf/AN20758251-09-01-006.pdf, Jan. 1, 2017.

* cited by examiner

Primary Examiner — Hong Sang
(74) *Attorney, Agent, or Firm* — Proskauer Rose LLP

(57) ABSTRACT

The present application provides BCMA targeting chimeric antigen receptor (CAR) comprising a BCMA binding region and an intracellular costimulatory domain derived from DAP10. Further provided are engineered immune effector cells (such as NK cells) comprising the chimeric antigen receptors. Pharmaceutical compositions, kits and methods of treating cancer are also provided.

3 Claims, 16 Drawing Sheets

Specification includes a Sequence Listing.

BCMA CHIMERIC ANTIGEN RECEPTORS AND USES THEREOF

CROSS REFERENCED APPLICATIONS

This application claims priority to, and the benefit of U.S. Provisional Patent Application Ser. No. 63/496,823 filed on Apr. 18, 2023; the contents of which are incorporated herein by reference in its entirety.

REFERENCE TO SEQUENCE LISTING

The instant application contains a sequence listing which has been submitted electronically in XML format and is hereby incorporated by reference in its entirety. The sequence listing file entitled MIL-021US1_SL. XML, was created on Oct. 4, 2024, which is 75 kilobytes in size.

FIELD OF THE INVENTION

The present invention provides BCMA targeting chimeric antigen receptors comprising a DAP10 costimulatory domain which have a high efficacy in killing tumor cells. Provided herein also include compositions, cells and methods for treating diseases associated with expression of BCMA (e.g., cancer).

BACKGROUND

BCMA is a B-cell maturation antigen. BCMA (also known as TNFRSF17, BCM or CD269) is a member of the tumor necrosis receptor (TNFR) family and is predominantly expressed on terminally differentiated B cells, e.g., memory B cells, and plasma cells. BCMA protein is universally detected in multiple myeloma (MM) cells and in other lymphomas including non-Hodgkin's lymphoma (NHL). Patients having B cell malignancies, including non-Hodgkin's lymphoma (NHL) and multiple myeloma (MM), are significant contributors to cancer mortality.

The response of B cell malignancies to various forms of treatment is mixed. Traditional methods of treating B cell malignancies, including chemotherapy and radiotherapy, have limited utility due to toxic side effects. Immunotherapy with anti-CD19, anti-CD20, anti-CD22, anti-CD23, anti-CD52, anti-CD80, and anti-HLA-DR therapeutic antibodies have provided limited success, due in part to poor pharmacokinetic profiles, rapid elimination of antibodies by serum proteases and filtration at the glomerulus, and limited penetration into the tumor site and expression levels of the target antigen on cancer cells.

Attempts to use anti-BCMA antibody therapy and genetically modified cells expressing BCMA targeting chimeric antigen receptors (CARs) have made progression for immunotherapy of B cell malignancies.

SUMMARY OF THE INVENTION

The present invention in general relates to improved BCMA targeting CAR polypeptides and, among other things, compositions and cells comprising the improved BCMA-CAR polypeptides, and methods of use thereof for treatment of B cell associated diseases and disorders. The BCMA targeting CAR polypeptide comprises a DAP10 costimulatory domain; the BCMA-DAP10 CAR polypeptide can increase expansion and therapeutic efficacy of immune effector cells (e.g., NK cells and T cells) genetically engineered to express BCMA targeting CAR polypeptides. In particular, NK cells that express the present BCMA targeting CAR polypeptides have higher efficacy in killing tumor cells in various tumors. In the present disclosure, the nucleic acid sequence encoding a BCMA targeting CAR polypeptide comprising a DAP10 co-stimulatory domain is codon optimized.

In one aspect, the present invention provides a chimeric antigen receptor (CAR) polypeptide comprising an antigen binding region that specifically binds to B-cell maturation antigen (BCMA), a hinge domain, a transmembrane domain, a DAP10 costimulatory domain, and at least one intracellular signaling domain. A polynucleotide encoding a chimeric antigen receptor polypeptide is also included.

In some embodiments, the BCMA binding domain of the CAR polypeptide is anti-BCMA antibody, an antigen binding domain thereof, a Fab fragment, a F(ab')2 fragment, a Fv fragment, a single chain variable fragment (scFv), a single domain antibody, or a nanobody.

In some embodiments, the BCMA binding region binds to BCMA with a $K_D$ of less than about $1\times10^{-6}$ M, less than about $1\times10^{-7}$ M, less than about $1\times10^{-8}$ M, or less than about $1\times10^{-9}$ M, or less than about $1\times10^{-10}$ M.

In some embodiments, the BCMA binding region comprises a heavy chain variable region complementarity determining region (HCDR) 1 comprising SYAIH (SEQ ID NO: 2), a HCDR2 comprising VTWHDGSNKYYAESVMG (SEQ ID NO: 3), and a HCDR3 comprising AKFGEPQYFQH (SEQ ID NO: 4).

In some embodiments, the BCMA binding region comprises a light chain variable region complementarity determining region (LCDR) 1 comprising RASQGINNYLA (SEQ ID NO: 6), a LCDR2 comprising AASTLQS (SEQ ID NO: 7), and a LCDR3 comprising QQLKSYPFT (SEQ ID NO: 8).

In some embodiments, the BCMA binding region comprises a heavy chain variable region (VH) that comprises three complementarity determining regions: HCDR1 comprising SYAIH (SEQ ID NO: 2), HCDR2 comprising VTWHDGSNKYYAESVMG (SEQ ID NO: 3), and HCDR3 comprising AKFGEPQYFQH (SEQ ID NO: 4), and a light chain variable region (VL) that comprises three complementarity determining regions: LCDR1 comprising RASQGINNYLA (SEQ ID NO: 6), LCDR2 comprising AASTLQS (SEQ ID NO: 7), and LCDR3 comprising QQLKSYPFT (SEQ ID NO: 8).

In some embodiments, the BCMA binding region comprises a heavy chain variable region (VH) comprising an amino acid sequence represented by SEQ ID NO: 1, or an amino acid sequence that is at least about 75%, 80%, 85%, 90%, 95%, 96%, 97%, 97%, 98%, or 99% identical to SEQ ID NO: 1.

In some embodiments, the BCMA binding region comprises a light chain variable region (VL) comprising an amino acid sequence represented by SEQ ID NO: 5, or an amino acid sequence that is at least about 75%, 80%, 85%, 90%, 95%, 96%, 97%, 97%, 98%, or 99% identical to SEQ ID NO: 5.

In some embodiments, the BCMA binding region comprises a heavy chain variable region (VH) comprising the amino acid sequence of SEQ ID NO: 1 and a light chain variable region (VL) comprising the amino acid sequence of SEQ ID NO: 5.

In one preferred embodiment, the BCMA binding region is a single chain variable fragment (scFv). One exemplary scFv that can bind to BCMA comprises the sequence of SEQ ID NO: 20. The BCMA binding domain may also comprise an amino acid sequence at least about 75%, at least about 80%, at least about 85%, at least about 90%, at least about 95%, at least about 96%, at least about 97%, at least about 98%, or at least about 99% identical to SEQ ID NO: 20.

In some embodiments, the BCMA binding domain is encoded by a nucleic acid sequence of SEQ ID NO: 35, or SEQ ID NO: 51.

In accordance with the present invention, the BCMA targeting CAR polypeptide comprises an intracellular DAP10 costimulatory domain. In some embodiments, the DAP10 co-stimulatory domain comprises the amino acid sequence of SEQ ID NO: 24, or an amino acid sequence at least about 75%, at least about 80%, at least about 85%, at least about 90%, at least about 95%, at least about 96%, at least about 97%, at least about 98%, or at least about 99% identical to SEQ ID NO. 24. In some embodiments, the DAP10 co-stimulatory domain is encoded by a nucleic acid sequence comprising the sequence of SEQ ID NO: 39, or SEQ ID NO: 57.

In some embodiments, the BCMA targeting CAR comprises one or more additional intracellular costimulatory domain.

In accordance with the present invention, the BCMA targeting CAR polypeptide comprises an intracellular signaling domain. In some embodiments, the intracellular signaling domain is a CD3ζ signaling domain. The intracellular CD33 signaling domain comprises the amino acid sequence of SEQ ID NO: 23, or an amino acid sequence at least about 75%, at least about 80%, at least about 85%, at least about 90%, at least about 95%, at least about 96%, at least about 97%, at least about 98%, or at least about 99% identical to SEQ ID NO: 23. In some embodiments, the CD35 signaling domain is encoded by a nucleic acid sequence comprising the sequence of SEQ ID NO: 40, or SEQ ID NO: 58.

In some embodiments, the present BCMA targeting CAR polypeptide may comprise one or more additional costimulatory domains and/or, one or more signaling domains. In some aspects, the costimulatory domains are derived from OX-40, 4-1BB/CD137, CD2, CD7, CD27, CD28, CD30, CD40, programmed death-1 (PD-1), inducible T cell costimulator (ICOS), CDS gamma, CD3 delta, CD3 epsilon, CD247, CD276 (B7-H3), LIGHT (tumor necrosis factor superfamily member 14; TNFSF1.4), NKG2C, 2B4, Ig alpha (CD79a), DAP12, Fc gamma receptor, MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD 19, CD4, CDSalpha, CDSbeta, 11.2 beta, IL2R gamma, IL7R alpha, ITGA4, VLA1, CD49a, ITGA4, IA4, CD49D, ITGA6, VLA-6, CD49f, ITGAD, ITGAE, CD103, ITGAL, LFA-1, ITGAM, ITGAX, ITGB1, CD29, ITGB2, ICOS, CD18, LFA-1, ITGB7, NKG2D, TNFR2, TRANCE RANKL, DNAM1 (CD226), SLAMF4 (CD244, 2B4), CD84, CD96 (Tactile), CEACAM1, CRT AM, Ly9 (CD229), CD160 (BY55), PSGL1, CDIOO (SEMA4D), CD69, SLAMF6 (NTB-A, Ly108), BLAME (SLAMF8), SELPLG (CD 162), LTBR, LAT, GADS, SLP-76, PAG/Cbp, CD 19a, a ligand that specifically binds with CD83, or any combination thereof. In some aspects, the signaling domains are derived from CD28, CD137 (4-IBB), CD134 (OX40), FcR γ, FcR β, FcεRI, CD3 zeta, CD3 epsilon, CD3 gamma, CD3 delta, CD27, CD2, CD5, CD22, CD79a, CD79b, CD66d, CD278 (ICOS), ICAM-1, LFA-1 (CD1 la/CD18), Lck, TNFR-I, TNFR-II, Fas, CD30, CD40 DAP10, DAP12, or combinations thereof.

In accordance with the present invention, the BCMA targeting CAR polypeptide comprises a hinge domain and a transmembrane domain that link the extracellular BCMA binding region and the cytoplasmic region of the CAR (i.e., the costimulatory domain and signaling domain).

In some embodiments, the hinge domain is selected from hinge domains and/or extracellular domains of IgG, CD8a, CD4 and CD28. In some examples, the hinge domain is a CD28 hinge domain; the CD28 hinge domain comprises the amino acid sequence of SEQ ID NO: 21, or an amino acid sequence at least about 75%, at least about 80%, at least about 85%, at least about 90%, at least about 95%, at least about 96%, at least about 97%, at least about 98%, or at least about 99% identical to SEQ ID NO: 21.

In some embodiments, the CD28 hinge domain is encoded by a nucleic acid sequence comprising the sequence of SEQ ID NO: 37, or SEQ ID NO: 54.

In some embodiments, the transmembrane domain is a transmembrane domain derived from CD8, CD 16, CD27, CD28, NKG2D, NKp44, NKp46, NKp30, NKp80, DNAM-1, CD3 zeta, CD3 epsilon, CD3 gamma, CD3 delta, CD45, CD4, CD5, CD9, CD22, CD33, CD37, CD64, CD80, CD86, CD134, CD137, CD154, ICOS/CD278, GITR/CD357, DAP10, DAP12, or variant thereof. In some examples, the transmembrane domain is a CD28 transmembrane domain; the CD28 transmembrane domain comprises the amino acid sequence of SEQ ID NO: 22, or an amino acid sequence at least about 75%, at least about 80%, at least about 85%, at least about 90%, at least about 95%, at least about 96%, at least about 97%, at least about 98%, or at least about 99% identical to SEQ ID NO: 22.

In some embodiments, the CD28 transmembrane domain is encoded by a nucleic acid sequence comprising the sequence of SEQ ID NO: 38, or SEQ ID NO: 56.

In some embodiments, the BCMA targeting CAR polypeptide further comprises one or more additional polypeptides. In some examples, the polypeptide is a cytokine such as IL-15. As a non-limiting example, the BCMA targeting CAR polypeptide further comprises an IL-15 having the amino acid sequence of SEQ ID NO: 26. In some embodiments, the IL-15 is encoded by a nucleic acid sequence comprising the sequence of SEQ ID NO: 52, or SEQ ID NO: 53.

In some embodiments, the BCMA targeting CAR polypeptide of the present invention comprises a signal peptide and one or more linker sequences such as a cleavable 2A peptide (e.g., E2A). For example, the E2A peptide may locate between the CAR polypeptide and IL-15 as shown in FIG. 1. The E2A peptide, in one example, comprises the amino acid sequence of SEQ ID NO: 27. An exemplary signal peptide sequence is presented by SEQ ID NO: 28, or SEQ ID NO: 59.

An exemplary BCMA targeting CAR polypeptide of the present invention comprises the amino acid sequence of SEQ ID NO: 29. In some examples, the BCMA targeting CAR polypeptide comprises an amino acid sequence at least about 75%, at least about 80%, at least about 85%, at least about 90%, at least about 95%, at least about 96%, at least about 7, at least about 98%, or at least about 99% identical to SEQ ID NO: 29.

In another aspect of the present invention, a polynucleotide encoding a BCMA targeting CAR polypeptide contemplated herein is provided. The polynucleotide is mRNA or DNA. In some embodiments, the polynucleotide is codon optimized. In some embodiments, the polynucleotide comprises at least one modified nucleotide. In other embodiments, the polynucleotide comprises unmodified nucleotides.

An exemplary polynucleotide encoding the BCMA targeting CAR polypeptide comprises the nucleotide sequence of SEQ ID NO: 44. In some aspects, the polynucleotide comprises a nucleotide sequence at least about 75%, at least about 80%, at least about 85%, at least about 90%, at least about 95%, at least about 96%, at least about 97%, at least about 98%, at least 99%, or 100% identical to SEQ ID NO: 44.

In one embodiment, the polynucleotide encoding the BCMA targeting CAR polypeptide comprises the nucleotide sequence of SEQ ID NO: 60. In some aspects, the polynucleotide comprises a nucleotide sequence at least about 75%, at least about 80%, at least about 85%, at least about 90%, at least about 95%, at least about 96%, at least about 97%, at least about 98%, at least 99%, or 100% identical to SEQ ID NO: 60.

Another exemplary BCMA targeting CAR polypeptide of the present invention comprises the amino acid sequence of SEQ ID NO: 13. In some examples, the BCMA targeting CAR polypeptide comprises an amino acid sequence at least about 75%, at least about 80%, at least about 85%, at least about 90%, at least about 95%, at least about 96%, at least about 7, at least about 98%, or at least about 99% identical to SEQ ID NO: 13.

In one embodiment, the polynucleotide encoding the BCMA targeting CAR (e.g., signal sequence 1-BCMA binder-linker-CD28 (hinge)-linker-CD28 (TM)-DAP10 (costim)-CD3z-E2A-Signal sequence 2-sIL15) comprises the nucleotide sequence of SEQ ID NO: 25. In some aspects, the polynucleotide comprises a nucleotide sequence at least about 75%, at least about 80%, at least about 85%, at least about 90%, at least about 95%, at least about 96%, at least about 97%, at least about 98%, at least 99%, or 100% identical to SEQ ID NO: 25.

In one embodiment, the polynucleotide encoding the BCMA targeting CAR comprises a codon optimized sequence of SEQ ID NO: 55. In some aspects, the polynucleotide comprises a nucleotide sequence at least about 75%, at least about 80%, at least about 85%, at least about 90%, at least about 95%, at least about 96%, at least about 97%, at least about 98%, at least 99%, or 100% identical to SEQ ID NO: 55.

In some embodiments, a vector comprises any polynucleotide encoding the BCMA targeting CAR of the present invention is provided. The vector may be a non-viral vector such as plasmid, or a viral vector such as an adenoviral vector, an adenovirus associated viral (AAV) vector, a lentiviral vector, and a retroviral vector. As non-limiting examples, the vector may comprise a polynucleotide having the nucleic acid sequence selected from the group consisting of SEQ ID NOs: 25, 44, 55 and 60.

In another aspect, the present invention provides immune effector cells that are genetically engineered to express at least one BCMA targeting CAR polypeptide described herein. The immune effector cell includes but is not limited to natural killer (NK) cell, natural killer T (NKT) cell, T cell, B cell, macrophage, mesenchymal stromal cell, dendritic cell, tumor-infiltrating lymphocyte (TIL), cytotoxic T lymphocyte (CTL), or any combination thereof.

In some embodiments, the immune effector cell is T cell, such as mature T cell, T helper cell, tumor infiltrating T cell, autologous T cell, engineered autologous T cell (eACT), allogeneic T cell, or any combination thereof.

In some embodiments, the immune effector cell is NK cell derived from cord blood, peripheral blood, induced pluripotent stem cells, hematopoietic stem cells, bone marrow, from a cell line, or a mixture thereof.

In some embodiments, the immune effector cells are engineered to express the BCMA targeting CAR for immunotherapy, e.g., cancer treatment. In some embodiments, the immune cells are autologous, allogeneic, or a mixture thereof.

Accordingly, pharmaceutical compositions comprising the BCMA targeting CAR polypeptides, polynucleotides encoding the BCMA targeting CAR and immune effector cells engineered to express the BCMA targeting CAR polypeptide are provided. The compositions may be formulated for cell-based therapy.

In another aspect of the present invention, methods for treating cancer in a subject in need using the BCMA targeting CARs, compositions and cells expressing the BCMA targeting CAR contemplated herein are provided. The BCMA targeting CARs, compositions and cells expressing the BCMA targeting CAR of the present invention can be used to induce an immune response against a disorder or disease associated with BCMA expression in a subject.

In some embodiments, the immune effector cells of the invention are administered at an amount from about $1\times10^6$ to $10\times10^8$, or about $5\times10^6$ to about $9.5\times10^8$, or about $1\times10^7$ to $9\times10^8$, or about $5\times10^7$ to $8.5\times10^8$, or about $1\times10^8$ to $8.0\times10^8$, or about $2.0\times10^8$ to $8.0\times10^8$, or about $1.0\times10^8$ to $2.0\times10^9$.

In some embodiments, the cells are administered at an amount of $1.0\times10^8$.

In some embodiments, the cells are administered at an amount of $5.0\times10^8$.

In some embodiments, the cells are administered at an amount of $1.5\times10^9$.

In some embodiment, the BCMA targeting CARs, composition and/or engineered immune cells are administered by infusion, injection, intravenously, intraarterially, intraperitoneally, intratracheally, intratumorally, intramuscularly, endoscopically, intralesionally, intracranially, percutaneously, subcutaneously, regionally, by perfusion, or any combination thereof.

In some embodiments, BCMA targeting CARs, composition and/or engineered immune cells are administered intravenously.

In some embodiments, the BCMA targeting CARs, composition and/or engineered immune cells may be used alone for treating a cancer or in combination with one or more other cancer therapies including chemotherapy, radiation, immunotherapy, cancer vaccine, and/or targeted therapy.

In some embodiments, the subject receives immunodepleting chemotherapy.

In some embodiments, the method of the present invention may be used to treat B cell malignancy, multiple myeloma (e.g., relapsed and refractory multiple myeloma), lymphoma, and/or leukemia.

DETAILED DESCRIPTION

Figure 1:
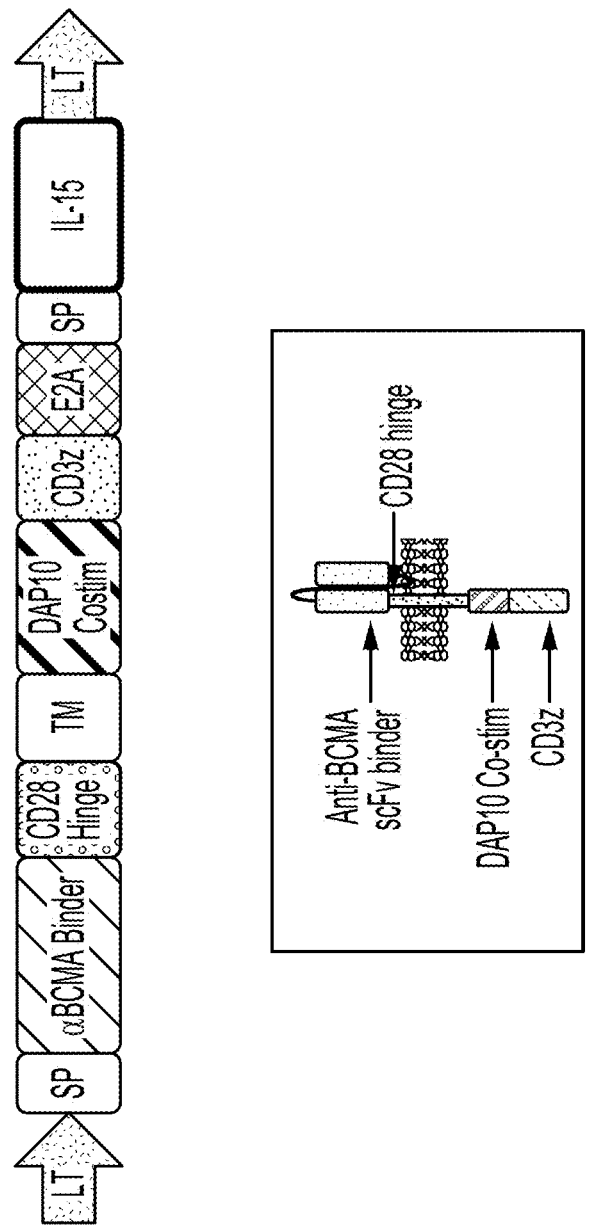
FIG. 1 is an exemplary diagram of the BCMA-DAP10-CAR construct.

The present invention provides, among other things, chimeric antigen receptor (CAR) targeting B-cell maturation antigen (BCMA), compositions and cells expressing BCMA targeting CAR, and methods of use thereof for the treatment of a disease such as cancer. The present BCMA targeting CAR construct incorporates a DAP10 derived costimulatory signaling domain which increases expansion in vivo and functionality of immune effector cells that express the BCMA-DAP10 CAR (e.g., NK cells). The present BCMA-DAP10 CAR polypeptides demonstrate a higher efficacy in killing tumor cells and inhibiting tumor growth. In some embodiments, the BCMA-DAP10 CAR of the present invention further comprises IL-15, which is cleavable from the CAR polypeptide. The polynucleotide encoding a BCMA-DAP10 CAR polypeptide may be codon optimized.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +20% or +10%, more preferably +5%, even more preferably +1%, and still more preferably +0.0.1% from the specified value, as such variations are appropriate to perform the disclosed methods.

Antigen binding domain: as used herein, the term "antigen binding domain" refers to one or more extracellular domains of the chimeric antigen receptor which have specificity for a particular antigen, e.g., BCMA.

Antibody: as used herein, the term "antibody," refers to an immunoglobulin molecule which specifically binds with an antigen. For example, in one aspect, the antigen is B7-H6. In another aspect, the antigen is MICA. Antibodies can be intact immunoglobulins derived from natural sources or from recombinant sources and can be immunoreactive portions of intact immunoglobulins. The term is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, single chain antibody fragments, including single chain variable fragments (scFv), diabodies, and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific (e.g., bispecific) antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. Kappa and lambda light chains refer to the two major antibody light chain isotypes.

The term "antibody fragment" refers to a portion of an intact antibody and refers to the antigenic determining variable regions of an intact antibody. Examples of antibody fragments include, but are not limited to, fragment antigen binding (Fab) fragments, F(ab')$_2$ fragments, Fab' fragments, Fv fragments, recombinant IgG (rIgG) fragments, single chain antibody fragments, including single chain variable fragments (scFv), single domain antibodies (e.g., sdAb, sdFv, nanobody) fragments, diabodies, and multispecific antibodies formed from antibody fragments. In a specific embodiment, the antibody fragment may be an scFv.

Chimeric antigen receptor (CAR): As used herein, the term "chimeric antigen receptor" or "CAR" means a protein that when expressed on the surface of a cell allows a CAR expressing cell to recognize its specific protein (antigen), such as on tumor cells, infected cells or cells mediating autoimmune or inflammatory diseases or disorders. Such receptors are also known as chimeric T cell receptors, chimeric immunoreceptors, or artificial T cell receptors. Upon transduction of a cell with a nucleic acid construct encoding a CAR, the cell will recognize the antigen specified by the CAR. A CAR is typically comprised of an ectodomain (extracellular domain) and an endodomain (cytoplasmic domain), separated by a transmembrane domain. The ectodomain, expressed on the surface of the cell, comprises an antigen binding domain or receptor domain, optionally a signal peptide that directs the antigen binding domain into the endoplasmic reticulum for processing, and optionally a spacer (or hinge) region. The antigen binding domain (or receptor domain) comprises peptides that specifically recognize a target antigen. As a non-limiting example, the antigen binding domain can be a single chain antibody, such as an scFv. The spacer region links the antigen binding domain to the transmembrane domain and is designed to be sufficiently flexible to allow the antigen binding domain to orient in a manner that allows antigen recognition. Examples of spacer domains include, but are not limited to, the hinge region from IgG, the $CH_2CH_3$ region of an immunoglobulin, CD28 hinge, Dap10 hinge, CD8 hinge, and portions of CD3 molecules. The transmembrane domain is a hydrophobic alpha helix, typically, that spans across the lipid bilayer of the cell membrane. The endodomain of the CAR is composed of a signal transmitting peptide that transmits an activation signal intracellularly to the cell cytoplasm, thereby stimulating the cell expressing the CAR. The endodomain may include multiple such signaling domains, as explained, infra. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below. In some aspects, the set of polypeptides encoding the CAR are contiguous with each other. In some embodiments, the set of polypeptides include a dimerization switch that, upon the presence of a dimerization molecule, can couple the polypeptides to one another, e.g., can couple an antigen binding domain to an intracellular signaling domain. In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the CAR comprises a chimeric fusion protein comprising an extracellular antigen binding domain, a transmembrane domain and an intracellular signaling domain comprising a functional signaling domain derived from a stimulatory molecule. In one aspect, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In one aspect, the CAR comprises a chimeric fusion protein comprising an extracellular antigen binding domain, a transmembrane domain and an intracellular signaling domain comprising two functional signaling domains derived from one or more costimulatory molecule (s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen binding domain, wherein the leader sequence is optionally cleaved from the antigen binding domain (e.g., an scFv) during cellular processing and localization of the CAR to the cellular membrane.

Cancer: As used herein, the term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

Disease or disorder: As used herein, the terms "disease" and "disorder" are used interchangeably. The term "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

Identical: As use herein, the term "identical" in the context of polynucleotide and nucleic acid sequences, refers to a first sequence (e.g., an amino acid sequence or a nucleic acid sequence) that contains a sufficient or minimum number of amino acid residues or nucleotide residues that are i) identical to, or ii) conservative substitutions of aligned amino acid or nucleotide residues in a second amino acid sequence or in a second nucleic acid sequence such that the first and second amino acid sequences or nucleic acid sequences can have a common structural domain and/or common functional activity. For example, amino acid sequences contain a common structural domain having at least about 70%, 75%, 80%, 85%, 90%, 91%, 92%, 93%, 94%, 95%, 96%, 97%, 98% or 99% identity to a reference amino acid sequence, e.g., a sequence provided herein. In another example, nucleic acid sequences have at least about 70%, 75%, 80%, 85%, 90%, 91%, 92%, 93%, 94%, 95%, 96%, 97%, 98% or 99% identity to a reference nucleic acid sequence, e.g., a sequence provided herein.

Pharmaceutical composition: As used herein, a "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g, cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy. In preferred embodiments, a pharmaceutical composition comprises a pharmaceutically acceptable carrier, diluent or excipient and one or more cells modified to express a CAR as contemplated herein.

Pharmaceutically acceptable carrier: As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The terms "specific binding affinity" or "specifically binds" or "specifically bound" or "specific binding" or "specifically targets" as used herein, describe binding of an anti-BCMA antibody or antigen binding domain thereof (or a CAR comprising the same) to BCMA (e.g, human BCMA) at greater binding affinity than background binding. A BCMA binding domain (or a CAR comprising the BCMA binding domain) "specifically binds" to a BCMA if it binds to or associates with BCMA with a dissociation constant ($K_d$) of about $1\times10^{-7}$M. In some embodiments, the antigen binding molecule specifically binds an antigen with "high affinity" when the $K_d$ is about $1\times10^{-9}$ M to about $5\times10^{-9}$ M. In some embodiments, the antigen binding molecule specifically binds an antigen with "very high affinity" when the $K_d$ is $1\times10^{-10}$ M to about $5\times10^{-10}$ M. In one embodiment, the antigen binding molecule has a $K_d$ of $10^{-9}$ M. In one embodiment, the off-rate is less than about $1\times10^{-5}$. In other embodiments, the antigen binding molecule binds human BCMA with a $K_d$ of between about $1\times10^{-7}$ M and about $1\times10^{-13}$ M. In yet another embodiment, the antigen binding molecule binds human BCMA with a $K_d$ of about $1\times10^{-10}$ M to about $5\times10^{-10}$ M. Affinities of the BCMA binding domains and CAR proteins according to the present invention can be readily determined using conventional techniques, e.g., by competitive ELISA (enzyme-linked immunosorbent assay), or by binding association, or displacement assays using labeled ligands.

Subject: As used herein, the term "subject" is intended to include living organisms in which an immune response can be elicited (e.g., mammals). Examples of subjects include humans, dogs, cats, mice, rats, and transgenic species thereof.

Therapeutically effective amount: As used herein, the term "therapeutically effective amount" includes an amount that is effective to "treat" a subject (e.g., a patient). When a therapeutic amount is indicated, the precise amount of the compositions to be administered can be determined by a physician with consideration of individual differences in age, weight, tumor size, extent of infection or metastasis, and condition of the patient (subject).

Treat: As used herein, the terms "treatment," "treat," and "treating," refer to a clinical intervention aimed to reverse, alleviate, delay the onset of, or inhibit the progress, and/or prevent or delay the recurrence of a disease or disorder, or one or more symptoms thereof, as described herein. Treatment, e.g., in the form of BCMA CAR expressing NK cells as described herein, may be administered to a subject after one or more symptoms have developed and/or after a disease has been diagnosed. Treatment may be administered in the absence of symptoms, e.g., to prevent or delay onset of a symptom or inhibit onset or progression of a disease. For example, treatment may be administered to a susceptible individual prior to the onset of symptoms (e.g., in light of genetic or other susceptibility factors). Treatment may also be continued after symptoms have resolved, for example to prevent or delay their recurrence.

Various aspects of the compositions and methods herein are described in further detail below. Additional definitions are set out throughout the specification.

Chimeric Antigen Receptor (CAR)

In one aspect, the present invention relates to BCMA (B-cell maturation antigen) targeting CAR polypeptides and polynucleotides encoding the same. The BCMA targeting CAR comprises an extracellular antigen binding region that specifically binds to BCMA, a hinge domain, a transmembrane domain, a DAP10 costimulatory domain, and at least one intracellular activation/signaling domain. The BCMA targeting CAR may further comprises one or more additional polypeptides such as a cytokine (e.g., IL-15). Each component within the CAR is linked by one or more linker sequences.

1. BCMA Binding Region

In accordance with the present invention, the antigen binding region of the present CAR comprises at least one BCMA binding domain (i.e., BCMA binder). The BCMA binding domain can be any agent that binds to BCMA or a portion of BCMA. The BCMA binding domain may be an antibody that specifically binds to BCMA, or antigen binding fragment thereof. The antibody or antigen-binding fragment that specifically binds to BCMA may be a monoclonal antibody, a monospecific antibody, a humanized antibody, a human antibody, a single chain antibody, a domain-specific antibody, a single domain antibody, a domain-deleted antibody, an scFc fusion protein, a single-chain antibody, a chimeric antibody, a synthetic antibody, a recombinant antibody, a hybrid antibody, a mutated antibody, a CDR-grafted antibody, an antibody fragment such as an Fab, an Ftab^ fragment, an Fab' fragment, an F(ab)2 fragment, a Fv fragment, a single-chain Fv (scFv) fragment, an Fd fragmen, a dAb fragment, a diabody, a nanobody, a bivalent nanobody, a shark variable IgNAR domain, a VHH antibody, a camelid antibody, or a minibody.

A suitable BCMA binder according to the present invention may be a scFv that specifically binds to BCMA. A "Single-chain Fv" or "scFv" comprises the VH and VL domains of antibody, wherein these domains are present in a single polypeptide chain and in either orientation (e.g., VL-VH or VH-VL). Typically, scFv can be in a form of VH-linker-VL or VL-linker-VH.

The linker to link the VH and VL chain may comprise an amino acid sequence of (GGGGS)n (SEQ ID NO: 65) (n is an integer of at least 1, 2, 3, 4, 5, 6, 7, 8, 9, or 10). Exemplary linker sequences may include but are not limited to, GGGGSGGGGSGGGGS (SEQ ID NO: 15), GGGGSGGGGSGGGGSGGGGS (SEQ ID NO: 16), GGGGSGGGGSGGGGSGGGGSGGGGS (SEQ ID NO: 17), and GGGGSGGGGSGGGGSGGGGS (SEQ ID NO: 18). In some embodiments, the linker comprises an amino acid sequence at least about 70%, at least about 75%, at least 85%, at least about 85%, at least about 90%, at least about 91%, at least about 92%, at least about 93%, at least about 94%, at least about 95%, at least 96%, at least about 97%, at least about 98%, at least about 99%, or 100% identical to one of SEQ ID NOs: 15-18.

In one exemplary embodiment, the linker of the anti-BCMA scFv comprises an amino acid sequence of GGGGSGGGGSGGGGS (SEQ ID NO: 15).

In some embodiments, the linker is encoded by a nucleic acid sequence comprising SEQ ID NO: 19, SEQ ID NO: 9 or SEQ ID NO: 10.

```
                                                (SEQ ID NO: 9)
GGGGGCGGAGGGTCTGGAGGAGGGGGGAGCGGGGGAGGCGGCTCT (SEQ ID NO: 10)
GGCGGAGGGGGATCTGGAGGAGGAGGAAGTGGAGGCGGTGGCAGC (SEQ ID NO: 19)
GGTGGTGGTGGTTCTGGTGGTGGTGGTTCTGGCGGCGGCGGCTCCGGTG
GTGGTGGATCC
```

In some embodiments, the BCMA binder comprises three heavy chain complementarity determining regions (HCDRs), i.e., HCDR1, HCDR2 and HCDR3 in the heavy chain variable region (VH), and/or three light chain complementarity determining regions (LCDRs), i.e., LCDR1, LCDR2 and LCDR3, in the light chain variable region (VL). In some embodiments, the BCMA binder comprises a VH and/or a VL.

In some embodiments, the BCMA binding domain of the present CAR comprises the HCDR1 having the amino acid sequence of SYAIH (SEQ ID NO: 2), the HCDR2 having the amino acid sequence of VTWHDGSNKYYAESVMG (SEQ ID NO: 3), and the HCDR3 having the amino acid sequence of AKFGEPQYFQH (SEQ ID NO: 4).

In some embodiments, the BCMA binding domain of the present CAR comprises the LCDR1 having the amino acid sequence of RASQGINNYLA (SEQ ID NO: 6), the LCDR2 having the amino acid sequence of AASTLOS (SEQ ID NO: 7), and the LCDR3 having the amino acid sequence of QQLKSYPFT (SEQ ID NO: 8).

In some embodiments, the BCMA binding region comprises a heavy chain variable region (VH) that comprises three complementarity determining regions: HCDR1 comprising SYAIH (SEQ ID NO: 2), HCDR2 comprising VTWHDGSNKYYAESVMG (SEQ ID NO: 3), and HCDR3 comprising AKFGEPQYFQH (SEQ ID NO: 4), and a light chain variable region (VL) that comprises three complementarity determining regions: LCDR1 comprising RASQGINNYLA (SEQ ID NO: 6), LCDR2 comprising AASTLQS (SEQ ID NO: 7), and LCDR3 comprising QQLKSYPFT (SEQ ID NO: 8).

In some embodiments, the BCMA binding domain comprises a VH chain having the amino acid sequence presented by SEQ ID NO: 1.

```
                                                (SEQ ID NO: 1)
QITLRESGGDVVQPGRSLRLSCAASGFTFSSYAIHWVRQAPGKGLEWVA
VTWHDGSNKYYAESVMGRFTISRDNSKNTLYLHMNSLRAEDTGVYYCAR
AKFGEPQYFQHWGQGTLVTVSS
```

It is envisioned that any amino acid substitution at any position other than the CDR sequences can be changed to another amino acid, for example a conservative amino acid substitution (as defined herein). In some embodiments, the VH comprises a sequence that is 70% identical to SEQ ID NO: 1. In some embodiments, the VH comprises a sequence that is 75% identical to SEQ ID NO: 1. In some embodiments, the VH comprises a sequence that is 80% identical to SEQ ID NO: 1. In some embodiments, the VH comprises a sequence that is 85% identical to SEQ ID NO: 1. In some embodiments, the VH comprises a sequence that is 90% identical to SEQ ID NO: 1. In some embodiments, the VH comprises a sequence that is 95% identical to SEQ ID NO: 1. In some embodiments, the VH comprises a sequence that is 96% identical to SEQ ID NO: 1. In some embodiments, the VH comprises a sequence that is 97% identical to SEQ ID NO: 1. In some embodiments, the VH comprises a sequence that is 98% identical to SEQ ID NO: 1. In some embodiments, the VH comprises a sequence that is 99% identical to SEQ ID NO: 1.

In some embodiments, the BCMA binding domain comprises a VL chain having the amino acid sequence of SEQ ID NO: 5.

```
                                                (SEQ ID NO: 5)
DIVMTQSPSFLSASVGDRVTITCRASQGINNYLAWYQQKPGIAPKLLIY
AASTLQSGVPSRFGGSGSGTEFTLTISSLQPEDFATYYCQQLKSYPFTF
GPGTKVEIK.
```

It is envisioned that any amino acid substitution at any position other than the CDR sequences can be changed to another amino acid, for example a conservative amino acid substitution (as defined herein). In some embodiments, the VL comprises a sequence that is 70% identical to SEQ ID NO: 5. In some embodiments, the VL comprises a sequence that is 75% identical to SEQ ID NO: 5. In some embodiments, the VL comprises a sequence that is 80% identical to SEQ ID NO: 5. In some embodiments, the VL comprises a sequence that is 85% identical to SEQ ID NO: 5. In some embodiments, the VL comprises a sequence that is 90% identical to SEQ ID NO: 5. In some embodiments, the VL comprises a sequence that is 95% identical to SEQ ID NO: 5. In some embodiments, the VL comprises a sequence that is 96% identical to SEQ ID NO: 5. In some embodiments, the VL comprises a sequence that is 97% identical to SEQ ID NO: 5. In some embodiments, the VL comprises a sequence that is 98% identical to SEQ ID NO: 5. In some embodiments, the VL comprises a sequence that is 99% identical to SEQ ID NO: 5.

In some embodiments, the BCMA binding domain of the present chimeric antigen receptor comprises a VH chain of SEQ ID NO: 1 and a VL chain of SEQ ID NO: 5.

In some embodiments, the BCMA binding domain of the present chimeric antigen receptor comprises a scFv including a VH chain of SEQ ID NO: 1 and a VL chain of SEQ ID NO: 5 wherein the VH and VL chains are linked by any one of the linker sequences described herein (e.g., SEQ ID NOs: 15-18).

In some embodiments, the BCMA binding domain of the present chimeric antigen receptor comprises a scFv comprising a VH chain of SEQ ID NO: 1 and a VL chain of SEQ ID NO: 5.

As a non-limiting example, the BCMA binding domain of the present chimeric antigen receptor comprises the amino acid sequence presented by SEQ ID NO: 20.

```
                                               (SEQ ID NO: 20)
QITLRESGGDVVQPGRSLRLSCAASGFTFSSYAIHWVRQAPGKGLEWVA
VTWHDGSNKYYAESVMGRFTISRDNSKNTLYLHMNSLRAEDTGVYYCAR
AKFGEPQYFQHWGQGTLVTVSSGGGGSGGGGSGGGGSDIVMTQSPSFLS
ASVGDRVTITCRASQGINNYLAWYQQKPGIAPKLLIYAASTLQSGVPSR
FGGSGSGTEFTLTISSLQPEDFATYYCQQLKSYPFTFGPGTKVEIK.
```

In some embodiments, the BCMA binding domain comprises a scFv having an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 20.

In some embodiments, the BCMA binding scFv is encoded by a nucleic acid sequence of SEQ ID NO: 35, or SEQ ID NO: 51.

In some embodiments, molecules that specifically bind to an antigen bind with a dissociation constant ($K_d$) of about $1\times10^{-7}$ M. In some embodiments, the antigen binding molecule specifically binds an antigen with "high affinity" when the $K_d$ is about $1\times10^{-9}$ M to about $5\times10^{-9}$ M. In some embodiments, the antigen binding molecule specifically binds an antigen with "very high affinity" when the $K_d$ is $1\times10^{-10}$ M to about $5\times10^{-10}$ M. In one embodiment, the antigen binding molecule has a $K_d$ of $10^{-9}$ M. In one embodiment, the off-rate is less than about $1\times10^{-5}$. In other embodiments, the antigen binding molecule binds human BCMA with a $K_d$ of between about $1\times10^{-7}$ M and about $1\times10^{-13}$ M. In yet another embodiment, the antigen binding molecule binds human BCMA with a $K_d$ of about $1\times10^{-10}$ M to about $5\times10^{-10}$ M.

In another specific embodiment, molecules that specifically bind to BCMA do not cross react with other proteins under similar binding conditions. In another specific embodiment, molecules that specifically bind to BCMA do not cross react with other non-BCMA proteins. In a specific embodiment, provided herein is an antibody or fragment thereof that binds to BCMA with higher affinity than to another unrelated antigen. In certain embodiments, provided herein is an antibody or fragment thereof that binds to BCMA (e.g., human BCMA) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-BCMA antibody or antigen-binding fragment thereof described herein to an unrelated, non-BCMA protein is less than 10%, 15%, or 20% of the binding of the antibody to BCMA protein as measured by, e.g., a radioimmunoassay.

In a specific embodiment, provided herein is a chimeric antigen receptor that binds to human BCMA with higher affinity than to another species of BCMA. In certain embodiments, provided herein is an antibody or fragment thereof that binds to human BCMA with a 5%, 10%, 15%, 20%, 25%, 30%, 35%, 40%, 45%, 50%, 55%, 60%, 65%, 70%, 75%, 80%, 85%, 90%, 95% or higher affinity than to another species of BCMA as measured by, e.g., a radioimmunoassay, surface plasmon resonance, or kinetic exclusion assay. In a specific embodiment, a chimeric antigen receptor comprising a BCMA binder, which binds to human BCMA, will bind to another species of BCMA protein with less than 10%, 15%, or 20% of the binding of the antibody or fragment thereof to the human BCMA protein as measured by, e.g., a radioimmunoassay, surface plasmon resonance, or kinetic exclusion assay.

2. Hinge Region

In certain aspects, the BCMA targeting CAR polypeptide of the present invention can include a hinge domain positioned between the extracellular antigen binding domain and the transmembrane domain. A hinge domain may be included in CAR polypeptides to provide adequate distance between the antigen binding domain and the cell surface or to alleviate possible steric hindrance that could adversely affect antigen binding or effector function of CAR-gene modified immune cells. For example, the hinge domain can position the antigen binding domain away from the effector cell surface to enable proper cell/cell contact, antigen binding and activation.

The hinge domain is of a particular length, such as 10-50, 10-40, 10-30, 10-20, 10-15, 20-50, 20-40, 20-30, 15-50, 15-45, 15-30, 15-20, 12-20, 12-15, or 15-20 amino acids in length.

In some embodiments, the hinge domain is derived from human CD28 hinge domain. As a non-limiting example, the hinge domain of the BCMA targeting CAR polypeptide comprises a CD28 hinge domain having the amino acid sequence of SEQ ID NO: 21: RAAAIEVMYPPPYLD-NEKSNGTIIHVKGKHLCPSPLFPGPSKPKDPK. In certain specific aspects, the hinge domain comprises an amino acid sequence that is at least about 70%, at least about 75%, at least about 80%, at least about 85%, at least about 90%, at least about 91%, at least about 92%, at least about 93%, at least about 94%, at least about 95%, at least about 96%, at least about 97%, at least 98%, or at least about 99% identical to SEQ ID NO: 21. In some embodiments, the CD28 hinge domain may be encoded by a nucleic acid sequence of SEQ ID NO: 37, or SEQ ID NO: 54.

In some embodiments, the hinge domain is derived from human CD28 hinge domain. As a non-limiting example, the hinge domain of the BCMA targeting CAR polypeptide comprises a CD28 hinge domain having the amino acid sequence of SEQ ID NO: 61: IEVMYPPPYLD-NEKSNGTIIHVKGKHLCPSPLFPGPSKP. In certain specific aspects, the hinge domain comprises an amino acid sequence that is at least about 70%, at least about 75%, at least about 80%, at least about 85%, at least about 90%, at least about 91%, at least about 92%, at least about 93%, at least about 94%, at least about 95%, at least about 96%, at least about 97%, at least 98%, or at least about 99% identical to SEQ ID NO: 61. In some embodiments, the CD28 hinge domain may be encoded by a nucleic acid sequence of SEQ ID NO: 62, or SEQ ID NO: 63.

Alternatively and optionally, one or more hinge or spacer domains derived from other protein may be used. As used herein, the term "spacer domain" refers to the region that moves the antigen binding domain away from the effector cell surface to enable proper cell/cell contact, antigen binding and activation (Patel et al., Gene Therapy, 1999; 6:412-419). The spacer domain may be derived either from a natural, synthetic, semi-synthetic, or recombinant source. For example, the hinge and spacer domains can be derived from a human IgG hinge domain, a CD8a hinge domain, or an Fc domain from a human immunoglobulin (e.g., IgG1, IgG2, IgG3, IgG4, IgA1, IgA2, IgM, IgD or IgE) that binds to an Fc receptor.

In some embodiments, the BCMA targeting CARs contemplated herein may comprise a modified hinge domain and/or spacer domain. The modified hinge domain and/or spacer domain may comprise up to 30% amino acid changes (e.g., up to 25%, 20%, 15%, 10%, or 5% amino acid substitutions or deletions), or a portion of a naturally occurring hinge region that is at least 10 amino acids (e.g., at least 12, 13, 14 or 15 amino acids) in length with up to 30% amino acid changes (e.g., up to 25%, 20%, 15%, 10%, or 5% amino acid substitutions or deletions), or a portion of a naturally occurring hinge region that comprises the core hinge region (which may be 4, 5, 6, 7, 8, 9, 10, 11, 12, 13, 14, or 15, or at least 4, 5, 6, 7, 8, 9, 10, 11, 12, 13, 14, or 15 amino acids in length).

3. Transmembrane Domain

In various embodiments, the extracellular antigen binding domain and the intracellular signaling domain of the BCMA targeting CAR of the present invention may be fused by a transmembrane domain. The transmembrane domain can also anchor the CAR to the plasma membrane of the immune effector cell. The transmembrane domain may be derived from any membrane-bound or transmembrane protein. The transmembrane domain may be derived from a natural, synthetic, semi-synthetic, or recombinant source. In some aspects, the amino acid sequence of the transmembrane domain may be modified or substituted so as to minimize, e.g., interactions with the binding domains of the native binding partner present in the same CAR-expressing cell.

In some embodiments, the transmembrane domain of the BCMA targeting CAR of the present invention is derived from the transmembrane domain of human CD28. For example, the CD28 transmembrane domain of the BCMA targeting CAR polypeptide may comprise the amino acid sequence of SEQ ID NO: 22: FWVLVVVGGVLACYSLL-VTVAFIIFWV. In some aspects, for example, the transmembrane domain comprises a sequence at least 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO: 22. In some embodiments, the CD28 transmembrane domain may be encoded by a nucleic acid sequence of SEQ ID NO: 38, or SEQ ID NO: 56.

Alternatively, the transmembrane domain of the CAR may include the transmembrane region(s) of the alpha, beta or zeta chain of the T-cell receptor, CD3 epsilon, CD45, CD4, CD5, CD8, CD9, CD16, CD22, CD33, CD37, CD64, CD80, CD86, CD134, CD137, CD154.

4. Cytoplasmic Domains

The cytoplasmic region of a CAR polypeptide includes an intracellular activation signaling domain. The intracellular signaling domain of the chimeric antigen receptor is responsible for activation of at least one of the normal effector functions of the immune cell engineered to express a chimeric antigen receptor. The term "effector function" in general refers to a specialized function of a differentiated cell. Effector function of an immune cell (e.g., NK cell or T cell) can be the cytolytic activity, cytotoxic activity or helper activity including the secretion of cytokines, to kill tumor cells. In this context, the term "intracellular signaling domain" refers to the portion of a protein that transduces the effector function signal and directs the cell to perform a specialized function. In some embodiments, the intracellular signaling domain is derived from the intracellular signaling domain of a native activating protein. Examples of such native activating proteins such as native receptors including the zeta chain of the T-cell receptor or any of its homologs (e.g., eta, delta, gamma, or epsilon), MB1 chain, B29, Fc RIII, Fc RI, signaling molecules such as CD3ζ, CD28, CD27, 4-IBB, DAP10, OX40, and other similar molecules. While usually the entire intracellular signaling domain will be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term "intracellular signaling domain" is thus meant to include a truncated portion of the intracellular signaling domain sufficient to transduce the effector function signal, upon CAR binding to a target.

In one preferred embodiment, the human CD3ζ intracellular signaling domain is used as the intracellular signaling domain for a BCMA targeting CAR polypeptide of the present invention. An example of the CD3ζ intracellular signaling domain comprises the amino acid sequence of SEQ ID NO: 23.

```
                                          (SEQ ID NO: 23)
RVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR.
```

In certain specific aspects, the intracellular signaling domain comprises an amino acid sequence that is at least about 70%, at least about 75%, at least about 80%, at least about 85%, at least about 90%, at least about 91%, at least about 92%, at least about 93%, at least about 94%, at least about 95%, at least about 96%, at least about 97%, at least 98%, or at least about 99% identical to SEQ ID NO: 23. In some embodiments, the CD3ζ intracellular signaling domain may be encoded by a nucleic acid sequence of SEQ ID NO: 40, or SEQ ID NO: 58.

In some embodiments, the BCMA targeting CAR polypeptide may comprise one or more co-stimulatory signaling domains. An intracellular costimulatory signaling domain refers to the intracellular portion of a costimulatory molecule. The term "costimulatory molecule" refers to the cognate binding partner on an immune cell that specifically binds with a costimulatory ligand, thereby mediating a costimulatory response by the immune cell, such as, but not limited to, proliferation.

In some embodiments, the present BCMA targeting CAR polypeptide comprises a costimulatory domain derived from DAP10 (Hematopoietic cell signal transducer precursor (DNAX-activation protein 10)). An example of the DAP10 derived costimulatory domain comprises the amino acid sequence of LCARPRRSPAQEDGKVYINMPGRG (SEQ ID NO: 24). In certain aspects, the DAP10 costimulatory domain comprises an amino acid sequence that is at least about 70%, at least about 75%, at least about 80%, at least about 85%, at least about 90%, at least about 91%, at least about 92%, at least about 93%, at least about 94%, at least about 95%, at least about 96%, at least about 97%, at least 98%, or at least about 99% identical to SEQ ID NO: 24. In some embodiments, the DAP10 costimulatory domain may be encoded by a nucleic acid sequence of SEQ ID NO: 39, or SEQ ID NO: 57.

The costimulatory domain derived from CD28 may be utilized in the present BCMA targeting CAR polypeptide. An example of CD28 co-stimulatory domain comprises the amino acid sequence of SEQ ID NO: 64.

```
                                          (SEQ ID NO: 64)
RSKRSRLLHSDYMNMTPRRPGPTRKHYQPYAPPRDFAAYRS.
```

In addition to the DAP10 derived costimulatory domain and the CD35 intracellular signaling domain, a BCMA targeting CAR polypeptide as described herein may comprise one or more costimulatory domains, and/or one or more intracellular activation signaling domains. The costimulatory domains and intracellular activation signaling domains may be derived from, e.g., an MHC class I molecule, TNF receptor proteins, Immunoglobulin-like proteins, cytokine receptors, integrins, signaling lymphocytic activation molecules (SLAM proteins), activating NK cell receptors, BTLA, Toll ligand receptor, OX-40, 4-1BB/CD137, CD2, CD7, CD27, CD28, CD30, CD40, programmed death-1 (PD-1), inducible T cell costimulator (ICOS), CDS gamma, CD3 delta, CD3 epsilon, CD247, CD276 (B7-H3), LIGHT (tumor necrosis factor superfamily member 14; TNFSF1.4), NKG2C, 2B4, Ig alpha (CD79a), DAP12, Fc gamma receptor, MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD 19, CD4, CDSalpha, CDSbeta, 11.2 beta, IL2R gamma, IL7R alpha, ITGA4, VLA1, CD49a, ITGA4, IA4, CD49D, ITGA6, VLA-6, CD49f, ITGAD, ITGAE, CD103, ITGAL, LFA-1, ITGAM, ITGAX, ITGB1, CD29, ITGB2, ICOS, CD18, LFA-1, ITGB7, NKG2D, TNFR2, TRANCE RANKL, DNAM1 (CD226), SLAMF4 (CD244, 2B4), CD84, CD96 (Tactile), CEACAM1, CRT AM, Ly9 (CD229), CD160 (BY55), PSGL1, CDIOO (SEMA4D), CD69, SLAMF6 (NTB-A, Ly108), BLAME (SLAMF8), SELPLG (CD 162), LTBR, LAT, GADS, SLP-76, PAG/Cbp, CD 19a, a ligand that specifically binds with CD83, or any combination thereof.

5. Other Components

In some embodiments, one or more other polypeptides and/or proteins may be incorporated into the BCMA targeting CAR constructs as described herein. The additional proteins and polypeptides may be utilized for any function, e.g., the activity of the CAR polypeptide and/or any cells expressing the CAR.

In some embodiments, the BCMA targeting CAR polypeptide as described herein may further comprise one or more cytokines. The CAR and the other protein(s) may be separated by a cleavable 2A sequence, for example.

In one exemplary embodiment, the cytokine IL-15 is incorporated in to the BCMA targeting CAR construct. IL-15 is a proinflammatory cytokine, important for the differentiation and proliferation of T-cells, NK-cells, and the development of dendritic cells. An example of IL15 comprises the amino acid sequence of SEQ ID NO: 26.

(SEQ ID NO: 26)
GIHVFILGCFSAGLPKTEANWVNVISDLKKIEDLIQSMHIDATLYTESD

VHPSCKVTAMKCFLLELQVISLESGDASIHDTVENLIILANNSLSSNGN

VTESGCKECEELEEKNIKEFLQSFVHIVQMFINTS

In some embodiments, the IL15 protein incorporated into the BCMA targeting CAR construct comprises an amino acid sequence that is at least about 70%, at least about 75%, at least about 80%, at least about 85%, at least about 90%, at least about 91%, at least about 92%, at least about 93%, at least about 94%, at least about 95%, at least about 96%, at least about 97%, at least 98%, or at least about 99% identical to SEQ ID NO: 26.

In one embodiment, the IL-15 peptide encoded by the nucleic acid sequence of SEQ ID NO: 52, or SEQ ID NO: 53.

In some aspects, the CAR polypeptide and other proteins e.g., IL-15) in the same construct are intended to be produced into two different polypeptides, a cleavable 2A sequence may be utilized (e.g., T2A, F2A, and E2A). The 2A self-cleaving peptides (i.e., 2A peptides), are a class of 18-22 AA-long peptides, which can induce ribosomal skipping during translation of a protein in a cell. These peptides share a core sequence motif of DxExNPGP, and are found in a wide range of viral families. They help generating polyproteins by causing the ribosome to fail at making a peptide bond. The members of 2A peptides are named after the virus in which they have been first described. For example, F2A, the first described 2A peptide, is derived from foot-and-mouth disease virus. The name "2A" itself comes from the gene numbering scheme of this virus.

In some embodiments, the cleavable peptide is E2A. As a non-limiting example, the E2A comprises the sequence of GPQCTNYALLKLAGDVESNPGP (SEQ ID NO: 27). In some embodiments, the cleavable peptide is positioned between the CAR polypeptide and IL-15.

The BCMA targeting CAR as described herein may further comprise a signal peptide. The signal peptide may comprise 3-30, 3-20, 3-15, 5-30, 5-20, 5-15, 10-30, 10-20, or 10-15 amino acid residues. An example of the signal peptide comprises the sequence of MEFGLSWLFLVAILKGVQC (SEQ ID NO: 28). An example of the signal peptide comprises the sequence of MRISKPHLRSISIQCYLCLLLN-SHFLTEA (SEQ ID NO: 59).

In one exemplary embodiment, the BCMA targeting CAR comprises a signal peptide, a BCMA binding domain, a hinge and a transmembrane domain, a DAP10 costimulatory domain and at least one intracellular signaling domain.

In another exemplary embodiment, the construct to express the BCMA targeting CAR comprises a signal peptide, an extracellular BCMA binding domain, a hinge and a transmembrane domain, a DAP10 costimulatory domain and at least one intracellular signaling domain and a cytokine.

In one exemplary embodiment, a suicide gene product such as caspase 9 (e.g., inducible caspase 9) is utilized in conjunction with the CAR.

Example Caspase 9 Amino Acid Sequence:

(SEQ ID NO: 14)
MLEGVQVETISPGDGRTFPKRGQTCVVHYTGMLEDGKKVDSSRDRNKPF

KFMLGKQEVIRGWEEGVAQMSVGQRAKLTISPDYAYGATGHPGIIPPHA

TLVFDVELLKLESGGGSGVDGFGDVGALESLRGNADLAYILSMEPCGHC

LIINNVNFCRESGLRTRTGSNIDCEKLRRRFSSLHFMVEVKGDLTAKKM

VLALLELAQQDHGALDCCVVVILSHGCQASHLQFPGAVYGTDGCPVSVE

KIVNIFNGTSCPSLGGKPKLFFIQACGGEQKDHGFEVASTSPEDESPGS

NPEPDATPFQEGLRTFDQLDAISSLPTPSDIFVSYSTFPGFVSWRDPKS

GSWYVETLDDIFEQWAHSEDLQSLLLRVANAVSVKGIYKQMPGCFNFLR

KKLFFKTSAS

Any polypeptide encompassed by the present disclosure may comprise SEQ ID NO:14 or an amino acid sequence that is at least 70%, 75%, 80%, 85%, 90%, 95%, 96%, 97%, 98%, 99%, or 100% identical to SEQ ID NO:14.

6. Linkers

The BCMA targeting CAR contemplated herein may comprise linker residues between the various domains. In some embodiments, the BCMA targeting CARs contemplated herein, may comprise one, two, three, four, or five or more linkers. In particular embodiments, the length of a linker is about 1 to about 30 amino acids, about 1 to about 25 amino acids, about 5 to about 30 amino acids, about 5 to about 25 amino acids, bout 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acids in length. The ordinarily skilled artisan will recognize that design of a CAR in particular embodiments can include linkers that are all or partially flexible, such that the linker can include a flexible linker as well as one or more portions that confer less flexible structure to provide for a desired CAR structure.

In one exemplary embodiment, the BCMA targeting CAR polypeptide of the present invention comprises the amino acid sequence of SEQ ID NO: 29.

(SEQ ID NO: 29)
QITLRESGGDVVQPGRSLRLSCAASGFTESSYAIHWVRQAPGKGLEWVA

VTWHDGSNKYYAESVMGRFTISRDNSKNTLYLHMNSLRAEDTGVYYCAR

AKFGEPQYFQHWGQGTLVTVSSGGGGSGGGGSGGGGSDIVMTQSPSFLS

ASVGDRVTITCRASQGINNYLAWYQQKPGIAPKLLIYAASTLQSGVPSR

FGGSGSGTEFTLTISSLOPEDFATYYCQQLKSYPFTFGPGTKVEIKRAA

AIEVMYPPPYLDNEKSNGTIIHVKGKHLCPSPLFPGPSKPKDPKFWVLV

VVGGVLACYSLLVTVAFIIFWVLCARPRRSPAQEDGKVYINMPGRGRVK

FSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTY

DALHMQALPPR

In some embodiments, the BCMA targeting CAR polypeptide may comprise an amino acid sequence that is at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO: 29.

In one aspect of the present invention, a BCMA targeting CAR polypeptide includes, from N-terminal to C-terminal end:

Signal Sequence 1-BCMA binder-linker-CD28 (hinge)-linker-CD28 (TM)-DAP10 (costim)-CD3z-E2A-Signal sequence 2-sIL15.

In one exemplary embodiment, the BCMA targeting CAR polypeptide of the present invention comprises the amino acid sequence of SEQ ID NO: 13.

(SEQ ID NO: 13)
MEFGLSWLFLVAILKGVQCQITLRESGGDVVQPGRSLRLSCAASGFTFS

SYAIHWVRQAPGKGLEWVAVTWHDGSNKYYAESVMGRFTISRDNSKNTL

YLHMNSLRAEDTGVYYCARAKFGEPQYFQHWGQGTLVTVSSGGGGSGGG

GSGGGGSDIVMTQSPSFLSASVGDRVTITCRASQGINNYLAWYQQKPGI

APKLLIYAASTLQSGVPSRFGGSGSGTEFTLTISSLQPEDFATYYCQQL

KSYPFTFGPGTKVEIKRAAAIEVMYPPPYLDNEKSNGTIIHVKGKHLCP

SPLFPGPSKPKDPKFWVLVVVGGVLACYSLLVTVAFIIFWVLCARPRRS

PAQEDGKVYINMPGRGRVKFSRSADAPAYQQGQNQLYNELNLGRREEYD

VLDKRRGRDPEMGGKPRRKNPQEGLYNELQKDKMAEAYSEIGMKGERRR

GKGHDGLYQGLSTATKDTYDALHMQALPPRGPQCTNYALLKLAGDVESN

PGPMRISKPHLRSISIQCYLCLLLNSHFLTEAGIHVFILGCFSAGLPKT

EANWVNVISDLKKIEDLIQSMHIDATLYTESDVHPSCKVTAMKCFLLEL

QVISLESGDASIHDTVENLIILANNSLSSNGNVTESGCKECEELEEKNI

KEFLQSFVHIVQMFINTS

The BCMA targeting CAR polypeptide may comprise an amino acid sequence that is at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO: 13.

Polynucleotides Encoding BCMA Targeting CARs

In another aspect, the present invention provides nucleic acid molecules encoding one or more CAR polypeptides as described herein. As used herein, the terms "nucleic acid molecule" and "polynucleotide" are used interchangeably. In some embodiments, the nucleic acid molecule is provided as a messenger RNA (mRNA) molecule. In other embodiments, the nucleic acid molecule is provided as a DNA construct. In some aspects, the DNA construct is a non-viral vector such as a plasmid, a cosmid or an artificial chromosome. In other aspects, the DNA construct is a viral based vector such as AAV, lentivirus and retrovirus.

Accordingly, the present invention provides a polynucleotide encoding a BCMA targeting CAR polypeptide, wherein the CAR comprises an anti-BCMA binding domain (e.g., a human anti-BCMA binding domain), a hinge domain, a transmembrane domain, a DAP10 costimulatory domain and an intracellular signaling domain comprising a primary signaling domain of CD3ζ. In some embodiments, the polynucleotide further comprises a nucleic acid sequence encoding one or more polypeptides that are incorporated into the CAR construct. For example, the polynucleotide further comprises a nucleic acid sequence encoding a cytokine such as IL-15. In some embodiments, the polynucleotide further comprises nucleic acid sequences for a single peptide and/or a linker sequence (e.g., E2A)

In some embodiments, the BCMA binding domain is an anti-BCMA binding domain described herein. In some examples, the BCMA binding domain is encoded by a nucleic acid sequence of any one of SEQ ID NOs: 30, 35-36 and 47-51. In some embodiments, the nucleic acid sequence encoding the BCMA binding domain of the CAR comprises a nucleic acid sequence that is at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to one of the sequences of SEQ ID NOs: 30, 35-36 and 47-51.

In some embodiments, the polynucleotide encoding the BCMA targeting CAR comprises the nucleic acid sequence of SEQ ID NO: 30 and the nucleic acid sequence of SEQ ID NO: 32.

In some embodiments, the polynucleotide encoding the BCMA targeting CAR comprises the nucleic acid sequence of SEQ ID NO: 30 and the nucleic acid sequence of SEQ ID NO: 49.

In some embodiments, the polynucleotide encoding the BCMA targeting CAR comprises the nucleic acid sequence of SEQ ID NO: 30 and the nucleic acid sequence of SEQ ID NO: 50.

In some embodiments, the polynucleotide encoding the BCMA targeting CAR comprises the nucleic acid sequence of SEQ ID NO: 32 and the nucleic acid sequence of SEQ ID NO: 47.

In some embodiments, the polynucleotide encoding the BCMA targeting CAR comprises the nucleic acid sequence of SEQ ID NO: 32 and the nucleic acid sequence of SEQ ID NO: 48.

In some embodiments, the polynucleotide encoding the BCMA targeting CAR comprises the nucleic acid sequence of SEQ ID NO: 47 and the nucleic acid sequence of SEQ ID NO: 49.

In some embodiments, the polynucleotide encoding the BCMA targeting CAR comprises the nucleic acid sequence of SEQ ID NO: 48 and the nucleic acid sequence of SEQ ID NO: 50.

An exemplary nucleic acid sequence encoding the BCMA binding domain comprises SEQ ID NO: 35, or a sequence that is about 70%, 75%, 80%, 85%, 90%, 91%, 92%, 93%, 94%, 95%, 96%, 97%, 98%, or 99% identical to SEQ ID NO: 35.

An exemplary nucleic acid sequence encoding the BCMA binding domain comprises SEQ ID NO: 36, or a sequence that is about 70%, 75%, 80%, 85%, 90%, 91%, 92%, 93%, 94%, 95%, 96%, 97%, 98%, or 99% identical to SEQ ID NO: 36.

The nucleic acid sequence encoding the BCMA binding domain may be codon optimized. In one embodiment, the codon-optimized nucleic acid sequence encoding the BCMA binding domain comprises SEQ ID NO: 51. In some embodiments, the codon-optimized nucleic acid sequence encoding the BCMA binding domain comprises a nucleic acid sequence about 75% identical to SEQ ID NO: 51. In some embodiments, the codon-optimized nucleic acid sequence encoding the BCMA binding domain comprises a nucleic acid sequence about 80% identical to SEQ ID NO: 51. In some embodiments, the codon-optimized nucleic acid sequence encoding the BCMA binding domain comprises a nucleic acid sequence about 85% identical to SEQ ID NO: 51. In some embodiments, the codon-optimized nucleic acid sequence encoding the BCMA binding domain comprises a nucleic acid sequence about 90% identical to SEQ ID NO: 51. In some embodiments, the codon-optimized nucleic acid sequence encoding the BCMA binding domain comprises a nucleic acid sequence about 91% identical to SEQ ID NO: 51. In some embodiments, the codon-optimized nucleic acid sequence encoding the BCMA binding domain comprises a nucleic acid sequence about 92% identical to SEQ ID NO: 51. In some embodiments, the codon-optimized nucleic acid sequence encoding the BCMA binding domain comprises a nucleic acid sequence about 93% identical to SEQ ID NO: 51. In some embodiments, the codon-optimized nucleic acid sequence encoding the BCMA binding domain comprises a nucleic acid sequence about 94% identical to SEQ ID NO: 51. In some embodiments, the codon-optimized nucleic acid sequence encoding the BCMA binding domain comprises a nucleic acid sequence about 95% identical to SEQ ID NO: 51. In some embodiments, the codon-optimized nucleic acid sequence encoding the BCMA binding domain comprises a nucleic acid sequence about 96% identical to SEQ ID NO: 51. In some embodiments, the codon-optimized nucleic acid sequence encoding the BCMA binding domain comprises a nucleic acid sequence about 97% identical to SEQ ID NO: 51. In some embodiments, the codon-optimized nucleic acid sequence encoding the BCMA binding domain comprises a nucleic acid sequence about 98% identical to SEQ ID NO: 51. In some embodiments, the codon-optimized nucleic acid sequence encoding the BCMA binding domain comprises a nucleic acid sequence about 99% identical to SEQ ID NO: 51.

In another embodiment, the codon optimized nucleic acid sequence encoding the BCMA binding domain comprises SEQ ID NO: 35. In some embodiments, the codon-optimized nucleic acid sequence encoding the BCMA binding domain comprises a nucleic acid sequence about 75% identical to SEQ ID NO: 35. In some embodiments, the codon-optimized nucleic acid sequence encoding the BCMA binding domain comprises a nucleic acid sequence about 80% identical to SEQ ID NO: 35. In some embodiments, the codon-optimized nucleic acid sequence encoding the BCMA binding domain comprises a nucleic acid sequence about 85% identical to SEQ ID NO: 35. In some embodiments, the codon-optimized nucleic acid sequence encoding the BCMA binding domain comprises a nucleic acid sequence about 90% identical to SEQ ID NO: 35. In some embodiments, the codon-optimized nucleic acid sequence encoding the BCMA binding domain comprises a nucleic acid sequence about 91% identical to SEQ ID NO: 35. In some embodiments, the codon-optimized nucleic acid sequence encoding the BCMA binding domain comprises a nucleic acid sequence about 92% identical to SEQ ID NO: 35. In some embodiments, the codon-optimized nucleic acid sequence encoding the BCMA binding domain comprises a nucleic acid sequence about 93% identical to SEQ ID NO: 35. In some embodiments, the codon-optimized nucleic acid sequence encoding the BCMA binding domain comprises a nucleic acid sequence about 94% identical to SEQ ID NO: 35. In some embodiments, the codon-optimized nucleic acid sequence encoding the BCMA binding domain comprises a nucleic acid sequence about 95% identical to SEQ ID NO: 35. In some embodiments, the codon-optimized nucleic acid sequence encoding the BCMA binding domain comprises a nucleic acid sequence about 96% identical to SEQ ID NO: 35. In some embodiments, the codon-optimized nucleic acid sequence encoding the BCMA binding domain comprises a nucleic acid sequence about 97% identical to SEQ ID NO: 35. In some embodiments, the codon-optimized nucleic acid sequence encoding the BCMA binding domain comprises a nucleic acid sequence about 98% identical to SEQ ID NO: 35. In some embodiments, the codon-optimized nucleic acid sequence encoding the BCMA binding domain comprises a nucleic acid sequence about 99% identical to SEQ ID NO: 35.

TABLE 1

Sequences of BCMA binding domains

| Ab# | Type | Sequence (5'-3') |
|---|---|---|
| VH | Amino acid | QITLRESGGDVVQPGRSLRLSCAASGFTFSSYAIHWVRQAPGKGLEWVAVT WHDGSNKYYAESVMGRFTISRDNSKNTLYLHMNSLRAEDTGVYYCARAKF GEPQYFQHWGQGTLVTVSS (SEQ ID NO: 1) |
| | Nucleotide | cagatcactttaagggagagcggaggcgatgtggtgcagcccggtcgttctttaagactgagctgtgccgccagcggctt caccttcagcagctacgccatccactgggtgagacaagctcccggtaaaggtttagagtgggtggctgtgacttggcacg acggctccaacaagtactatgccgagagcgtgatgggtcgtttcaccatctctcgtgacaacagcaagaacactttatat ttacacatgaactctttaagggccgaggacaccggcgtgtactactgcgccagagccaagttcggcgagccccagtactt ccagcactggggccaaggtacactggtgaccgtgtccagc (SEQ ID NO: 30) |

TABLE 1-continued

Sequences of BCMA binding domains

| Ab# | Type | Sequence (5'-3') |
|---|---|---|
| | Nucleotide | cagataactctgcgcgagtcaggaggagacgtggtgcaacccgggcagatctctcaggctttcatgtgccgccagtggctt cacatttagctcttatgcaatacattgggtcaggcaggctcctggcaagggcttggaatgggtagcggttacctggcatg atggatctaacaaatactacgccgagtctgttatgggtcgattcacaatttctcgagacaattcaaaaaacacactctac ctgcatatgaactcacttagagcagaggacactggtgtctattactgcgccagagcaaaattcggcgagccacagtattt ccagcactggggacaaggaaccctcgtaacagtatctagt (SEQ ID NO: 47) |
| | Nucleotide | cagatcaccctgagggagtctgaggcgacgtggtgcagcctggaaggagcctgagactgagctgcgccgcctctgg attcaccttcagcagctacgccatccactgggtcaggcaggctcctggcaagggactggagtgggtggccgttacctgg cacgacggcagcaacaagtactacgccgagagcgttatgggcaggttcaccatcagcagggacaacagcaagaacac cctgtacctgcacatgaactctctgagggccgaggacacaggcgtgtactactgcgccagggccaagttcggtgagccc cagtacttccagcactggggccagggaaccctggtgaccgtgtcttct (SEQ ID NO: 48) |
| VL | Amino acid | DIVMTQSPSFLSASVGDRVTITCRASQGINNYLAWYQQKPGIAPKLLIYAAST LQSGVPSRFGGSGSGTEFTLTISSLQPEDFATYYCQQLKSYPFTFGPGTKVEIK (SEQ ID NO: 5) |
| | Nucleotide | gacatcgtgatgacccagagccctagcttttaagcgccagcgtgggcgacagagtgaccatcacttgtcgtgccagcca aggtatcaacaactatttagcttggtaccagcagaagcccggtatcgcccccaagctgctgatctacgccgccagcacac tgcagagcggcgtgcctagcagatttggtggcagcggctctggcacagagttcactttaaccatcagctctttacagccc gaggacttcgccacctactactgccagcagctgaagagctacccctcaccttcggccccggcaccaaggtggagatcaa g (SEQ ID NO: 32) |
| | Nucleotide | gatattgttatgacccaatcaccatcttttctgagcgctagtgtcggcgacagggttacaatcacatgccgagca agccaaggaatcaacaattatctcgcatggtatcaacaaaaaccaggtatcgccccgaaacttcttatttacgca gcatcaaccctgcaaagcggagttccttctagatttggtggcagcggctccgggactgaattcactcttactattt cctcccttcaacccgaagatttcgccacatattactgccagcagcttaagtcataccccttcacttttggcccagg aactaaagttgaaatcaaa (SEQ ID NO: 49) |
| | Nucleotide | gacatcgtgatgacccagagccctagcttcctgtctgccagcgtgggagacagggtgaccatcacctgcagagccagcc agggcatcaataactacctggcctggtaccagcagaagcccggcattgccccaagctcctgatctacgccgccagcac cctgcaaagcggcgtgccctctaggttcggcggatctggaagcggcaccgagttcaccctgaccattagcagcctgcag cccgaggacttcgccacctactactgccagcagctgaagagctacccttcaccttcggccctggcaccaaggtggaga tcaag (SEQ ID NO: 50) |
| scFv | Amino acid | QITLRESGGDVVQPGRSLRLSCAASGFTFSSYAIHWVRQAPGKGLEWVAVT WHDGSNKYYAESVMGRFTISRDNSKNTLYLHMNSLRAEDTGVYYCARAKF GEPQYFQHWGQGTLVTVSSGGGGSGGGGSGGGGSDIVMTQSPSFLSASVGD RVTITCRASQGINNYLAWYQQKPGIAPKLLIYAASTLQSGVPSRFGGSGSGTE FTLTISSLQPEDFATYYCQQLKSYPFTFGPGTKVEIK (SEQ ID NO: 20) |
| | Nucleotide | cagatcactttaagggagagcggaggcgatgtggtgcagcccggtcgttcttttaagactgagctgtgccgccagcggctt caccttcagcagctacgccatccactgggtgagacaagctcccggtaaaggtttagagtgggtggctgtgacttggcacg acggctccaacaagtactatgccgagacgtgatgggtcgtttccaccatctctcgtgacaacagcaagaacacttatat ttacacatgaactctcttaagggccgaggacaccggcgtgtactactgcgccagagccaagttcggcgagcccagtactt ccagcactggggccaaggtacactggtgaccgtgtccagcggggcggagggtctggaggaggggggagcggg ggaggcggctctgacatcgtgatgacccagagccctagcttttaagcgccagcgtgggcgacagagtgaccatcact tgtcgtgccagccaaggtatcaacaactatttagcttggtaccagcagaagcccggtatcgcccccaagctgctgatcta cgccgccagcacactgcagagcggcgtgcctagcagatttggtggcagcggctctggcacagagttcactttaaccatca gctctttacagcccgaggacttcgccacctactactgccagcagctgaagagctaccccttcaccttcggccccggcacc aaggtggagatcaag (SEQ ID NO: 36) |
| | Nucleotide | cagataactctgcgcgagtcaggaggagacgtggtgcaacccgggcagatctctcaggctttcatgtgccgcc agtggcttcacatttagctcttatgcaatacattgggtcaggcaggctcctggcaagggcttggaatgggtagcg gttacctggcatgatggatctaacaaatactacgccgagtctgttatgggtcgattcacaatttctcgagacaattc aaaaaacacactctacctgcatatgaactcacttagagcagaggacactggtgtctattactgcgccagagcaa aattcggcgagccacagtattccagcactggggacaaggaaccctcgtaacagtatctagtggggggcggag ggtctggaggaggggggagcggggaggcggctctgatattgttatgacccaatcaccatcttttctgagcgc tagtgtcggcgacagggttacaatcacatgccgagcaagccaaggaatcaacaattatctcgcatggtatcaac aaaaaccaggtatcgccccgaaacttcttatttacgcagcatcaaccctgcaaagcggagttccttctagatttg gtggcagcggctccgggactgaattcactcttactattcctcccttcaacccgaagatttcgccacatattactgc cagcagcttaagtcatacccttcactttggcccaggaactaaagttgaaatcaaa (SEQ ID NO: 35) |
| | Nucleotide | cagatcaccctgagggagtctgaggcgacgtggtgcagcctggaaggagcctgagactgagctgcgccgcctctgg attcaccttcagcagctacgccatccactgggtcaggcaggctcctggcaagggactggagtgggtggccgttacctgg cacgacggcagcaacaagtactacgccgagagcgttatgggcaggttcaccatcagcagggacaacagcaagaacac cctgtacctgcacatgaactctctgagggccgaggacacaggcgtgtactactgcgccagggccaagttcggtgagccc cagtacttccagcactggggccagggaaccctggtgaccgtgtcttctggcggagggggatctggaggaggaagt ggaggcggtggcagcgacatcgtgatgacccagagccctagcttcctgtctgccagcgtgggagacagggtgaccatc acctgcagagccagcagggcatcaataactacctggcctggtaccagcagaagcccggcattgccccaagctcctg atctacgccgccagcaccctgcaaagcggcgtgccctctaggttcggcggatctggaagcggcaccgagttcaccctga ccattagcagcctgcagcccgaggacttcgccacctactactgccagcagctgaagagctaccccttcaccttcggccct ggcaccaaggtggagatcaag (SEQ ID NO: 51) |

In some embodiments, the polynucleotide encoding a BCMA targeting CAR polypeptide comprises a nucleic acid sequence that encodes a DAP10 costimulatory domain having the sequence of SEQ ID NO: 24. In some embodiments, the nucleic acid sequence encoding the DAP10 costimulatory domain is codon optimized. As a non-limiting example, the codon-optimized DAP10 costimulatory domain encoding sequence comprises the sequence of SEQ ID NO: 57. In some embodiments, the nucleic acid sequence encoding the DAP10 costimulatory domain comprises the sequence of SEQ ID NO: 39.

In some embodiments, the polynucleotide encoding a BCMA targeting CAR polypeptide comprises a nucleic acid sequence that encodes a CD28 hinge domain having the sequence of SEQ ID NO: 21. In other embodiments, the nucleic acid sequence encoding the CD28 hinge domain is codon optimized. As a non-limiting example, the codon-optimized CD28 hinge domain encoding sequence comprises the sequence of SEQ ID NO: 37, or SEQ ID NO: 54. In other embodiments, the polynucleotide encoding a BCMA targeting CAR polypeptide comprises a nucleic acid sequence encoding a CD28 hinge domain having the sequence of SEQ ID NO: 61; the nucleic acid sequence encoding the CD28 hinge domain is codon optimized. As a non-limiting example, the codon-optimized CD28 hinge domain coding sequence comprises the sequence of SEQ ID NO: 62, or SEQ ID NO: 63.

An exemplary nucleic acid sequence for each of other components of the present BCMA targeting CAR is included in Table 2.

TABLE 2

Exemplary nucleic acid sequences of components of a BCMA targeting CAR

| Component | Sequence (5'-3') |
|---|---|
| 1st Signal peptide | atggaattcgggctgtcctggcttttcttggtcgcaattcttaagggcgtccaatgt (SEQ ID NO: 33)<br>atggagttcggcctgagctggctgttcctggtggccatcctgaagggcgtgcagtgc (SEQ ID NO: 34) |
| CD28 hinge | atcgaagttatgtatcctcctccttacctagacaatgagaagagcaatggaaccattatccatgtgaaagggaaac<br>acctttgtccaagtcccctatttcccggaccttctaagccc (SEQ ID NO: 31)<br>cgggcggccgcaattgaagttatgtatcctcctccttacctagacaatgagaagagcaatggaaccattatccatg<br>tgaaagggaaacacctttgtccaagtcccctatttcccggaccttctaagcccaaagatcccaaa (SEQ ID NO: 37)<br>agggcgccgccattgaggtgatgtacccccccccctacctggacaacgagaagagcaacggcaccatcatcca<br>cgtgaagggcaagcacctctgccctagcccctgttccctggacccagcaagcccaaggaccccaag (SEQ ID NO: 54)<br>attgaagttatgtatcctcctccttacctagacaatgagaagagcaatggaaccattatccatgtgaaagggaaac<br>acctttgtccaagtcccctatttcccggaccttctaagccc (SEQ ID NO: 62)<br>Attgaggtgatgtacccccccccctacctggacaacgagaagagcaacggcaccatcatcacgtgaagggcaa<br>gcacctctgccctagccccctgttccctggacccagcaagccc (SEQ ID NO: 63) |
| CD28 transmembrane | ttttgggtgctggtggtggttggtggagtcctggcttgctatagcttgctagtaacagtggcctttattattttct<br>gggtg (SEQ ID NO: 38)<br>ttctgggtgctggtcgtggtgggaggcgttctggcctgctacagcctgctggtgacagtggcctttatcatcttct<br>gggtc (SEQ ID NO: 56) |
| DAP10 costimulatory domain | ctttgcgcacgccacgccgcagccccgcccaagaagatggcaaagtctacatcaacatgccaggcagggc (SEQ ID NO: 39)<br>ctgtgcgccagacctaggagaagcccccgcccaggaagacggaaaggtctacatcaacatgcccggaagggga (SEQ ID NO: 57) |
| CD3zeta signaling domain | cgcgtgaagttcagcaggagcgcagacgcccccgcgtaccagcagggccagaaccagctctataacgagctca<br>atctaggacgaagagaggagtacgatgtttttggacaaaagacgtggccgggacccctgagatgggggaaagcc<br>gagaaggaagaaccctcaggaaggcctgtacaatgaactgcagaaagataagatggcggaggcctacagtgag<br>attgggatgaaaggcgagcgccggaggggcaaggggcacgatggcctttaccagggtctcagtacagccacca<br>aggacacctacgacgcccttcacatgcaggccctgccccctcgc (SEQ ID NO: 40)<br>agggtcaagttcagccggtctgctgatgctcccgcctaccagcaaggccaaaaccagctgtacaacgagctgaac<br>ctgggcaggagagaagagtacgacgtgctggacaagaggagaggcagggacccccgagatgggaggcaagcc<br>cagaaggaagaaccccaggagggcctgtacaatgagctgcagaaggacaagatggccgaggcctacagcga<br>gatcggcatgaagggcgagagaagaagggcaaggccacgacggattgtaccagggcctgagcaccgctac<br>caaggacacctacgacgccctgcatatgcaagctctgcctcctagg (SEQ ID NO: 58) |
| CD28 costimulatory domain | aggagtaagaggagcaggctcctgcacagtgactacatgaacatgactccccgccgccccgggcccacccgca<br>agcattaccagcccatgcccaccacgcgacttcgcagcctatcgctca (SEQ ID NO: 41) |
| E2A linker | ggaccgcagtgtactaattatgctctcttgaaattggctggagatgttgagagcaatcccgggccc (SEQ ID NO: 11)<br>ggccctcagtgcaccaactacgccctgctcaagctggctggcgacgtcgagagcaaccccggaccc (SEQ ID NO: 12) |
| 2nd signal peptide | ggaccgcagtgtactaattatgctctcttgaaattggctggagatgttgagagcaatcccgggccc (SEQ ID NO: 42)<br>ggccctcagtgcaccaactacgccctgctcaagctggctggcgacgtcgagagcaaccccggaccc (SEQ ID NO: 43) |
| IL-15 | atgcgcattagcaagcccacctgcggagcatcagcatccagtgctacctgtgcctgctgctgaacagccacttcc<br>tgaccgaggccggcatccacgtgttcatcctgggctgcttcagcgccggactgcccaagaccgaggccaactggg<br>tgaacgtgatcagcgacctgaagaagatcgaggacctgatccagagcatgcacatcgacgccaccctgtacaccg<br>agagcgacgtgcacccagctgcaaggtgaccgccatgaagtgctttctgctggaactgcaggtgatcagcctgg<br>aaagcggcgacgccagcatccacgacaccgtggagaacctgatcatcctggccaacaacagcctgagcagcaa<br>cggcaacgtgaccgagagcggctgcaaagagtgcgaggaactggaagagaagaacatcaaagagtttctgcag<br>agcttcgtgcacatcgtgcagatgttcatcaacaccagc (SEQ ID NO: 52)<br>atgaggatcagcaagcctcacctgaggagcattagcatccagtgctacctgtgcctgctcctgaactcccacttcc<br>tgaccgaggccggcatccacgtcttcatcctgggctgcttcagcgctggcctgcccaaaaccgaggccaactgggt<br>gaacgtgatcagcgacctcaagaagatcgaggacctgatccagagcatgcacatcgacgccaccctgtataccga<br>gagcgacgtgcacccagctgcaaggtgaccgccatgaagtgcttcctgctggagctgcaggtcatcagcctgga<br>gagcggcgatgccagcatccacgacaccgtggagaacctgatcatcctggccaacaacagcctgagcagcaac<br>gggaacgtgaccgagtccggctgcaaggagtgcgaggagctggaggagaagaacatcaaggagttcctgcagt<br>ccttcgtgcacatcgtgcagatgttcatcaacaccagc (SEQ ID NO: 53) |

An exemplary polynucleotide that encodes a BCMA targeting CAR comprising a DAP10 derived costimulatory domain comprises the nucleic acid sequence presented by SEQ ID NO: 44. In some embodiments, the polynucleotide encoding the BCMA targeting CAR polypeptide may comprise a nucleic acid sequence at least 75% identical to SEQ ID NO: 44. In some embodiments, the polynucleotide encoding the BCMA targeting CAR polypeptide may comprise a nucleic acid sequence at least 80% identical to SEQ ID NO: 44. In some embodiments, the polynucleotide encoding the BCMA targeting CAR polypeptide may comprise a nucleic acid sequence at least 85% identical to SEQ ID NO: 44. In some embodiments, the polynucleotide encoding the BCMA targeting CAR polypeptide may comprise a nucleic acid sequence at least 90% identical to SEQ ID NO: 44. In some embodiments, the polynucleotide encoding the BCMA targeting CAR polypeptide may comprise a nucleic acid sequence at least 91% identical to SEQ ID NO: 44. In some embodiments, the polynucleotide encoding the BCMA targeting CAR polypeptide may comprise a nucleic acid sequence at least 92% identical to SEQ ID NO: 44. In some embodiments, the polynucleotide encoding the BCMA targeting CAR polypeptide may comprise a nucleic acid sequence at least 93% identical to SEQ ID NO: 44. In some embodiments, the polynucleotide encoding the BCMA targeting CAR polypeptide may comprise a nucleic acid sequence at least 94% identical to SEQ ID NO: 44. In some embodiments, the polynucleotide encoding the BCMA targeting CAR polypeptide may comprise a nucleic acid sequence at least 95% identical to SEQ ID NO: 44. In some embodiments, the polynucleotide encoding the BCMA targeting CAR polypeptide may comprise a nucleic acid sequence at least 96% identical to SEQ ID NO: 44. In some embodiments, the polynucleotide encoding the BCMA targeting CAR polypeptide may comprise a nucleic acid sequence at least 97%, identical to SEQ ID NO: 44. In some embodiments, the polynucleotide encoding the BCMA targeting CAR polypeptide may comprise a nucleic acid sequence at least 98% identical to SEQ ID NO: 44. In some embodiments, the polynucleotide encoding the BCMA targeting CAR polypeptide may comprise a nucleic acid sequence at least 99% identical to SEQ ID NO: 44.

The polynucleotide encoding the BCMA targeting CAR polypeptide may be codon-optimized.

In one embodiment, the polynucleotide encoding the BCMA targeting CAR polypeptide comprises the nucleic acid sequence of SEQ ID NO: 60. In some embodiments, the polynucleotide encoding the BCMA targeting CAR polypeptide may comprise a nucleic acid sequence at least 75% identical to SEQ ID NO: 60. In some embodiments, the polynucleotide encoding the BCMA targeting CAR polypeptide may comprise a nucleic acid sequence at least 80% identical to SEQ ID NO: 60. In some embodiments, the polynucleotide encoding the BCMA targeting CAR polypeptide may comprise a nucleic acid sequence at least 85% identical to SEQ ID NO: 60. In some embodiments, the polynucleotide encoding the BCMA targeting CAR polypeptide may comprise a nucleic acid sequence at least 90% identical to SEQ ID NO: 60. In some embodiments, the polynucleotide encoding the BCMA-CA targeting R polypeptide may comprise a nucleic acid sequence at least 91% identical to SEQ ID NO: 60. In some embodiments, the polynucleotide encoding the BCMA targeting CAR polypeptide may comprise a nucleic acid sequence at least 92% identical to SEQ ID NO: 60. In some embodiments, the polynucleotide encoding the BCMA targeting CAR polypeptide may comprise a nucleic acid sequence at least 93% identical to SEQ ID NO: 60. In some embodiments, the polynucleotide encoding the BCMA targeting CAR polypeptide may comprise a nucleic acid sequence at least 94% identical to SEQ ID NO: 60. In some embodiments, the polynucleotide encoding the BCMA targeting CAR polypeptide may comprise a nucleic acid sequence at least 95% identical to SEQ ID NO: 60. In some embodiments, the polynucleotide encoding the BCMA targeting CAR polypeptide may comprise a nucleic acid sequence at least 96% identical to SEQ ID NO: 60. In some embodiments, the polynucleotide encoding the BCMA targeting CAR polypeptide may comprise a nucleic acid sequence at least 97% identical to SEQ ID NO: 60. In some embodiments, the polynucleotide encoding the BCMA targeting CAR polypeptide may comprise a nucleic acid sequence at least 98% identical to SEQ ID NO: 60. In some embodiments, the polynucleotide encoding the BCMA targeting CAR polypeptide may comprise a nucleic acid sequence at least 99% identical to SEQ ID NO: 60.

In one embodiment, the polynucleotide encoding the BCMA targeting CAR polypeptide comprises the nucleic acid sequence of SEQ ID NO: 25. In some embodiments, the polynucleotide encoding the BCMA targeting CAR polypeptide may comprise a nucleic acid sequence at least 75% identical to SEQ ID NO: 25. In some embodiments, the polynucleotide encoding the BCMA targeting CAR polypeptide may comprise a nucleic acid sequence at least 80% identical to SEQ ID NO: 25. In some embodiments, the polynucleotide encoding the BCMA targeting CAR polypeptide may comprise a nucleic acid sequence at least 85% identical to SEQ ID NO: 25. In some embodiments, the polynucleotide encoding the BCMA targeting CAR polypeptide may comprise a nucleic acid sequence at least 90% identical to SEQ ID NO: 25. In some embodiments, the polynucleotide encoding the BCMA targeting CAR polypeptide may comprise a nucleic acid sequence at least 91% identical to SEQ ID NO: 25. In some embodiments, the polynucleotide encoding the BCMA targeting CAR polypeptide may comprise a nucleic acid sequence at least 92% identical to SEQ ID NO: 25. In some embodiments, the polynucleotide encoding the BCMA targeting CAR polypeptide may comprise a nucleic acid sequence at least 93% identical to SEQ ID NO: 25. In some embodiments, the polynucleotide encoding the BCMA targeting CAR polypeptide may comprise a nucleic acid sequence at least 94% identical to SEQ ID NO: 25. In some embodiments, the polynucleotide encoding the BCMA targeting CAR polypeptide may comprise a nucleic acid sequence at least 95% identical to SEQ ID NO: 25. In some embodiments, the polynucleotide encoding the BCMA targeting CAR polypeptide may comprise a nucleic acid sequence at least 96% identical to SEQ ID NO: 25. In some embodiments, the polynucleotide encoding the BCMA targeting CAR polypeptide may comprise a nucleic acid sequence at least 97% identical to SEQ ID NO: 25. In some embodiments, the polynucleotide encoding the BCMA targeting CAR polypeptide may comprise a nucleic acid sequence at least 98% identical to SEQ ID NO: 25. In some embodiments, the polynucleotide encoding the BCMA targeting CAR polypeptide may comprise a nucleic acid sequence at least 99% identical to SEQ ID NO: 25.

In one embodiment, the polynucleotide encoding the BCMA targeting CAR polypeptide comprises the nucleic acid sequence of SEQ ID NO: 55. In some embodiments, the polynucleotide encoding the BCMA targeting CAR polypeptide may comprise a nucleic acid sequence at least 75% identical to SEQ ID NO: 55. In some embodiments, the polynucleotide encoding the BCMA targeting CAR polypeptide may comprise a nucleic acid sequence at least 80% identical to SEQ ID NO: 55. In some embodiments, the polynucleotide encoding the BCMA targeting CAR polypeptide may comprise a nucleic acid sequence at least 85% identical to SEQ ID NO: 55. In some embodiments, the polynucleotide encoding the BCMA targeting CAR polypeptide may comprise a nucleic acid sequence at least 90% identical to SEQ ID NO: 55. In some embodiments, the polynucleotide encoding the BCMA targeting CAR polypeptide may comprise a nucleic acid sequence at least 91% identical to SEQ ID NO: 55. In some embodiments, the polynucleotide encoding the BCMA targeting CAR polypeptide may comprise a nucleic acid sequence at least 92% identical to SEQ ID NO: 55. In some embodiments, the polynucleotide encoding the BCMA targeting CAR polypeptide may comprise a nucleic acid sequence at least 93% identical to SEQ ID NO: 55. In some embodiments, the polynucleotide encoding the BCMA targeting CAR polypeptide may comprise a nucleic acid sequence at least 94% identical to SEQ ID NO: 55. In some embodiments, the polynucleotide encoding the BCMA targeting CAR polypeptide may comprise a nucleic acid sequence at least 95% identical to SEQ ID NO: 55. In some embodiments, the polynucleotide encoding the BCMA targeting CAR polypeptide may comprise a nucleic acid sequence at least 96% identical to SEQ ID NO: 55. In some embodiments, the polynucleotide encoding the BCMA targeting CAR polypeptide may comprise a nucleic acid sequence at least 97% identical to SEQ ID NO: 55. In some embodiments, the polynucleotide encoding the BCMA targeting CAR polypeptide may comprise a nucleic acid sequence at least 98% identical to SEQ ID NO: 55. In some embodiments, the polynucleotide encoding the BCMA targeting CAR polypeptide may comprise a nucleic acid sequence at least 99% identical to SEQ ID NO: 55.

TABLE 3

Exemplary nucleic acid sequences encoding the BCMA targeting DAP10 CAR polypeptide BCMA-DAP10 CAR polynucleotides
cagataactctgcgcgagtcaggaggagacgtggtgcaaccgggcagatctctcaggctttcatgtgccgccagtggcttcacatttag
ctcttatgcaatacattgggtcaggcaggctcctggcaagggcttggaatgggtagcggttacctggcatgatggatctaacaaatactac
gccgagtctgttatgggtcgattcacaatttctcgagacaattcaaaaaacacactctacctgcatatgaactcacttagagcagaggaca
ctggtgtctattactgcgccagagcaaaattcggcgagccacagtatttccagcactggggacaaggaaccctcgtaacagtatctagtg
ggggcggagggtctggaggagggggagcggggaggcggctctgatattgttatgacccaatcaccatcttttctgagcgctagtgt
cggcgacagggttacaatcacatgccgagcaagccaaggaatcaaattatctcgcatggtatcaacaaaaaccaggtatcgccccg
aaacttcttatttacgcagcatcaaccctgcaaagcggagttccttctagatttggtggcagcggctccgggactgaattcactcttactattt
cctcccttcaacccgaagatttcgccacatattactgccagcagcttaagtcatacccttcacttttggcccaggaactaaagttgaaatca
aacgggcggccgcaattgaagttatgtatcctcctccttacctagacaatgagaagagcaatggaaccattatccatgtgaagggaaac
acctttgtccaagtcccctatttcccggaccttctaagcccaaagatcccaaattttgggtgctggtggtggttggtggagtcctggcttgct
atagcttgctagtaacagtggccttttattattttctgggtgctttgcgcacgcccacgccgcagccccgcccaagaagatggcaaagtcta
catcaacatgccaggcaggggccgcgtgaagttcagcaggagcgcagacgcccccgcgtaccagcagggccagaaccagctctat
aacgagctcaatctaggacgaagagaggagtacgatgttttggacaaaagacgtggccgggaccctgagatgggggaaagccgag
aaggaagaaccctcaggaaggcctgtacaatgaactgcagaaagataagatggcggaggcctacagtgagattgggatgaaaggcg
agcgccggagggcaagggccacgatggcctttaccagggtctcagtacagccaccaaggacacctacgacgcccttcacatgcag
gccctgccccctcgc (SEQ ID NO: 44)

cagatcaccctgagggagtctggaggcgacgtggtgcagcctggaaggagcctgagactgagctgcgccgcctctggattcaccttc
agcagctacgccatccactgggtcaggcaggctcctggcaagggactggagtgggtggccgttacctggcacgacgcagcaacaa
gtactacgccgagagcgttatgggcaggttcaccatcagcagggacaacagcaagaacaccctgtacctgcacatgaactctctgagg
gccgaggacacaggcgtgtactactgcgccagggccaagttcggtgagcccagtacttccagcactggggccagggaaccctggt
gaccgtgtcttctgtgcgagggggatctggaggaggagggaagtggaggcggtggcagcgacatcgtgatgacccagagcccctagct
tcctgtctgccagcgtgggagacagggtgaccatcacctgcagagccagccagggcatcaataactacctggcctggtaccagcaga
agcccggcattgcccccaagctcctgatctacgccgccagcacctgcaaagcggcgtgccctctaggttcggcggatctggaagcg
gcaccgagttcaccctgaccattagcagcctgcagcccgaggacttcgccacctactactgccagcagctgaagagctacccttcacc
ttcggccctggcaccaaggtggagatcaagaggcgcgccgccattgaggtgatgtaccccccccctacctggacaacgagaagag
caacggcaccatcatccacgtgaaggcaagcaccttctgccctctgttcctggaccccagcaagccaaggaccccaagtt
ctgggtgctggtcgtggtgggaggcgttctggcctgctacagcctgctggtgacagtggcctttatcatcttctgggtcctgtgcgccaga
cctaggagaagccccgcccaggaagacggaaaggtctacatcaacatgcccggaaggggaagggtcaagttcagccggtctgctga
tgctcccgcctaccagcaaggccaaaaccagctgtacaacgagctgaacctgggcaggagagaagagtacgacgtgctggacaaga
ggagaggcagggacccccgagatggaggcaagcccagaaggaagcccaggaggccctgtacaatgagctgcagaaggac
aagatggccgaggcctacagcgagatcggcatgaagggcgagagaagaaggggcaaggccacgacggattgtaccagggcctg
agcaccgctaccaaggacacctacgacgccctgcatatgcaagctctgcctcctagg (SEQ ID NO: 60)

atggagttcggcctgagctggctgttcctggtggccatcctgaagggcgtgcagtgccagatcaccctgagggagtctggaggcgacg
tggtgcagcctggaaggagcctgagactgagctgcgccgcctctggattcaccttcagcagctacgccatccactgggtcaggcaggc
tcctggcaagggactggagtgggtggccgttacctggcacgacgcagcaacaagtactacgccgagagcgttatgggcaggttcac
catcagcagggacaacagcaagaacaccctgtacctgcacatgaactctctgagggccgaggacacaggcgtgtactactgcgccag
ggccaagttcggtgagcccagtacttccagcactggggccagggaaccctggtgaccgtgtcttctgtgcgagggggatctggagg
aggaggaagtggaggcggtggcagcgacatcgtgatgacccagagcccctagcttcctgtctgccagcgtgggagacagggtgacca
tcacctgcagagccagccagggcatcaataactacctggcctggtaccagcagaagcccggcattgcccccaagctcctgatctacgc
cgccagcacctgcaaagcggcgtgccctctaggttcggcggatctggaagcggcaccgagttcaccctgaccattagcagcctgca
gcccgaggacttcgccacctactgccagcagctgaagagctacccttcacttcggccctggcaccaaggtggagatcaagagg
gccgccgccattgaggtgatgtaccccccccctacctggacaacgagaagagcaacggcaccatcatccacgtgaaggcaagca
cctctgccctagcccctgttcctggaccccagcaagcccaaggaccccaagttctgggtgctggtcgtggtgggaggcgttctggcct
gctacagcctgctggtgacagtggcctttatcatcttctgggtcctgtgcgccagacctaggagaagccccgcccaggaagacggaaa
ggtctacatcaacatgcccggaaggggaagggtcaagttcagccggtctgctgatgctcccgcctaccagcaaggccaaaaccagct
gtacaacgagctgaacctgggcaggagagaagagtacgacgtgctggacaagaggagaggcagggacccccgagatggaggcaa
gcccagaaggaagaaccccaggagggcctgtacaatgagctgcagaaggacaagatggccgaggcctacagcgagatcggcatg
aagggcgagagaagaaggggcaagggccacgacggattgtaccagggcctgagcaccgctaccaaggacacctacgacgcctg
catatgcaagctctgcctcctaggggccctcagtgcaccaactacgccctgctcaagctggctggcgactcgagagcaaccccggac
ccatgaggatcagcaagcctcacctgaggagcattagcatccagtgctacctgtgcctgctcctgaactcccacttcctgaccgaggcc

TABLE 3-continued

Exemplary nucleic acid sequences encoding the BCMA targeting DAP10 CAR polypeptide

```
ggcatccacgtcttcatcctgggctgcttcagcgctggcctgcccaaaaccgaggccaactgggtgaacgtgatcagcgacctcaaga
agatcgaggacctgatccagagcatgcacatcgacgccaccctgtataccgagagcgacgtgcaccccagctgcaaggtgaccgcc
atgaagtgcttcctgctggagctgcaggtcatcagcctggagagcggcgatgccagcatccacgacaccgtggagaacctgatcatcc
tggccaacaacagcctgagcagcaacgggaacgtgaccgagtccggctgcaaggagtgcgaggagctggaggagaagaacatca
aggagttcctgcagtccttcgtgcacatcgtgcagatgttcatcaacaccagctga (SEQ ID NO: 25)

atggaattcgggctgtcctggcttttcttggtcgcaattcttaagggcgtccaatgtcagataactctgcgcgagtcaggaggagacgtgg
tgcaaccgggcagatctctcaggctttcatgtgccgccagtggcttcacatttagctcttatgcaatacattgggtcaggcaggctcctggc
aagggcttggaatgggtagcggttacctggcatgatggatctaacaaatactacgccgagtctgttatgggtcgattcacaatttctcgag
acaattcaaaaaacacactctacctgcatatgaactcacttagagcagaggacactggtgtctattactgcgccagagcaaaattcggcg
agccacagtatttccagcactggggacaaggaaccctcgtaacagtatctagtgggggcggagggtctggaggagggggagcggg
ggaggcggctctgatattgttatgacccaatcaccatcttttctgagcgctagtgtcggcgacagggttacaatcacatgccgagcaagc
caaggaatcaacaattatctcgcatggtatcaacaaaaaccaggtatcgccccgaaacttcttatttacgcagcatcaaccctgcaaagcg
gagttccttctagatttggtggcagcggctccgggactgaattcactcttactatttcctcccttcaaccccgaagatttcgccacatattactg
ccagcagcttaagtcatacccctctcacttttggcccaggaactaaagttgaaatcaaacggggccgcaattgaagttatgtatcctcctc
cttacctagacaatgagaagagcaatggaaccattatccatgtgaaagggaaacacctttgtccaagtcccctatttcccggaccttctaa
gcccaaagatcccaaattttgggtgctggtggtggttggtggagtcctggcttgctatagcttgctagtaacagtggccttattattttctgg
gtgctttgcgcacgcccacgccgcagcccccgcccaagaagatggcaaagtctacatcaacatgccaggcaggggccgcgtgaagttc
agcaggagcgcagacgccccccgcgtaccagcagggccagaaccagctctataacgagctcaatctaggacgaagagaggagtacg
atgttttggacaaaagacgtggccgggaccctgagatggggggaaagccgagaaggaagaaccctcaggaaggcctgtacaatgaa
ctgcagaaagataagatggcggaggcctacagtgagattgggatgaaaggcgagcgccggaggggcaaggggcacgatggcttt
accagggtctcagtacagccaccaaggacacctacgacgcccttcacatgcaggcctgccccctcgcggaccgcagtgtactaatta
tgctctcttgaaattggctggagatgttgagagcaatcccgggcccatgcgcattagcaagccccacctgcggagcatcagcatccagt
gctacctgtgcctgctgctgaacagccacttcctgaccgaggccggcatccacgtgttcatcctgggctgcttcagcgccggactgcc
aagaccgaggccaactgggtgaacgtgatcagcgacctgaagaagatcgaggacctgatccagagcatgcacatcgacgccaccct
gtacaccgagagcgacgtgcacccagctgcaaggtgaccgccatgaagtgctttctgctggaactgcaggtgatcagcctggaaag
cggcgacgccagcatccacgacaccgtggagaacctgatcatcctggccaacaacagcctgagcagcaacggcaacgtgaccgag
agcggctgcaaagagtgcgaggaactggaagagaagaacatcaaagagtttctgcagagcttcgtgcacatcgtgcagatgttcatca
acaccagctga (SEQ ID NO: 55)
```

In some embodiments, the polynucleotide comprises at least one modified nucleotide. In other embodiments, the polynucleotide comprises unmodified nucleotides only.

The polynucleotide encoding the CAR polypeptide of the present invention can be obtained using recombinant methods known in the art, for example by screening libraries from cells expressing the CAR construct, by deriving the CAR construct from a vector known to include the same, or by isolating directly from cells and tissues containing the same, using standard techniques. Alternatively, the polynucleotide can be produced synthetically in vitro.

In alternative embodiments, the polynucleotide sequence encoding various components of a BCMA targeting CAR can be disposed on the different nucleic acid molecules, e.g., different plasmids or vectors, e.g., viral vector, e.g., lentiviral vector. For example, the (i) sequence encoding an antigen binding domain can be present on a first nucleic acid, e.g., a first vector, and the (ii) sequence encoding an intracellular signaling domain can be present on the second nucleic acid, e.g., the second vector.

In some embodiments, the polynucleotide encoding the present CAR is a mRNA molecule. The mRNA may further comprise a poly (A) sequence, e.g., a sequence encompassing 50-5000, 100-5000, 50-2000, 100-2000, 50-1000, or 100-1000 adenines.

Cells

In one aspect, the invention provides a cell genetically engineered to express a BCMA targeting CAR polypeptide described herein. The cell may be a stem cell or an immune effector cell, or mixture thereof. An "immune effector cell," is any cell of the immune system that has one or more effector functions (e.g, cytotoxic cell killing activity, secretion of cytokines, induction of ADCC and/or CDC). Specific immune cells include but are not limited to, natural killer (NK) cell, T cell, gamma delta T cell, alpha beta T cell, invariant NKT (iNKT) cell, B cell, macrophage, mesenchymal stromal cell, dendritic cell, or a mixture thereof. In one embodiment, the immune effector cell is T cell. In another embodiment, the immune effector cell is NK cell.

As used herein, the term "genetically engineered" or "genetically modified" refers to the addition of extra genetic material in the form of DNA or RNA, such as DNA or RNA encoding a BCMA targeting CAR polypeptide of the present invention, into the total genetic material in a cell. The terms, "genetically modified cells," "modified cells," and "cells that are genetically engineered or modified to express," are used interchangeably.

In some embodiments, the immune effector cell (e.g., T cell or NK cell) is transformed with the polynucleotide encoding the CAR construct and the CAR is expressed on the cell surface. The CART cell or CAR-NK cell exhibits an antitumor property.

Methods for making the immune effector cells that express a CAR contemplated herein are provided. In one embodiment, the method comprises transfecting or transducing immune effector cells isolated from an individual such that the immune effector cells express one or more CARs contemplated herein. In certain embodiments, the immune effector cells are isolated from an individual and genetically modified without further manipulation in vitro. Such cells can then be directly readministered into the individual. In further embodiments, the immune effector cells are first activated and stimulated to proliferate in vitro prior to being genetically modified to express a CAR. In this regard, the immune effector cells may be cultured before and/or after being genetically modified (i.e., transduced or transfected to express a BCMA targeting CAR contemplated herein).

For example, the immune effector cell (e.g., T cell or NK cell) is transduced with a viral vector encoding a BCMA targeting CAR polypeptide of the present invention. The viral vector is a retroviral vector, such as a lentiviral vector and an AAV vector. In other examples, the immune effector cell (e.g., T cell or NK cell) is transfected with a nucleic acid molecule, e.g., mRNA, cDNA, DNA, encoding a BCMA targeting CAR polypeptide of the present invention.

Sources of Cells

In accordance with the present invention, the immune effector cells (e.g., T cells and NK cells) are obtained from a subject for expansion and genetic modification to express the CAR polypeptide of the present invention.

Immune effector cells can be autologous/autogeneic ("self") or non-autologous ("non-self", e.g., allogeneic, syngeneic or xenogeneic). "Autologous", as used herein, refers to cells from the same subject. "Allogeneic", as used herein, refers to cells of the same species that differ genetically to the cell in comparison. "Syngeneic", as used herein, refers to cells of a different subject that are genetically identical to the cell in comparison. "Xenogeneic", as used herein, refers to cells of a different species to the cell in comparison. In preferred embodiments, the cells are autologous.

In some embodiments, immune effector cells engineered to expressing a BCMA targeting CAR contemplated herein are T cells (also called T lymphocytes). T cells can be immature T cells, mature T cells, resting T cells, or activated T cells, T helper (Th) cells (e.g., T helper 1 (Th1) or T helper 2 (Th2) cells), or any other subset of T cells. Other illustrative populations of T cells suitable for use in particular embodiments include naive T cells (TN), T memory stem cells (TSCM), central memory T cells (TCM), effector memory T cells (TEM), and effector T cells (TEFF). T cells can be obtained from a number of sources, including peripheral blood mononuclear cells, bone marrow, lymph node tissue, cord blood, thymus tissue, tissue from a site of infection, ascites, pleural effusion, and spleen tissue. In some embodiments, T cells can be obtained from a unit of blood collected from a subject using any number of techniques known to the skilled artisan. For example, T cells are isolated from peripheral blood lymphocytes by lysing the red blood cells and depleting the monocytes.

In some embodiments, immune effector cells include NK cells. NK cells may be derived from cord blood, peripheral blood, induced pluripotent stem cells, hematopoietic stem cells, bone marrow. The NK cell may be derived from a cord blood mononuclear cell. The NK cell may be a CD56+NK cell.

In some embodiments, any immune effector cell (e.g., T cell or NK cell) lines available in the art, may be used. For example, NK cells may be derived from the NK-92 cell line.

In some embodiments, cells transduced with a polynucleotide encoding the BCMA targeting CAR as described herein are expanded. In some embodiments, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days).

In some embodiments, the cells are expanded in an appropriate media that includes one or more interleukin that result in at least a 100 fold, at least a 150 fold, at least a 200-fold (e.g., 200-fold, 250-fold, 300-fold, 350-fold) increase in cells over a 14 day expansion period, e.g., as measured by a method such as flow cytometry.

In some embodiments, a population of modified immune effector cells for the treatment of cancer comprises a BCMA targeting CAR contemplated herein. For example, a population of modified immune effector cells are a population of T cells and/or a population of NK cells.

Pharmaceutical Compositions and Formulations

In accordance with the present invention, compositions comprising BCMA targeting CARs, nucleic acid molecules encoding the same, cells expressing BCMA targeting CARs are provided. The compositions contemplated herein may comprise one or more BCMA targeting CAR polypeptides, polynucleotides, vectors comprising same, or genetically modified immune effector cells, etc., as contemplated herein. Compositions include, but are not limited to pharmaceutical compositions. The preparation of a pharmaceutical composition that comprises the compositions will be known to those of skill in the art in light of the present disclosure. In preferred embodiments, a composition comprises one or more cells modified to express one or more BCMA targeting CAR polypeptides as described herein. In some embodiments, pharmaceutical compositions comprising an effective amount of cells, compositions comprising immune effector cells (e.g., NK cells) as described herein are provided. In some embodiments, a pharmaceutical composition comprises a pharmaceutically acceptable carrier, diluent or excipient and cells expressing a BCMA targeting CAR polypeptide as contemplated herein.

The pharmaceutically acceptable carrier, diluent or excipient includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In particular embodiments, pharmaceutical compositions comprise an effective amount of CAR-expressing immune effector cells contemplated herein. As used herein, the term "an effective amount" refers to an amount effective of a genetically modified therapeutic cell, e.g., NK cell, to achieve a beneficial or desired prophylactic or therapeutic result, including clinical results (e.g., anti-cancer).

Pharmaceutical compositions comprising an immune effector cell population modified to express a BCMA targeting CAR of the present invention (e.g., NK cells) may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions are preferably formulated for parenteral administration, e.g., intravascular (intravenous or intraarterial), intraperitoneal or intramuscular administration.

The compositions may be liquid compositions. The liquid pharmaceutical compositions, whether they be solutions, suspensions or other like form, may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In some embodiments, the immune effector cells (e.g., NK cells) discussed herein, and compositions contemplated herein are formulated in a pharmaceutically acceptable cell culture medium. Such compositions are suitable for administration to human subjects. In particular embodiments, the pharmaceutically acceptable cell culture medium is a serum free medium. Serum-free medium has several advantages over serum containing medium, including a simplified and better-defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

In other embodiments, compositions comprising immune effector cells as described herein are formulated in a solution comprising a cryopreservation medium. For example, cryopreservation media with cryopreservation agents may be used to maintain a high cell viability outcome post-thaw. For example, compositions comprising immune effector cells as described herein may be cryopreserved in a medium discussed in the PCT application publication WO2022173866A1 (the contents of which are incorporated herein by reference in their entirety). In some embodiments, the cryopreservation medium comprises a non-pyrogenic and isotonic crystalloid solution, a disaccharide, a cryoprotectant and an albumin. In some embodiments, the non-pyrogenic and isotonic crystalloid solution is present at a concentration of 25% v/v to 50% v/v. In some embodiments, the non-pyrogenic and isotonic crystalloid solution is present at a concentration of about 25%, 30%, 35%, 40%, 45%, or 50%. In some embodiments, the non-pyrogenic and isotonic crystalloid solution is present at a concentration of 30% v/v to 40% v/v.

In some embodiments, the non-pyrogenic and isotonic crystalloid solution is present at a concentration of 37.1% v/v, 37.3% v/v, 37.5% v/v, 37.7% v/v, or 37.9% v/v.

In some embodiments, the non-pyrogenic and isotonic crystalloid solution is present at a concentration of 37.7% v/v.

In some embodiments, the non-pyrogenic and isotonic crystalloid solution is present at a concentration of 38.0% v/v, 38.2% v/v, 38.4% v/v, 38.6% v/v, 38.8% v/v, or 39.0% v/V.

In some embodiments, the non-pyrogenic and isotonic crystalloid solution is present at a concentration of 38.6% v/v.

In some embodiments, the disaccharide is selected from the group consisting of sucrose, lactose, maltose, trehalose, cellobiose, and chitobiose. Accordingly, in some embodiments, the disaccharide is sucrose. In some embodiments, the disaccharide is lactose. In some embodiments, the disaccharide is maltose. In some embodiments, the disaccharide is trehalose. In some embodiments, the disaccharide is cellobiose. In some embodiments, the disaccharide is chitobiose.

In some embodiments, a cryopreservation medium provided herein comprises one or more of sodium chloride, potassium chloride, magnesium chloride hexahydrate, sodium acetate trihydrate, sodium gluconate, adenosine, dextran-40, lactobionic acid, HEPES, sodium hydroxide, L-glutathione, potassium chloride, potassium bicarbonate; potassium phosphate, dextrose, sucrose, mannitol, calcium chloride dihydrate, magnesium chloride, sodium hydroxide, potassium hydroxide, DMSO, human serum albumin and trehalose.

In some embodiments, a cryopreservation medium provided herein comprises about 2.35% w/v human serum albumin (HSA). In some embodiments, the cryopreservation medium comprises between about 2.0% w/v and 5.0% w/v human serum albumin (HSA). In some embodiments, the cryopreservation medium comprises between about 2.0% w/v and 3.0% w/v human serum albumin (HSA). In some embodiments, a cryopreservation medium provided herein comprises about 1% v/v to 10% v/v human serum albumin (HSA). In some embodiments, a cryopreservation medium provided herein comprises about 5% v/v to 10% v/v human serum albumin (HSA). In some embodiments, the cryopreservation medium comprises 9.4% v/v human serum albumin.

In some embodiments, the cryopreservation medium comprises between about 10 mM-100 mM trehalose. In some embodiments, the cryopreservation medium comprises between about 10 mM-50 mM trehalose. In some embodiments, the cryopreservation medium comprises between about 20 mM-40 mM trehalose. In some embodiments, the cryopreservation medium comprises about 30 mM trehalose.

In some embodiments, a cryopreservation medium is provided comprising: human serum albumin (HSA), sodium chloride, sodium gluconate, sodium acetate trihydrate, potassium chloride, magnesium chloride, dimethyl sulfoxide (DMSO), and a trehalose.

In some embodiments, a cryopreservation medium is provided, the medium comprising: a non-pyrogenic and isotonic crystalloid solution, a cryoprotectant, an albumin, and a disaccharide. In some embodiments, a cryopreservation medium is provided, the medium comprising: PLASMA-LYTE A, a cryoprotectant, human serum albumin (HSA), and trehalose. In some embodiments, the cryoprotectant is DMSO. In some embodiments, a cryopreservation medium is provided, the medium comprising 37.7% PLASMA-LYTE A, 50% DMSO, 2.35% w/v HSA and 30 mM trehalose.

In some embodiments, the effector cells modified to express a BCMA targeting CAR polypeptide described herein are formulated in a balanced crystalloid solution such as Plasma-Lyte. In some embodiments, the effector cells are formulated in Plasma-Lyte A. In some embodiments, the concentration of Plasma-Lyte A is 20-60%. In some embodiments, the concentration of Plasma-Lyte A is 40%. In some embodiments, the effector cells are further formulated in a stabilizing agent such as serum albumin. In exemplary embodiments, the serum albumin is human serum albumin (HSA) at a concentration of 5% to 20%. In some embodiments, the concentration of HSA is 10%. In some embodiments, the effector cells are further formulated in a stabilizing agent such as trehalose. In exemplary embodiments, the concentration of trehalose is 5 mM to 50 mM. In some embodiments, the concentration of trehalose is 30 mM. In some embodiments, the effector cells are formulated in a cryofreezing medium. In some embodiments, the cryofreezing medium is CS10. In some embodiments, the concentration of CS10 is 40% to 60%. In some embodiments, the concentration of CS10 is 50%.

As a non-limiting example, the cryofreezing medium is composed of 50% CS10, 40% (v/v) Plasma-Lyte A, 10% HSA and 30 mM Trehalose dihydrate.

In some embodiments, compositions comprise an effective amount of immune effector cells modified to express a BCMA targeting CAR polypeptide described herein, alone or in combination with one or more therapeutic agents. Thus, the CAR-expressing immune effector cell compositions may be administered alone or in combination with other known cancer treatments, such as radiation therapy, chemotherapy, transplantation, immunotherapy, hormone therapy, photodynamic therapy, etc.

Packages and Kits

Any of the compositions described herein may be comprised in a package and/or a kit for clinical use. In a non-limiting example, cells, reagents to produce cells, vectors, and reagents to produce vectors and/or components thereof may be comprised in a kit. In certain embodiments, NK cells may be comprised in a kit, and they may or may not yet express a BCMA targeting CAR comprising a DAP10 costimulatory domain, an optional cytokine, or an optional suicide gene. Such a kit may or may not have one or more reagents for manipulation of cells. Such reagents include small molecules, proteins, nucleic acids, antibodies, buffers, primers, nucleotides, salts, and/or a combination thereof, for example. Nucleotides that encode one or more CARs, suicide gene products, and/or cytokines may be included in the kit. Proteins, such as cytokines or antibodies, including monoclonal antibodies, may be included in the kit. Nucleotides that encode components of engineered CAR receptors may be included in the kit, including reagents to generate same Methods of Use In another aspect of the present invention, methods, among other things, of use of BCMA targeting CARs, cells and compositions comprising the same are provided.

The BCMA targeting CARs, and genetically modified immune effector cells expressing a BCMA targeting CAR contemplated herein provide improved methods of adoptive immunotherapy for use in the prevention, treatment, and amelioration of B cell related conditions. The BCMA targeting CARs, and genetically modified immune effector cells expressing a BCMA targeting CAR described herein, provide improved methods of immunotherapy for use in increasing the cytotoxicity in cancer cells in a subject or for use in decreasing the number of cancer cells in a subject.

In some embodiments, a type of cellular therapy where T cells or NK cells are genetically modified to express the present CAR polypeptide that targets BCMA expressing cancer cells, and the T cells and/or the NK cells are infused to a recipient in need thereof is provided. The infused cell is able to kill disease causing cells, e.g., tumor cells, in the recipient. T cells and NK cells that express the present BCMA targeting CAR can undergo robust in vivo cell expansion and can persist for an extended amount of time.

In some embodiments, methods of treating a cancer such as a BCMA associated cancer in a subject in need are provided; the methods involve in administering to the subject in need a therapeutically effective amount of compositions as described in the present disclosure. The therapeutically effective amount of the composition comprising a genetically modified therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects.

In accordance with the present invention, it can generally be stated that a pharmaceutical composition comprising the immune effector cells (e.g., NK cells) contemplated herein may be administered at a dosage of $10^4$ to $10^{10}$ cells/kg body weight, or $10^6$ to $10^8$ cells/kg body weight, preferably $10^5$ to $10^6$ cells/kg body weight, including all integer values within those ranges. For example, in some embodiments, the pharmaceutical composition comprising the NK cells may be administered at a dosage of $1\times10^8$ cells. In some embodiments, the pharmaceutical composition comprising the NK cells may be administered at a dosage of $2\times10^8$ cells. In some embodiments, the pharmaceutical composition comprising the NK cells may be administered at a dosage of $3\times10^8$ cells. In some embodiments, the pharmaceutical composition comprising the NK cells may be administered at a dosage of $4\times10^8$ cells. In some embodiments, the pharmaceutical composition comprising the NK cells may be administered at a dosage of $5\times10^8$ cells. In some embodiments, the pharmaceutical composition comprising the NK cells may be administered at a dosage of $6\times10^8$ cells. In some embodiments, the pharmaceutical composition comprising the NK cells may be administered at a dosage of $7\times10^8$ cells. In some embodiments, the pharmaceutical composition comprising the NK cells may be administered at a dosage of $8\times10^8$ cells. In some embodiments, the pharmaceutical composition comprising the NK cells may be administered at a dosage of $9\times10^8$ cells. In some embodiments, the pharmaceutical composition comprising the NK cells may be administered at a dosage of $1.0\times10^9$ cells. In some embodiments, the pharmaceutical composition comprising the NK cells may be administered at a dosage of $1.1\times10^9$ cells. In some embodiments, the pharmaceutical composition comprising the NK cells may be administered at a dosage of $1.2\times10^9$ cells. In some embodiments, the pharmaceutical composition comprising the NK cells may be administered at a dosage of $1.3\times10^9$ cells. In some embodiments, the pharmaceutical composition comprising the NK cells may be administered at a dosage of $1.4\times10^9$ cells. In some embodiments, the pharmaceutical composition comprising the NK cells may be administered at a dosage of $1.5\times10^9$ cells. In some embodiments, the pharmaceutical composition comprising the NK cells may be administered at a dosage of $1.6\times10^9$ cells. In some embodiments, the pharmaceutical composition comprising the NK cells may be administered at a dosage of $1.7\times10^9$ cells. In some embodiments, the pharmaceutical composition comprising the NK cells may be administered at a dosage of $1.8\times10^9$ cells. In some embodiments, the pharmaceutical composition comprising the NK cells may be administered at a dosage of $1.9\times10^9$ cells. In some embodiments, the pharmaceutical composition comprising the NK cells may be administered at a dosage of $2.0\times10^9$ cells. The number of cells will depend upon the ultimate use for which the composition is intended as will the type of cells included therein. For uses provided herein, the cells are generally in a volume of a liter or less, 950 mL or less, 900 mL or less, 850 mL or less, 800 mL or less, 750 mL or less, 700 mL or less, 650 mL or less, 600 mL or less, 500 mL or less, even 250 mL or 100 mL or less. Hence the density of the desired cells is typically greater than $10^6$ cells/ml and generally is greater than $10^7$ cells/ml, generally $10^8$ cells/ml, generally $10^9$ or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects, particularly since all the infused cells will be redirected to a particular target antigen, lower numbers of cells, in the range of $10^6$-$10^9$/kilogram (e.g., about $6\times10^7$-$6\times10^{10}$ per patient) may be administered. Compositions may be administered multiple times at dosages within these ranges.

In some embodiments, the immune effector cells, e.g, T cells that express a BCMA targeting CAR of the present invention, are administered to a subject in need at a dose of at least $0.1\times10^5$ cells, at least $0.5\times10^5$ cells, at least $1\times10^5$ cells, at least $5\times10^5$ cells, at least $1\times10^6$ cells, at least $0.5\times10^7$ cells, at least $1\times10^7$ cells, at least $0.5\times10^8$ cells, at least $1\times10^8$ cells, at least $0.5\times10^9$ cells, at least $1\times10^9$ cells, at least $2\times10^9$ cells, at least $3\times10^9$ cells, at least $4\times10^9$ cells, at least $5\times10^9$ cells, or at least $1\times10^{10}$ cells.

In some embodiments, the immune effector cells, e.g, NK cells that express a BCMA targeting CAR of the present invention, are administered to a subject in need at a dose of at least $0.1\times10^5$ cells, at least $0.5\times10^5$ cells, at least $1\times10^5$ cells, at least $5\times10^5$ cells, at least $1\times10^6$ cells, at least $0.5\times10^7$ cells, at least $1\times10^7$ cells, at least $0.5\times10^8$ cells, at least $1\times10^8$ cells, at least $0.5\times10^9$ cells, at least $1\times10^9$ cells, at least $2\times10^9$ cells, at least $3\times10^9$ cells, at least $4\times10^9$ cells, at least $5\times10^9$ cells, or at least $1\times10^{10}$ cells.

As non-limiting examples, the NK cells engineered to express a BCMA targeting CAR of the present invention are administered at a dose of about $1\times10^6$ to $1\times10^{10}$, or about $5\times10^6$ to about $5\times10^9$, or about $1\times10^7$ to $3\times10^9$, or about $2\times10^7$ to $5\times10^8$, or about $4\times10^7$ to $1.0\times10^9$, or about $1\times10^8$ to $1.5\times10^9$ viable cells. In some embodiments, the NK cells engineered to express a BCMA targeting CAR described herein are administered at a dose of $1\times10^8$ viable cells, or at a dose of $5\times10^8$ viable cells, or at a dose of $1.5\times10^9$ viable cells.

In some embodiments, the amount of immune effector cells (e.g., T cells and NK cells) that express a BCMA targeting CAR of the present invention, are administered to a subject is at least $0.1\times10^4$ cells/kg of body weight, at least $0.5\times10^4$ cells/kg of body weight, at least $1\times10^4$ cells/kg of body weight, at least $5\times10^4$ cells/kg of body weight, at least $1\times10^5$ cells/kg of body weight, at least $0.5\times10^6$ cells/kg of body weight, at least $1\times10^6$ cells/kg of body weight, at least $1.5\times10^6$ cells/kg of body weight, at least $2.0\times10^6$ cells/kg of body weight, at least $3.0\times10^6$ cells/kg of body weight, at least $4.0\times10^6$ cells/kg of body weight, at least $5.0\times10^6$ cells/kg of body weight, at least $6.0\times10^6$ cells/kg of body weight, at least $7.0\times10^6$ cells/kg of body weight, $8.0\times10^6$ cells/kg of body weight, at least $9.0\times10^6$ cells/kg of body weight, at least $6.0\times10^6$ cells/kg of body weight, at least $7.0\times10^6$ cells/kg of body weight, $8.0\times10^6$ cells/kg of body weight or $9.0\times10^6$ cells/kg of body weight, at least $0.5\times10^7$ cells/kg of body weight, at least $1\times10^7$ cells/kg of body weight, at least $0.5\times10^8$ cells/kg of body weight, at least $1\times10^8$ cells/kg of body weight, at least $2\times10^8$ cells/kg of body weight, at least $3\times10^8$ cells/kg of body weight, at least $4\times10^8$ cells/kg of body weight, at least $5\times10^8$ cells/kg of body weight, at least $1\times10^9$ cells/kg, or at least $1\times10^{10}$ cells/kg of body weight. In some embodiments, the amount of immune effector cells (e.g., T cells and NK cells) that express a BCMA targeting CAR of the present invention, are administered to a subject is at least $1.5\times10^6$ cells/kg of body weight. In some embodiments, the amount of immune effector cells (e.g., T cells and NK cells) that express a BCMA targeting CAR of the present invention, are administered to a subject is at least $8.0\times10^6$ cells/kg of body weight. In some embodiments, the amount of immune effector cells (e.g., T cells and NK cells) that express a BCMA targeting CAR of the present invention, are administered to a subject is at least $2.5\times10^7$ cells/kg of body weight. In particular embodiments, about $1\times10^6$ NK cells/kg of body weight to about $1\times10^8$ NK cells/kg of body weight, about $2\times10^6$ NK cells/kg of body weight to about $0.9\times10^8$ NK cells/kg of body weight, about $3\times10^6$ NK cells/kg of body weight to about $0.8\times10^8$ NK cells/kg of body weight, about $4\times10^6$ NK cells/kg of body weight to about $0.7\times10^8$ NK cells/kg of body weight, about $5\times10^6$ NK cells/kg of body weight to about $0.6\times10^8$ NK cells/kg of body weight, or about $5\times10^6$ NK cells/kg of body weight to about $0.5\times10^8$ NK cells/kg of body weight are administered to a subject.

It is recognizable that multiple administrations of the compositions contemplated herein may be required to affect the desired therapy. For example, a composition may be administered 1, 2, 3, 4, 5, 6, 7, 8, 9, 10, or more times over a span of 1 week, 2 weeks, 3 weeks, 1 month, 2 months, 3 months, 4 months, 5 months, 6 months, 1 year, 2 years, 5 years, 10 years, or during the life time of a subject in need.

The administration of the present compositions may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection. As administration of the present compositions, intravenous is preferable.

Accordingly, the subject being administered to an effective amount of a composition increases a cellular immune response to a B cell related condition in the subject. The immune response may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced.

Therapeutic Applications

In some embodiments, BCMA targeting CAR polypeptides, cells comprising BCMA-CARs and compositions of the present invention may be used to treat a disease associated with expression of BCMA. The disease associated with expression of BCMA includes, but is not limited to, a disease associated with a cell which expresses BCMA (e.g., wild-type or mutant BCMA) or condition associated with a cell which expresses BCMA (e.g., wild-type or mutant BCMA) including, e.g., proliferative diseases such as a cancer or malignancy or a precancerous condition such as a myelodysplasia, a myelodysplastic syndrome or a preleukemia; or a noncancer related indication associated with a cell which expresses BCMA (e.g., wild-type or mutant BCMA). For example, a disease associated with expression of BCMA may include a condition associated with a cell which does not presently express BCMA, e.g., because BCMA expression has been downregulated, e.g., due to treatment with a molecule targeting BCMA, e.g., a BCMA inhibitor described herein, but which at one time expressed BCMA. In one aspect, a cancer associated with expression of BCMA (e.g., wild-type or mutant BCMA) is a hematological cancer. In one aspect, the hematological cancer is a leukemia or a lymphoma. In one aspect, a cancer associated with expression of BCMA (e.g., wild-type or mutant BCMA) is a malignancy of differentiated plasma B cells. In one aspect, a cancer associated with expression of BCMA (e.g., wild-type or mutant BCMA) includes cancers and malignancies including, but not limited to, e.g., one or more acute leukemias including but not limited to, e.g., B-cell acute Lymphoid Leukemia ("BALL"), T-cell acute Lymphoid Leukemia ("TALL"), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of BMCA (e.g., wild-type or mutant BCMA) comprise, but are not limited to, e.g., B cell prolymphocytic leukemia, blastic plasmacytoid dendritic cell neoplasm, Burkitt's lymphoma, diffuse large B cell lymphoma, Follicular lymphoma, Flairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like.

In some embodiments, the cancer is multiple myeloma, Hodgkin's lymphoma, non-Hodgkin's lymphoma, or glioblastoma. In embodiments, a disease associated with expression of BCMA includes a plasma cell proliferative disorder, e.g., asymptomatic myeloma (smoldering multiple myeloma or indolent myeloma), monoclonal gammapathy of undetermined significance (MGUS), Waldenstrom's macroglobulinemia, plasmacytomas (e.g., plasma cell dyscrasia, solitary myeloma, solitary plasmacytoma, extramedullary plasmacytoma, and multiple plasmacytoma), systemic amyloid light chain amyloidosis, and POEMS syndrome (also known as Crow-Fukase syndrome, Takatsuki disease, and PEP syndrome). Further diseases associated with expression of BCMA (e.g., wild-type or mutant BCMA) expression include, but not limited to, e.g., atypical and/or non-classical cancers, malignancies, precancerous conditions or proliferative diseases associated with expression of BCMA (e.g., wild-type or mutant BCMA), e.g., a cancer described herein, e.g., a prostate cancer (e.g., castrate-resistant or therapy-resistant prostate cancer, or metastatic prostate cancer), pancreatic cancer, or lung cancer.

In some embodiments, NK cells comprising the BCMA targeting CAR(s) and compositions of the present invention may be administered to a subject having multiple myeloma, who is anti-BCMA-naïve. In some embodiments, the NK cells comprising the BCMA targeting CAR(s) and compositions of the present invention may be administered to a subject having multiple myeloma who is previously received anti-BCMA therapy. In some embodiments, the NK cells comprising the BCMA targeting CAR(s) and compositions of the present invention may be administered to a subject having at least one prior multiple myeloma line of therapy. In some embodiments, the NK cells comprising the BCMA targeting CAR(s) and compositions of the present invention may be administered to a subject having at least 2 prior multiple myeloma lines of therapy. In some embodiments, the NK cells comprising the BCMA targeting CAR(s) and compositions of the present invention may be administered to a subject having at least 3 prior multiple myeloma lines of therapy. For example, the subject having multiple myeloma may be refractory to an immunomodulatory agent. For example, the subject having multiple myeloma may be refractory to a proteasome inhibitor. For example, the subject having multiple myeloma may be refractory to an anti-CD38 antibody. In some embodiments, the previous anti-BCMA therapy is therapy in which BCMA targeting chimeric antigen receptor (CAR) T cells, BCMA targeting antibody-drug-conjugates and/or BCMA targeting antibodies are administered to an individual. In one embodiment, the previous anti-BCMA therapy is BCMA targeting chimeric antigen receptor (CAR) T therapy.

Non-cancer related conditions that are associated with BCMA (e.g., wild-type or mutant BCMA) include viral infections; e.g., HIV, fungal infections, e.g., C. neof ormans, autoimmune disease; e.g. rheumatoid arthritis, system lupus erythematosus (SLE or lupus), pemphigus vulgaris, and Sjogren's syndrome; inflammatory bowel disease, ulcerative colitis; transplant-related allospecific immunity disorders related to mucosal immunity; and unwanted immune responses towards biologics (e.g., Factor VIII) where humoral immunity is important. In embodiments, a non-cancer related indication associated with expression of BCMA includes but is not limited to, e.g., autoimmune disease, (e.g., lupus), inflammatory disorders (allergy and asthma) and transplantation.

Preferred cancers treated by the methods described herein include B cell malignancy, e.g., multiple myeloma, Hodgkin's lymphoma or non-Hodgkin's lymphoma. In some embodiments, the BCMA targeting CAR polypeptides, cells comprising BCMA-CARs and compositions of the present invention may be used to treat multiple myeloma. In some embodiments, the BCMA targeting CAR polypeptides, cells comprising BCMA-CARs and compositions of the present invention may be used to treat relapsed multiple myeloma. In some embodiments, the BCMA targeting CAR polypeptides, cells comprising BCMA-CARs and compositions of the present invention may be used to treat refractory multiple myeloma.

Combination Therapies

The BCMA targeting CAR and the immune effector cells expressing the same may be used in combination with other known agents and therapies. The BCMA targeting CAR therapy and the at least one additional therapeutic agent can be administered simultaneously, in the same or in separate compositions, or sequentially. For sequential administration, the CAR-expressing cells described herein can be administered first, and the additional agent can be administered second, or the order of administration can be reversed. The administrations may be in intervals ranging from concurrently to minutes to days to weeks to months.

In some embodiments, the additional therapy is the administration of side-effect limiting agents (e.g., agents intended to lessen the occurrence and/or severity of side effects of treatment, such as anti-nausea agents, etc.).

In some embodiments, the additional therapy may be another specific anti-cancer therapy such as radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, hormone therapy, oncolytic viruses, or a combination of the foregoing.

A wide variety of chemotherapeutic agents may be used in combination with the present composition. A "chemotherapeutic agent" is used to connote a compound or composition that is administered in the treatment of cancer.

Additional immunotherapies may be used in combination or in conjunction with composition and methods described herein. Exemplary immunotherapeutic agents may include antibodies, antibody-drug conjugates, cancer vaccines, immune effector cells and immune checkpoint inhibitors.

The present compositions and methods may be used in combination with surgery. Approximately 60% of persons with cancer will undergo surgery of some type, which includes preventative, diagnostic or staging, curative, and palliative surgery. After and/or before surgery, a patient in need may be treated immune effector cells.

In some embodiments, other agents may be used in combination with certain aspects of the present embodiments to improve the therapeutic efficacy of treatment. Exemplary therapeutic agents that can be combined with the present composition may include small molecule enzymatic inhibitors, anti-metastatic agents, cytokines, growth factors, steroids, NSAIDs, DMARDs, anti-inflammatories, chemotherapeutics, radiotherapeutics, therapeutic antibodies, or other active and ancillary agents.

In some embodiments, known agents and therapies may be administered prior to administration of the BCMA targeting CAR and the immune effector cells (e.g., NK cells) expressing the same. In some exemplary embodiments, lymphodepleting chemotherapy is administered prior to the BCMA targeting CAR therapy. Fludarabine is an exemplary lymphodepleting chemotherapy. Exemplary lymphodepleting agents are disclosed in WO2010046917A2, WO2003099007A1, among others, which are incorporated by reference in their entirety. Fludarabine phosphate typically is administered as a single dose of 25 mg/m$^2$-per day for 5, 4, 3, or 2 consecutive days. Dosages up to 30 mg/m$^2$-per day for 5, 4, 3, and/or 2 consecutive days also may be used. Fludarabine phosphate may be administered as a single dose of 25 mg/m$^2$-per day for 5 consecutive days before administration of the BCMA targeting CAR and the immune effector cells (e.g., NK cells) expressing the same. Fludarabine phosphate may be administered as a single dose of 25 mg/m$^2$-per day for 4 consecutive days before administration of the BCMA targeting CAR and the immune effector cells (e.g., NK cells) expressing the same. Fludarabine phosphate may be administered as a single dose of 25 mg/m$^2$-per day for 3 consecutive days before administration of the BCMA targeting CAR and the immune effector cells (e.g., NK cells) expressing the same.

In some embodiments, the subject is treated with cyclophosphamide prior to receiving the BCMA targeting CAR therapy. The subject may receive a single dose of cyclophosphamide at 300 mg/m2 BSA per day 5 days, 4 days or 3 days before on receiving the BCMA targeting CAR therapy. For example, the subject may receive a single dose of cyclophosphamide at 300 mg/m2 BSA per day 5 days, 4 days or 3 days before on receiving NK cells expressing an anti-BCMA CAR described herein.

EXAMPLES

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute certain modes for its practice. However, those of skill in the art should, in light of the present disclosure, appreciate that many changes can be made in the specific embodiments which are disclosed and still obtain a like or similar result without departing from the spirit and scope of the invention.

Example 1: Construct of Chimeric Antigen Receptor

This example shows the BMCA CAR construct used for reducing tumor burden. As illustrated in FIG. 1, the construct comprising nucleotide encoding BCMA DAP10 CAR comprising an anti-BCMA specific binder, a CD28 hinge, a CD28 transmembrane domain, a DAP10 costimulatory domain, and IL-15 cytokine (e.g., soluble IL-15), etc. was used in the Example 1 to 9. The amino acid sequences that expressed from the construct and the nucleic acid sequences encoding the amino acid sequences are described in the Table 4. These sequences were used in the Example 2 to 9.

TABLE 4

Sequences of BCMA targeting CAR constructs

BCMA-DAP10 CAR
MEFGLSWLFLVAILKGVQCQITLRESGGDVVQPGRSLRLSCAASGFTFSSYAIHWVRQAPGKG
LEWVAVTWHDGSNKYYAESVMGRFTISRDNSKNTLYLHMNSLRAEDTGVYYCARAKFGEPQ
YFQHWGQGTLVTVSSGGGGSGGGGSGGGGSDIVMTQSPSFLSASVGDRVTITCRASQGINNYL
AWYQQKPGIAPKLLIYAASTLQSGVPSRFGGSGSGTEFTLTISSLQPEDFATYYCQQLKSYPFTF
GPGTKVEIKRAAAIEVMYPPPYLDNEKSNGTIIHVKGKHLCPSPLFPGPSKPKDPKFWVLVVVG
GVLACYSLLVTVAFIIFWVLCARPRRSPAQEDGKVYINMPGRGRVKFSRSADAPAYQQGQNQ
LYNELNLGRREEYDVLDKRRGRDPEMGGKPRRKNPQEGLYNELQKDKMAEAYSEIGMKGER
RRGKGHDGLYQGLSTATKDTYDALHMQALPPRGPQCTNYALLKLAGDVESNPGPMRISKPHL
RSISIQCYLCLLLNSHFLTEAGIHVFILGCFSAGLPKTEANWVNVISDLKKIEDLIQSMHIDATLY
TESDVHPSCKVTAMKCFLLELQVISLESGDASIHDTVENLIILANNSLSSNGNVTESGCKECEEL
EEKNIKEFLQSFVHIVQMFINTS (SEQ ID NO: 29)

BCMA-DAP10 CAR nucleic acid
atggaattcgggctgtcctggcttttcttggtcgcaattcttaagggcgtccaatgtcagataactctgcgcgagtcaggaggagacgtggtgc
aaccgggcagatctctcaggctttcatgtgccgcagtggcttcacatttagctcttatgcaatacattgggtcaggcaggctcctggcaaggg
cttggaatgggtagcggttacctggcatgatggatctaacaaatactacgccgagtctgttatgggtcgattcacaatttctcgagacaattca
aaaaacacactctacctgcatatgaactcacttagagcagcaggacactggtgtctattactgcgccagagcaaaattcggcgagccacagtatt
tccagcactggggacaaggaaccctcgtaacagtatctagtggggcggagggtctggaggaggggggggggaggcggctctgatattgtta
tgacccaatcaccatctttctgagcgctagtgtcggcgacagggttacaatcacatgccgagcaagccaaggaatcaacaattatctcgcatg
gtatcaacaaaaaccaggtatcgccccgaaacttcttatttacgcagcatcaaccctgcaaagcggagttccttctagatttggtggcagcggc
tccgggactgaattcactcttactatttcctcccttcaacccgaagatttcgccacatattactgccagcagcttaagtcatacccccttcactt TABLE 4-continued Sequences of BCMA targeting CAR constructs

```
ttggcccaggaactaaagttgaaatcaaacgggcggccgcaatcgaagttatgtatcctcctccttacctagacaatgagaagagcaatggaac
cattatccatgtgaaagggaaacacctttgtccaagtcccctatttcccggaccttctaagcccaaagatcccaaattttgggtgctggtggtg
gttggtggagtcctggcttgctatagcttgctagtaacagtggcctttattattttctgggtgctttgcgcacgcccacgccgcagccccgccc
aagaagatggcaaagtctacatcaacatgccaggcaggggccgcgtgaagttcagcaggagcgcagacgcccccgcgtaccagcagggccagaa
ccagctctataacgagctcaatctaggacgaagagaggagtacgatgttttggacaaaagacgtggccgggaccctgagatgggggggaaagccg
agaaggaagaaccctcaggaaggcctgtacaatgaactgcagaaagataagatggcggaggcctacagtgagattgggatgaaaggcgagcgcc
ggaggggcaaggggcacgatggcctttaccagggtctcagtacagccgctacgacgcccttcacatgcaggccctgccccctcg
cggaccgcagtgtactaattatgctctcttgaaattggctggagatgttgagagcaatcccgggcccatgcgcattagcaagcccacctgcgg
agcatcagcatccagtgctacctgtgcctgctgctgaacagccacttcctgaccgaggccggcatccacgtgttcatcctgggctgcttcagcg
ccggactgcccaagaccgaggccaactgggtgaacgtgatcagcgacctgaagaagatcgaggacctgatccagagcatgcacatcgacgccac
cctgtacaccgagagcgacgtgcaccccagctgcaaggtgaccgccatgaagtgctttctgctggaactgcaggtgatcagcctggaaagcggc
gacgccagcatccacgacaccgtggagaacctgatcatcctggccaacaacagcctgagcagcaacggcaacgtgaccgagagcggctgcaaag
agtgcgaggaactggaagagaagaacatcaaagagtttctgcagagcttcgtgcacatcgtgcagatgttcatcaacaccagctga (SEQ
ID NO: 55)
```

BCMA-CD28 CAR
```
MEFGLSWLFLVAILKGVQCQITLRESGGDVVQPGRSLRLSCAASGFTFSSYAIHWVRQAPGKG
LEWVAVTWHDGSNKYYAESVMGRFTISRDNSKNTLYLHMNSLRAEDTGVYYCARAKFGEPQ
YFQHWGQGTLVTVSSGGGGSGGGGSGGGGSDIVMTQSPSFLSASVGDRVTITCRASQGINNYL
AWYQQKPGIAPKLLIYAASTLQSGVPSRFGGSGSGTEFTLTISSLQPEDFATYYCQQLKSYPFTF
GPGTKVEIKRAAAIEVMYPPPYLDNEKSNGTIIHVKGKHLCPSPLFPGPSKPKDPKFWVLVVVG
GVLACYSLLVTVAFIIFWVRSKRSRLLHSDYMNMTPRRPGPTRKHYQPYAPPRDFAAYRSRVK
FSRSADAPAYQQGQNQLYNELNLGRREEYDVLDKRRGRDPEMGGKPRRKNPQEGLYNELQK
DKMAEAYSEIGMKGERRRGKGHDGLYQGLSTATKDTYDALHMQALPPRGPQCTNYALLKLA
GDVESNPGPMRISKPHLRSISIQCYLCLLLNSHFLTEAGIHVFILGCFSAGLPKTEANWVNVISD
LKKIEDLIQSMHIDATLYTESDVHPSCKVTAMKCFLLELQVISLESGDASIHDTVENLIILANNS
LSSNGNVTESGCKECEELEEKNIKEFLQSFVHIVQMFINTS (SEQ ID NO: 45)
```

BCMA-CD28 CAR nucleic acid
```
atggaattcgggctgtcctggcttttcttggtcgcaattcttaagggcgtccaatgtcagataactctgcgcgagtcaggaggagacgtggtgc
aaccgggcagatctctcaggctttcatgtgccgcagtggcttcacatttagctcttatgcaatacattgggtcaggcaggctcctggcaaggg
cttggaatgggtagcggttacctggcatggatctaacaaatactacgccgagtctgttatgggtcgattcacaatttctcgagacaattca
aaaaacacactctacctgcatatgaactcacttagagcagaggacactggtgtctattactgcgccagagcaaaattcggcgagccacagtatt
tccagcactggggacaaggaaccctcgtaacagtatctagtgggggcggaggtctggaggaggggggagcggggggaggcggctctgatattgt
tatgacccaatcaccatcttttctgagcgctagtgtcggcgacagggttacaatcacatgccgagcaagccaaggaatcaacaattatctcgca
tggtatcaacaaaaaccaggtatcgccccgaaacttcttatttacgcagcatcaaccctgcaaagcggagttccttctagatttggtggcagcg
gctccgggactgaattcactcttactatttcctccctcaacccgaagatttcgccacatattactgccagcagcttaagtcatacccctttcac
ttttggcccaggaactaaagttgaaatcaaacgggcggccgcaattgaagttatgtatcctcctccttacctagacaatgagaagagcaatgga
accattatccatgtgaaagggaaacacctttgtccaagtcccctatttcccggaccttctaagcccaaagatcccaaattttgggtgctggtgg
tggttggtggagtcctggcttgctatagcttgctagtaacagtggccttttattattttctgggtgaggagtaagaggagcggctcctgcacag
tgactacatgaacatgactccccgccgccccgggccaccccgcaagcattaccagccctatgccccaccacgcgacttcgcagcctatcgctca
cgcgtgaagttcagcaggagcgcagacgccccgcgtaccagcagggccagaaccagctctataacgagctcaatctaggacgaagagaggagt
acgatgttttggacaaaagacgtggccgggaccctgagatgggggaaagccgagaaggaagaaccctcaggaaggcctgtacaatgaactgca
gaaagataagatggcggaggcctacagtgagattgggatgaaaggcgagcgccggaggggcaagggcacgatggccttttaccagggtctcagt
acagccaccaaggacacctacgacgcccttcacatgcaggccctgccccctcgcgaccgcagtgtactaattatgctctcttgaaattggctg
gagatgttgagagcaatcccgggcccatgcgcattagcaagcccacctgcggagcatcagcatccagtgctacctgtgcctgctgctgaacag
ccacttcctgaccgaggccggcatccacgtgttcatcctgggctgcttcagcgccggactgcccaagaccgaggccaactgggtgaacgtgatc
agcgacctgaagaagatcgaggacctgatccagagcatgcacatcgacgccaccctgtacaccgagagcgacgtgcaccccagctgcaaggtga
ccgccatgaagtgctttctgctggaactgcaggtgatcagcctggaaagcggcgacgccagcatccacgacaccgtggagaacctgatcatcct
ggccaacaacagcctgagcagcaacggcaacgtgaccgagagcggctgcaaagagtgcgaggaactggaagagaagaacatcaaagagtttctg
cagagcttcgtgcacatcgtgcagatgttcatcaacaccagctga (SEQ ID NO: 46)
```

Example 2: In Vivo Efficacy of BCMA CAR Constructs Against MM1S Tumor

This Example shows the efficacy of BCMA-DAP10-CAR comprised in SEQ ID NO: 29 and BCMA-CD28-CAR comprised in SEQ ID NO: 45, expressed in CB-NK cells, against MM1S tumor.

10-12 week old female NSG mice were whole-body irradiated at 150 cGy 24 hours prior to tumor inoculation. MM. 1S-ffluc-MDA cells were prepared in PBS suspension at a concentration of 2.5×10^6 cells/ml, for intravenous inoculation of cells at 0.5×10^6/animal. Bioluminescent images were taken 1 day prior to dosing, 6 days after tumor inoculation, and animals were randomized based on total flux into groups of 4 animals per arm. Animals were dosed 7 days after tumor inoculation. The CAR expressing NK (i.e., CAR NK) cells in the relevant concentrations were resuspended in PBS and transferred to the vivarium on ice in small batches to ensure timely infusion into the animals while maintaining the CAR expressing NK cell viability. Bioluminescent images were carried out weekly on a Xenogen IVIS to monitor tumor progression. Body weights were taken three times a week, alongside clinical observations to monitor for any signs of toxicity. Microsampling (via sub-mandibular collection of blood) was carried out once a week for cellular kinetics analysis to quantify CAR NK expansion in vivo, either by ddPCR or flow cytometric analysis. At humane or study endpoint, necropsy of animals from studies of interest was carried out to obtain various tissues for tox/pathology assessment.

Figure 2A:
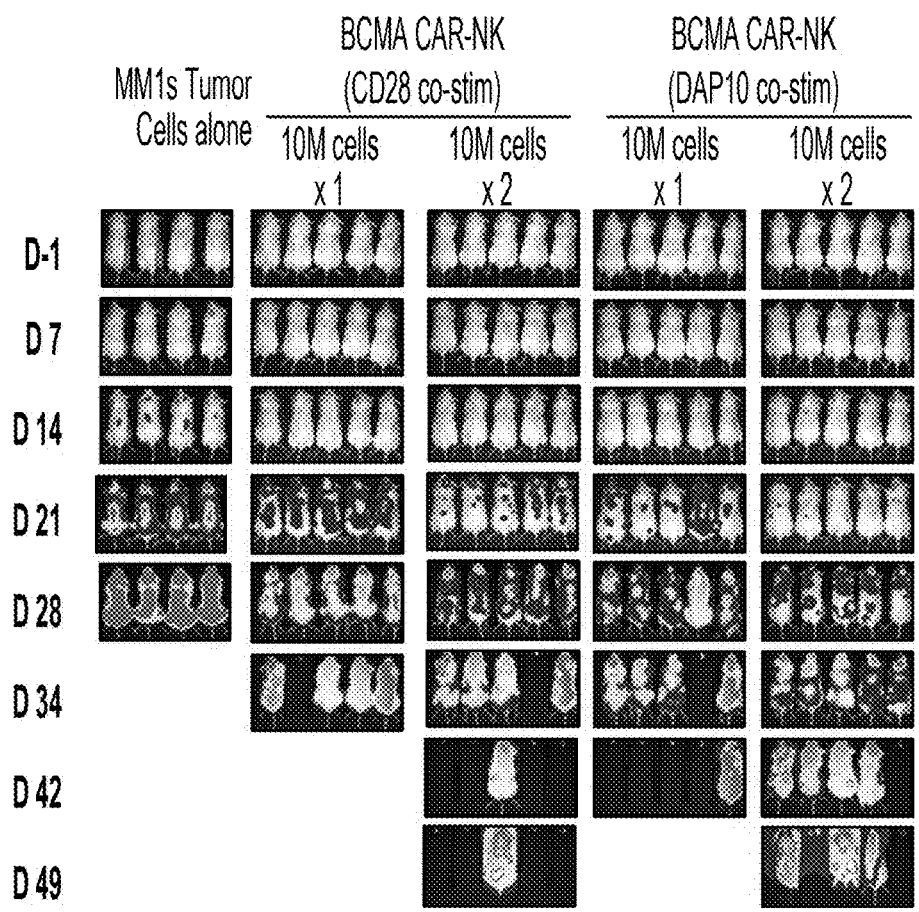
FIG. 2A shows the representative images of mice which were inoculated with tumor cells, after receiving one (10M×1) or two doses (10M×2) of BCMA-CAR expressing NK cells.
Figure 2B:
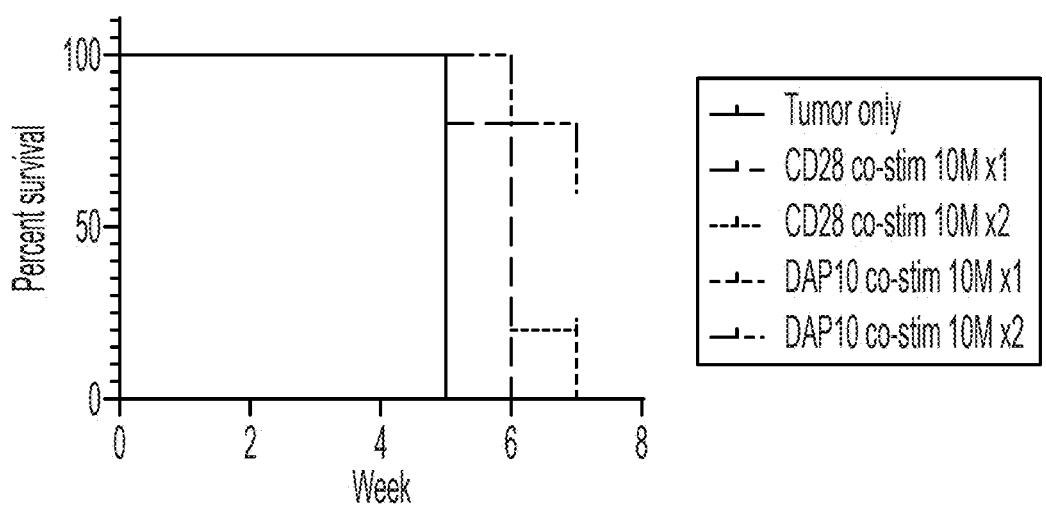
FIG. 2B demonstrates in vivo efficacy of BCMA-DAP10 and BCMA-CD28 CAR constructs against MM1S tumor.

For single dose of 10M the CAR expressing NK cells, both BCMA-DAP10-CAR and BCMA-CD28-CAR performed equivalently. For 2 doses of 10M the CAR expressing NK cells, BCMA-DAP10-CAR outperformed BCMA-CD28-CAR with 3 mice surviving to Day 49 compared to only one for BCMA-CD28.-CAR (FIG. 2A). All CAR transduced NK cells showed a benefit when compared to tumor alone (FIG. 2B).

CAR-NK Cell Manufacturing

For CAR-NK production, cord blood (CB) units for research were obtained from the MD Anderson Cancer Center Cord Blood Bank. CB mononuclear cells were isolated from frozen CB units by Ficoll density gradient centrifugation. Ex vivo expansion of cord-blood derived NK cells (CB-NK cells) used uAPC stimulation on Day 0 in addition to feeding IL-2 every 2 days. On Day 6, cells were transduced with RD114 virus using spinoculation. Cells were stimulated with a second round of uAPC addition on Day 8 or 9 and fed IL-2 every 2 days until they were used for in vivo or in vitro studies on Day 15 or cryopreserved on Day 21 for later use.

Example 3: In Vitro Efficacy of BCMA CAR Constructs Against Multiple Tumor Lines This Example shows the efficacy of BCMA-DAP10-CAR comprised in SEQ ID NO: 29 and BCMA-CD28-CAR comprised in SEQ ID NO: 45, expressed in CB-NK cells, against different tumor cells.

MM1S-Luc, RPMI-8226-Luc, JJN3-Luc and JJN3-Luc BCMA KO cells were washed with PBS once, cells were incubated with cell tracer deep red dye (Invitrogen #C34565) at 1:10,000 dilution in PBS at 37° C. for 20 minutes with the cell density at 2.5 million/ml. At the end of incubation, 20 ml cell culture medium were added to the cells and cells were spun down at 500 g for 5 minutes, supernatant was removed and cells were washed one more time using corresponding cell culture medium. Cells were then resuspended in culture medium at 0.25 million/ml, and 30 ul cells were added to each well of the v-bottom 384 well assay plates (Greiner, catalog: 781280). Cells were incubated at 37° C. cell culture incubator with 5% CO2 for 1-2 hours. Fresh effector cells were harvested at day 15 and cells were washed once in the cytokine free NK cell medium (CellGenix GMP SCGM with 10% HI-FBS and 2 mM Glutamine), 10 ul effector cells were then added to the assay plates at different E to T ratios. Target cells and effector wells were co-cultured for 20 hours, cells were then spun down and supernatant was collected for cytokine release assay. Cells were incubated with 10 ul caspase3/7 reagent (Intellicyt, catalog: 91035) diluted at 1:500 in corresponding target cell medium for 1 hour in cell culture incubator at 37° C. and then submitted for FACS analysis using either Sartorius iQue3 or Sartorius iQue screener Plus. The percentage of target cells with positive caspase 3/7 staining was used to report the cytotoxicity of effector cells.

Figure 3:
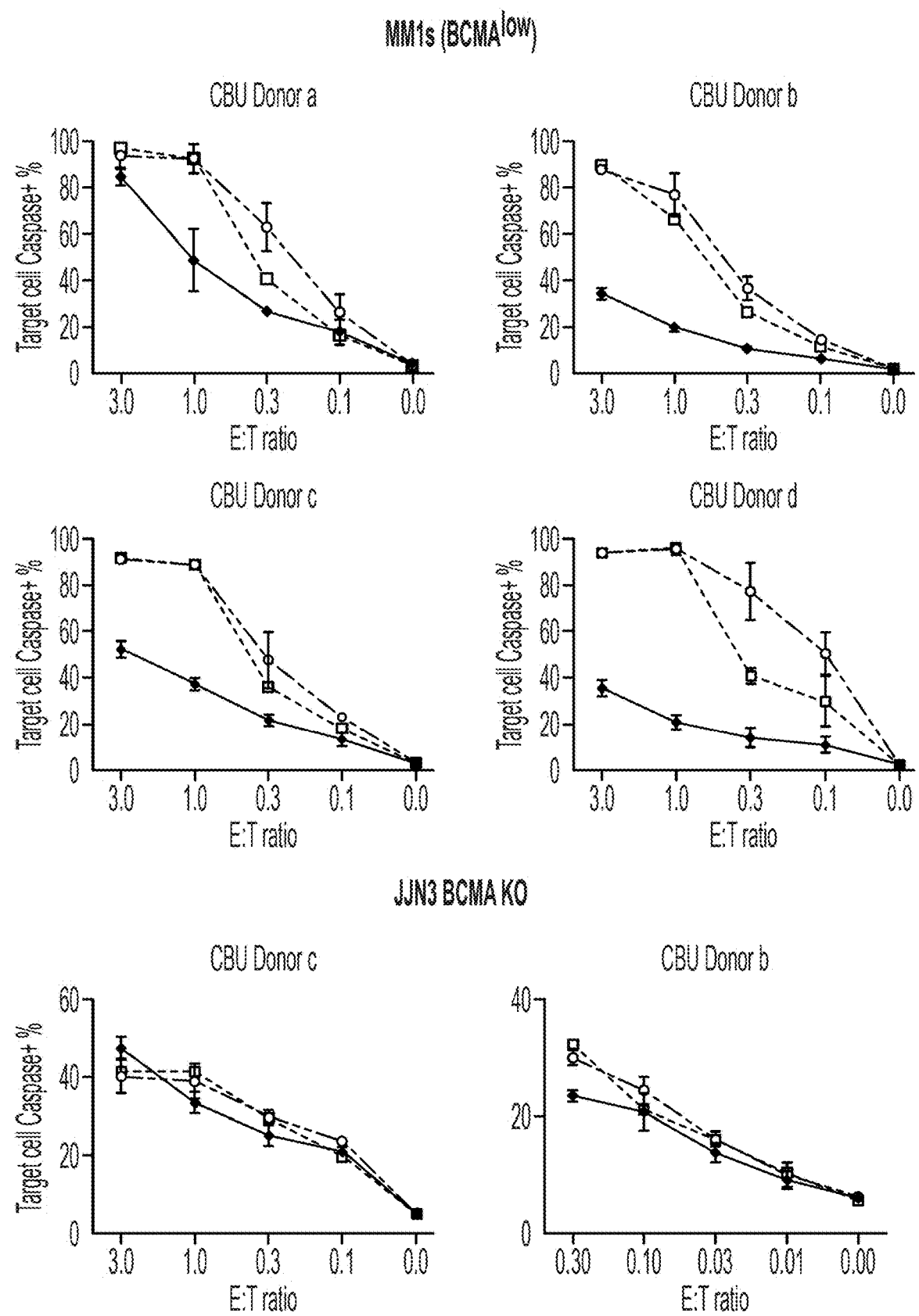
FIG. 3 shows in vivo efficacy of BCMA-DAP10 and BCMA-CD28 CAR constructs against multiple tumor cell lines.
Figure 3:
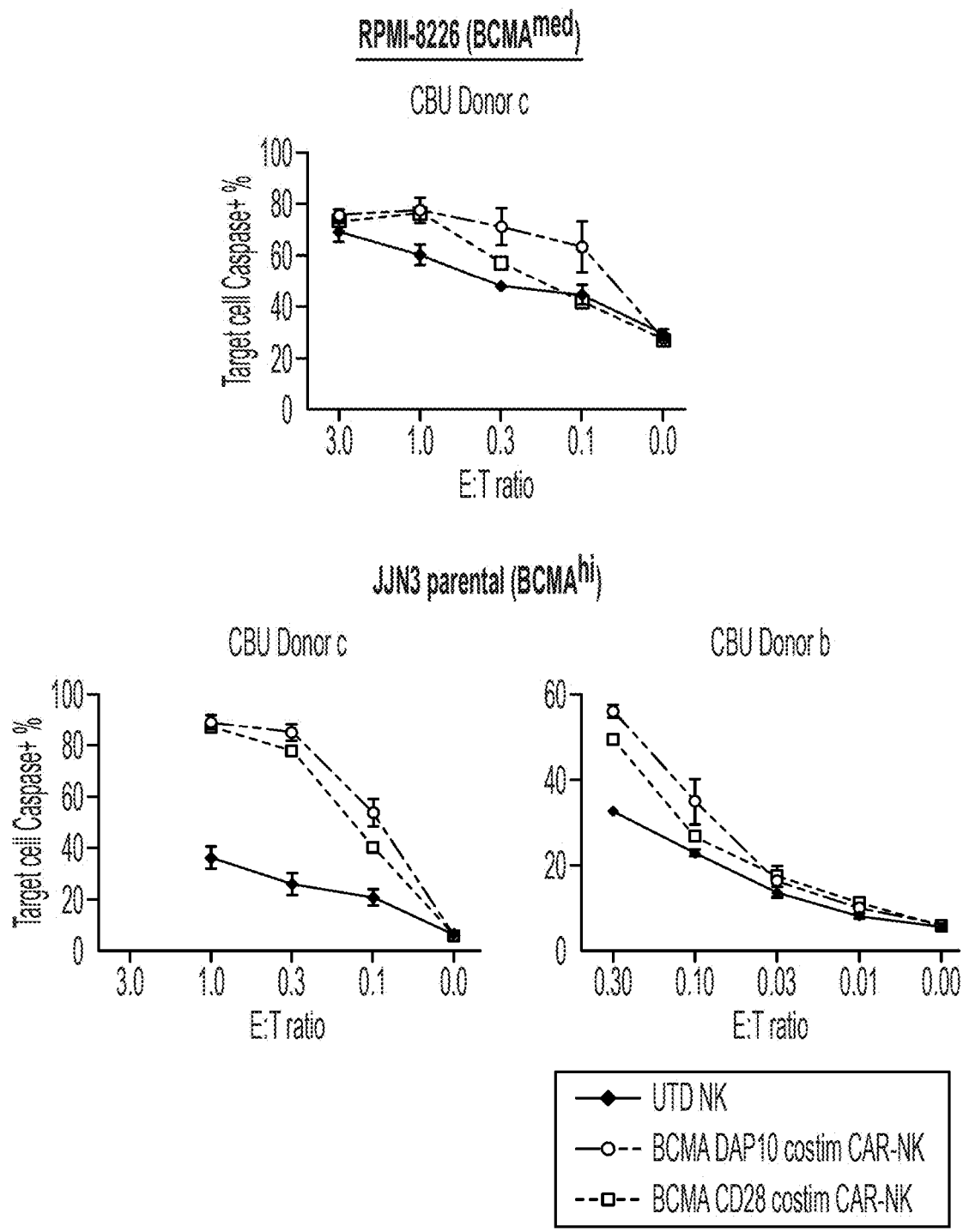

In vitro killing activity was superior overall in the BCMA-DAP10-CAR construct for multiple tumor cell lines (as shown in FIG. 3).

Example 4: Ability of BCMA CAR NK Cells to Kill Tumor Cells In Vitro with Multiple Rounds of Restimulation This Example shows the efficacy of BCMA-DAP10-CAR comprised in SEQ ID NO: 29 and BCMA-CD28-CAR comprised in SEQ ID NO: 45, expressed in CB-NK cells.

Figure 4A:
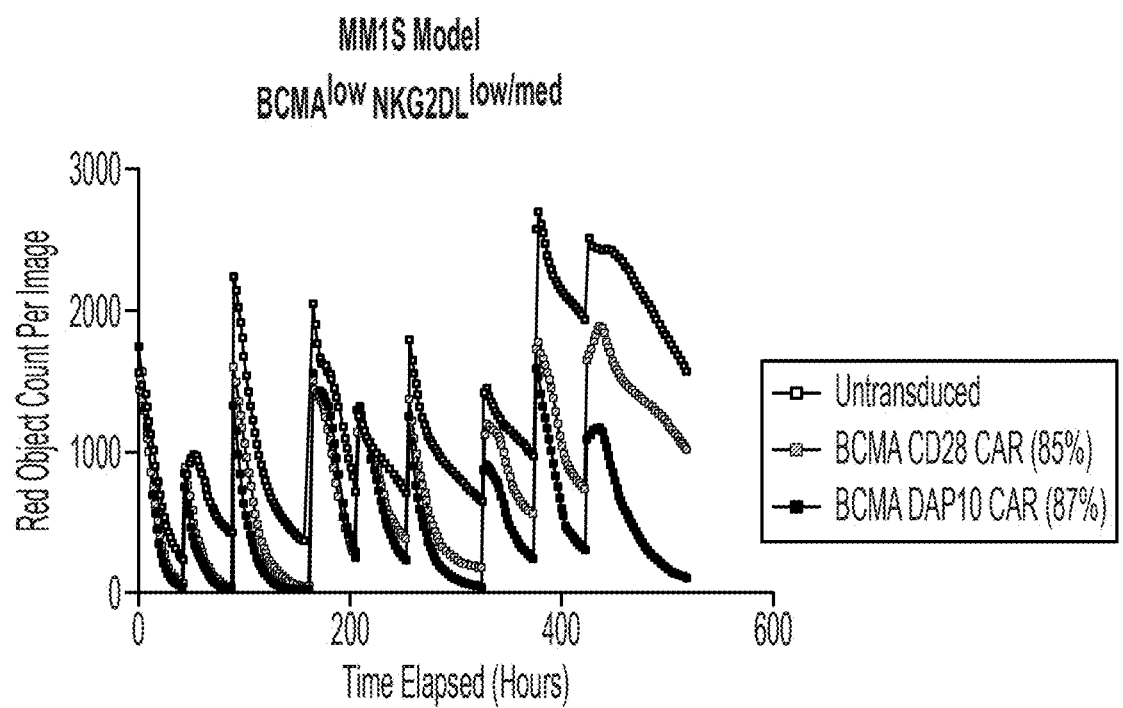
FIGS. 4A and 4B show the ability of BCMA-DAP10-CAR and BCMA-CD28-CAR NK cells to kill tumor cells in MM1S tumor model in vitro with multiple rounds of Restimulation.
Figure 4B:
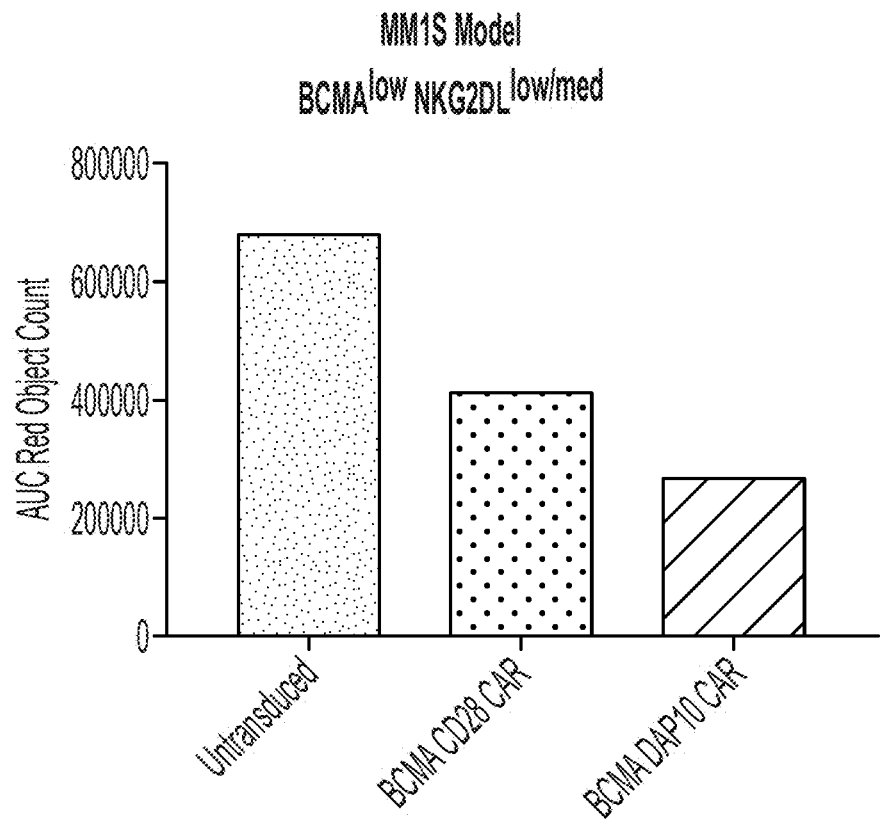
Figure 5A:
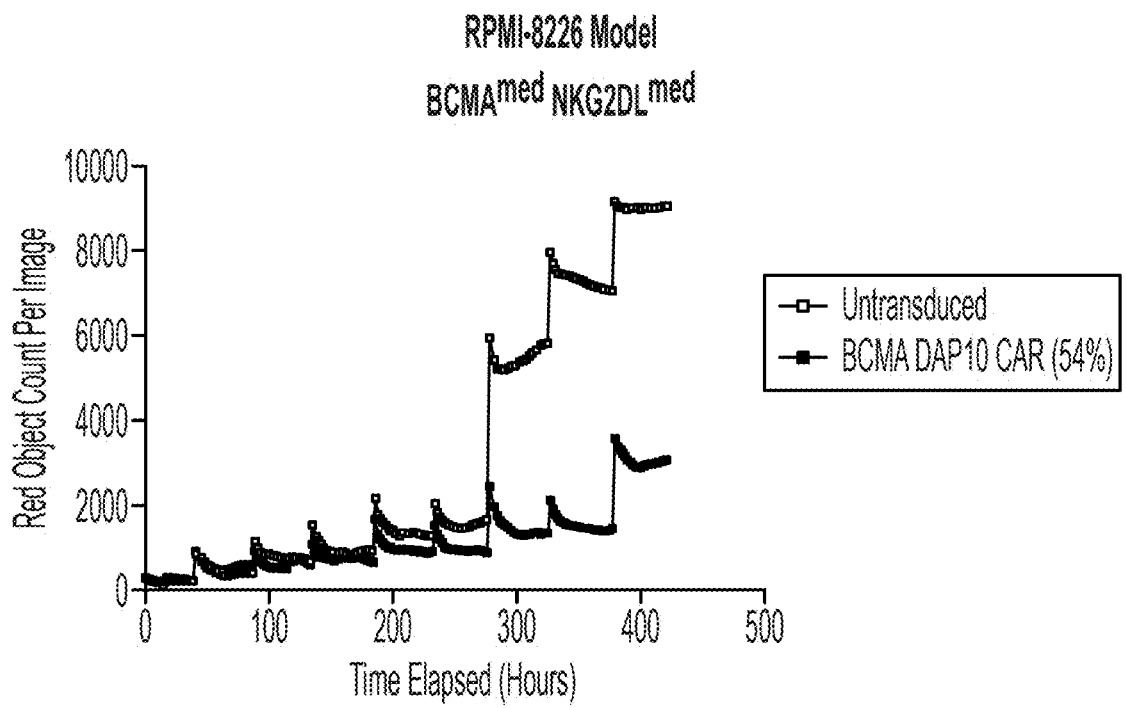
FIGS. 5A and 5B show the ability of BCMA-DAP10-CAR and BCMA-CD28-CAR NK cells to kill tumor cells in RPMI-8226 model in vitro with multiple rounds of Restimulation.
Figure 5B:
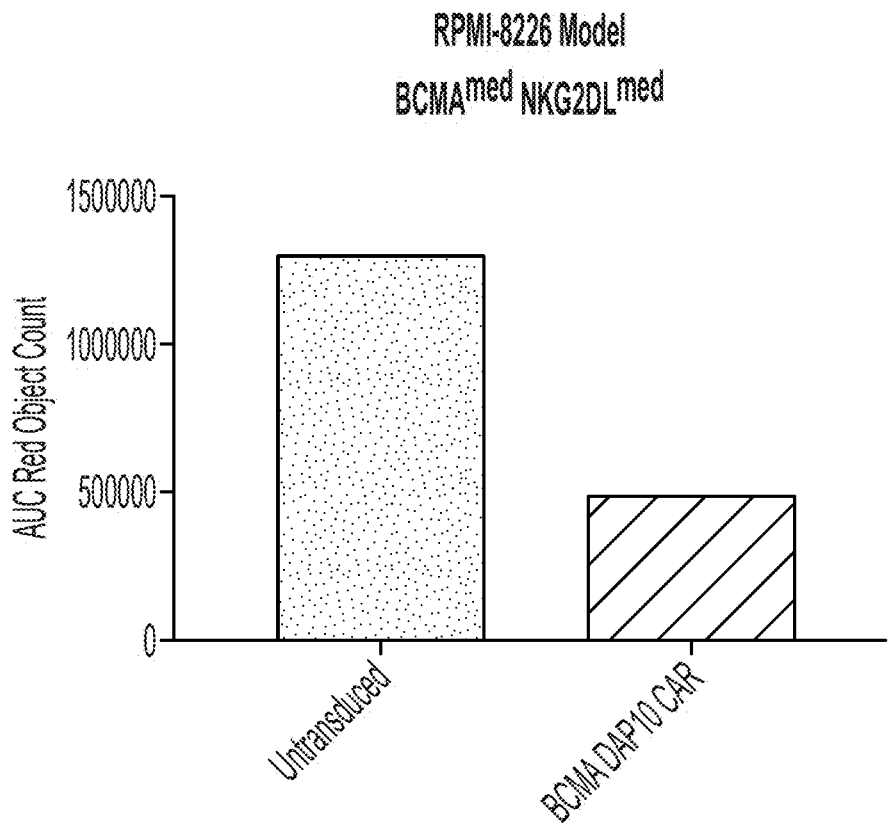

Effector cells were harvested and resuspended in SCGM (CellGenix, catalogue no.: 20802-0500) supplemented with 10% Heat Inactivated FBS (Sigma, catalogue no.: F4135-500 mL), 1% L-Glutamine (Gibco, catalogue no.: 25030-081), 1% Penn Strep (Gibco, catalogue no.: 15140-122) and 100 IU/mL Human IL-2 (Miltenyi, catalogue no.: 130-097-748). Effector cells were seeded in triplicate into a 48 well flat bottom non-tissue culture treated plate (Corning, catalogue no.: 3548) at a density of 2e5 cells/well (MM1S model, FIG. 4A, 4B) or 5e4 cells/well (RPMI-8226 model, FIG. 5A, 5B). Target cells previously transduced with NucLight Red Lentivirus (Sartorius, catalogue no.: 4476) and selected with 1 µg/mL puromycin (Sigma, catalogue no.: P8833-10 MG) were harvested and resuspended in the complete media described above and seeded at a density of 5e4 cells/well. Plates were placed in an IncuCyte S3 (Sartorius Inc.) and quadruplicate readings per well were measured in both the bright field and red channel using the 10× objective every 30 minutes. Target cells were prepared as described above and reseeded at a density of 5e4 cells/well every 48-72 hours (MM1S model, FIG. 4A, 4B) or every 48 hours (RPMI-8226, FIG. 5A, 5B) for a total of 9 tumor stimulations/rechallenges. Target cell cytolysis is represented as mean red object count per image (FIG. 4A, 4B) and total average area under the curve of the red object count (FIG. 5A, 5B).

BCMA-DAP10-CAR showed superior efficacy over the BCMA-CD28-CAR against repeated stimulation with MM1S and also showed outstanding control of RPMI-8226 tumor cells upon repeated stimulation.

Example 5: In Vivo Efficacy of BCMA CAR Constructs Against RPMI-8226 Tumor

This Example shows the in vivo efficacy of BCMA-DAP10-CAR comprised in SEQ ID NO: 29 and BCMA-CD28-CAR comprised in SEQ ID NO:45, in CB-NK cells, against RPMI-8226 tumor.

10-12 week old female NSG mice were whole-body irradiated at 150 cGy 24 hours prior to tumor inoculation. RPMI-8226-luc cells were prepared in PBS suspension at a concentration of 2.5×10^6 cells/ml, for intravenous inoculation of cells at 0.5×10^6/animal. Bioluminescent images were taken 1 day prior to dosing, 6 days after tumor inoculation, and animals were randomized based on total flux into groups of 4 animals per arm. Animals were dosed 7 days after tumor inoculation. The CAR expressing NK cells in the relevant concentrations were resuspended in PBS and transferred to the vivarium on ice in small batches to ensure timely infusion into the animals while maintaining the CAR expressing NK cell viability. Bioluminescent images were carried out weekly on a Xenogen IVIS to monitor tumor progression. Body weights were taken three times a week, alongside clinical observations to monitor for any signs of toxicity. Microsampling (via submandibular collection of blood) was carried out once a week for cellular kinetics analysis to quantify CAR NK expansion in vivo, either by ddPCR or flow cytometric analysis. At humane or study endpoint, necropsy of animals from studies of interest was carried out to obtain various tissues for tox/pathology assessment.

Figure 6:
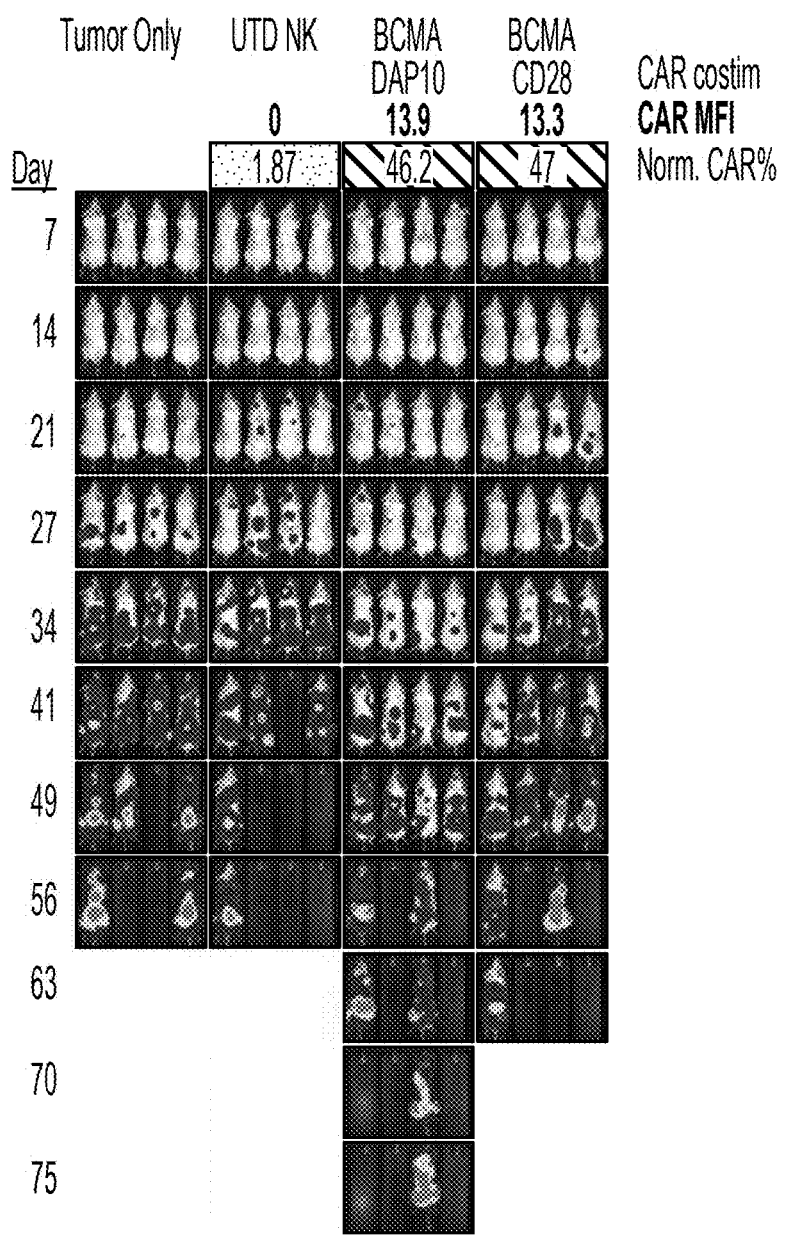
FIG. 6 shows in vivo efficacy of BCMA-DAP10 CAR and BCMA-CD28 CAR constructs against RPMI-8226 tumor.

BCMA-DAP10-CAR showed superior efficacy with twice as many mice surviving on Day 63 and one mouse surviving on Day 75, compared to all mice in controls succumbing to tumor growth by Day 63 (FIG. 6).

Example 6: In Vivo Expansion of BCMA CAR NK Cells in RPMI-8226 Tumor Model

This Example shows the expansion efficacy of CB-NK cells that are engineered to express BCMA-DAP10-CAR comprised in SEQ ID NO: 29 or BCMA-CD28-CAR comprised in SEQ ID NO: 45 in response to tumor in RPMI-8226 tumor model.

10-12 week old female NSG mice were whole-body irradiated at 150 cGy 24 hours prior to tumor inoculation. RPMI-8226-luc cells were prepared in PBS suspension at a concentration of 2.5×10^6 cells/ml, for intravenous inoculation of cells at 0.5×10^6/animal. Bioluminescent images were taken 1 day prior to dosing, 6 days after tumor inoculation, and animals were randomized based on total flux into groups of 4 animals per arm. Animals were dosed 7 days after tumor inoculation. CAR NK cells in the relevant concentrations were resuspended in PBS and transferred to the vivarium on ice in small batches to ensure timely infusion into the animals while maintaining CAR NK cell viability. Bioluminescent images were carried out weekly on a Xenogen IVIS to monitor tumor progression. Body weights were taken three times a week, alongside clinical observations to monitor for any signs of toxicity. Microsampling (via submandibular collection of blood) was carried out once a week for cellular kinetics analysis to quantify CAR NK expansion in vivo, either by ddPCR or flow cytometric analysis. At humane or study endpoint, necropsy of animals from studies of interest was carried out to obtain various tissues for tox/pathology assessment.

Figure 7:
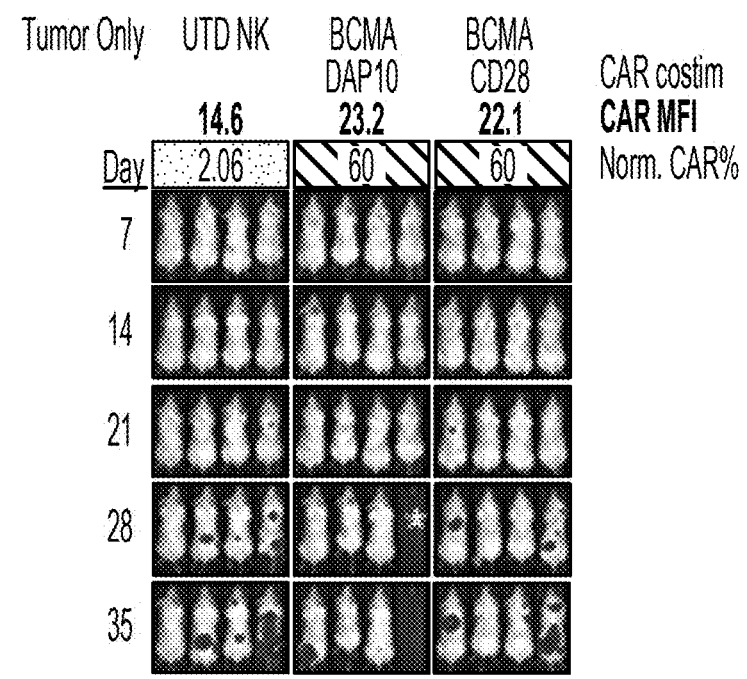
FIG. 7 shows in vivo expansion of BCMA-DAP10 CAR NK cells and BCMA-CD28 CAR NK cells in RPMI-8226 tumor model.
Figure 7:
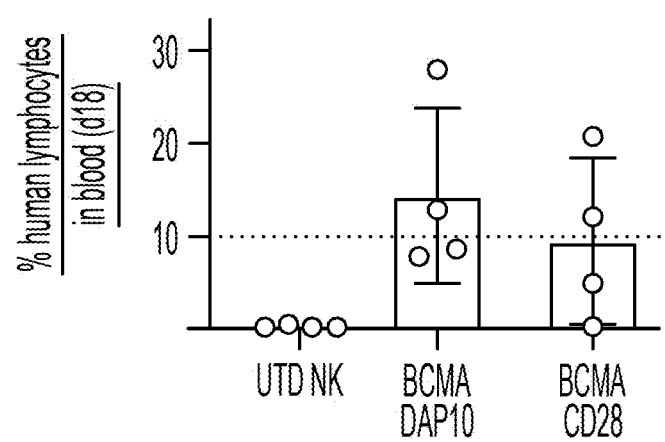

As shown in FIG. 7, NK cells expressing the BCMA-DAP10-CAR construct and NK cells expressing the BCMA-CD28-CAR construct both expand in vivo in response to RPMI-8226 tumor. Furthermore, NK cells expressing the BCMA-DAP10-CAR construct expand at a higher efficacy as compared to the expansion of NK cells expressing the BCMA-CD28-CAR construct (FIG. 7).

Example 7: In Vivo Efficacy of BCMA CAR in RPMI-8226 Tumor Model at Multiple Doses This Example shows the efficacy of BCMA-DAP10-CAR comprised in SEQ ID NO: 29 and expressed in CB-NK cells against RPMI-8226 tumor; the CAR expressing NK cells were administered at multiple doses.

10-12 week old female NSG mice were whole-body irradiated at 150 cGy 24 hours prior to tumor inoculation. RPMI-8226-luc cells were prepared in PBS suspension at a concentration of 2.5×10^6 cells/ml, for intravenous inoculation of cells at 0.5×10^6/animal. Bioluminescent images were taken 1 day prior to dosing, 6 days after tumor inoculation, and animals were randomized based on total flux into groups of 4 animals per arm. Animals were dosed 7 days after tumor inoculation. The CAR expressing NK cells in the relevant concentrations were resuspended in PBS and transferred to the vivarium on ice in small batches to ensure timely infusion into the animals while maintaining the CAR expressing NK cell viability. Bioluminescent images were carried out weekly on a Xenogen IVIS to monitor tumor progression. Body weights were taken three times a week, alongside clinical observations to monitor for any signs of toxicity. Microsampling (via submandibular collection of blood) was carried out once a week for cellular kinetics analysis to quantify CAR NK expansion in vivo, either by ddPCR or flow cytometric analysis. At humane or study endpoint, necropsy of animals from studies of interest was carried out to obtain various tissues for tox/pathology assessment.

Figure 8A:
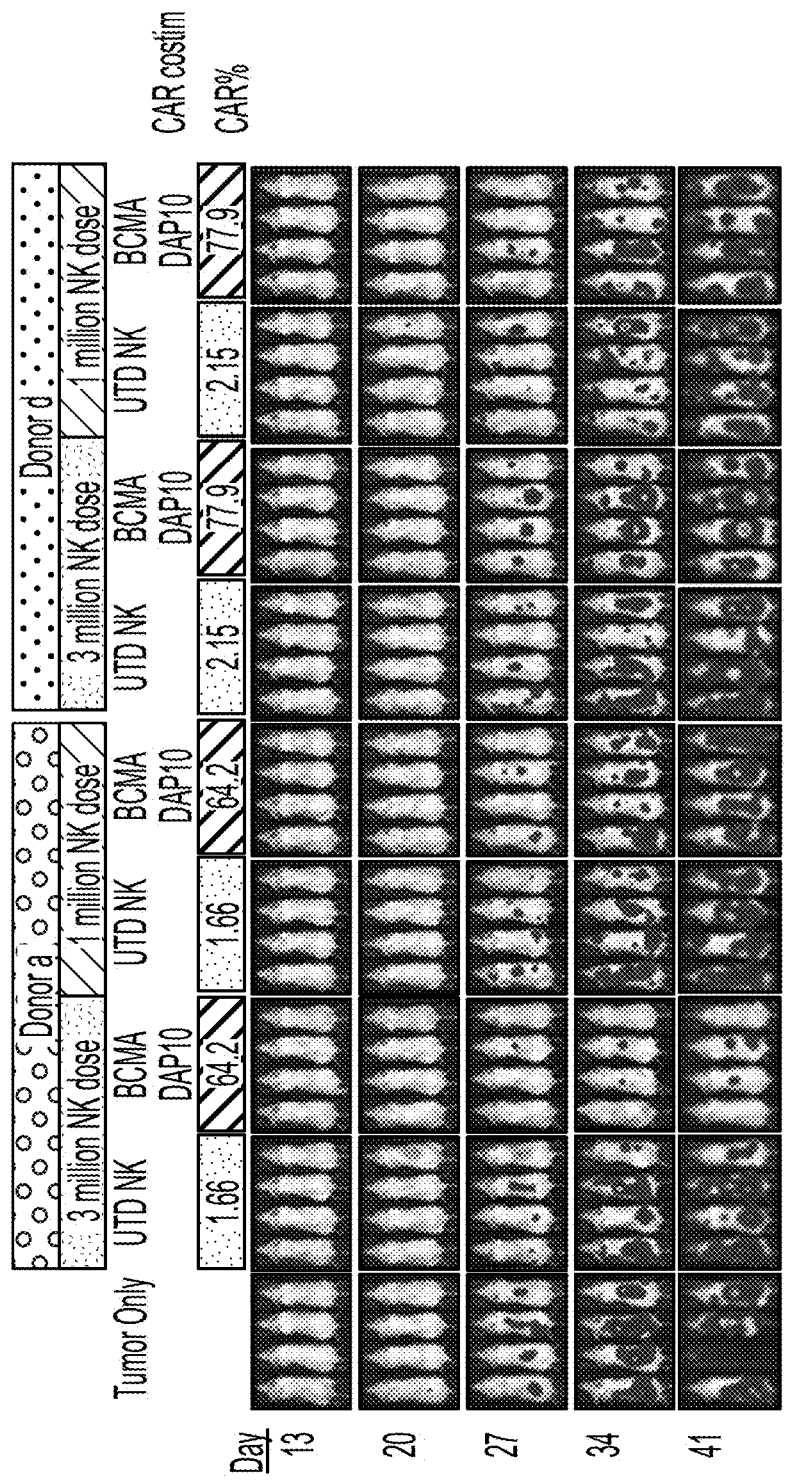
FIGS. 8A and 8B show in vivo efficacy of BCMA-DAP10 CAR in RPMI-8226 tumor model at multiple doses.
Figure 8B:
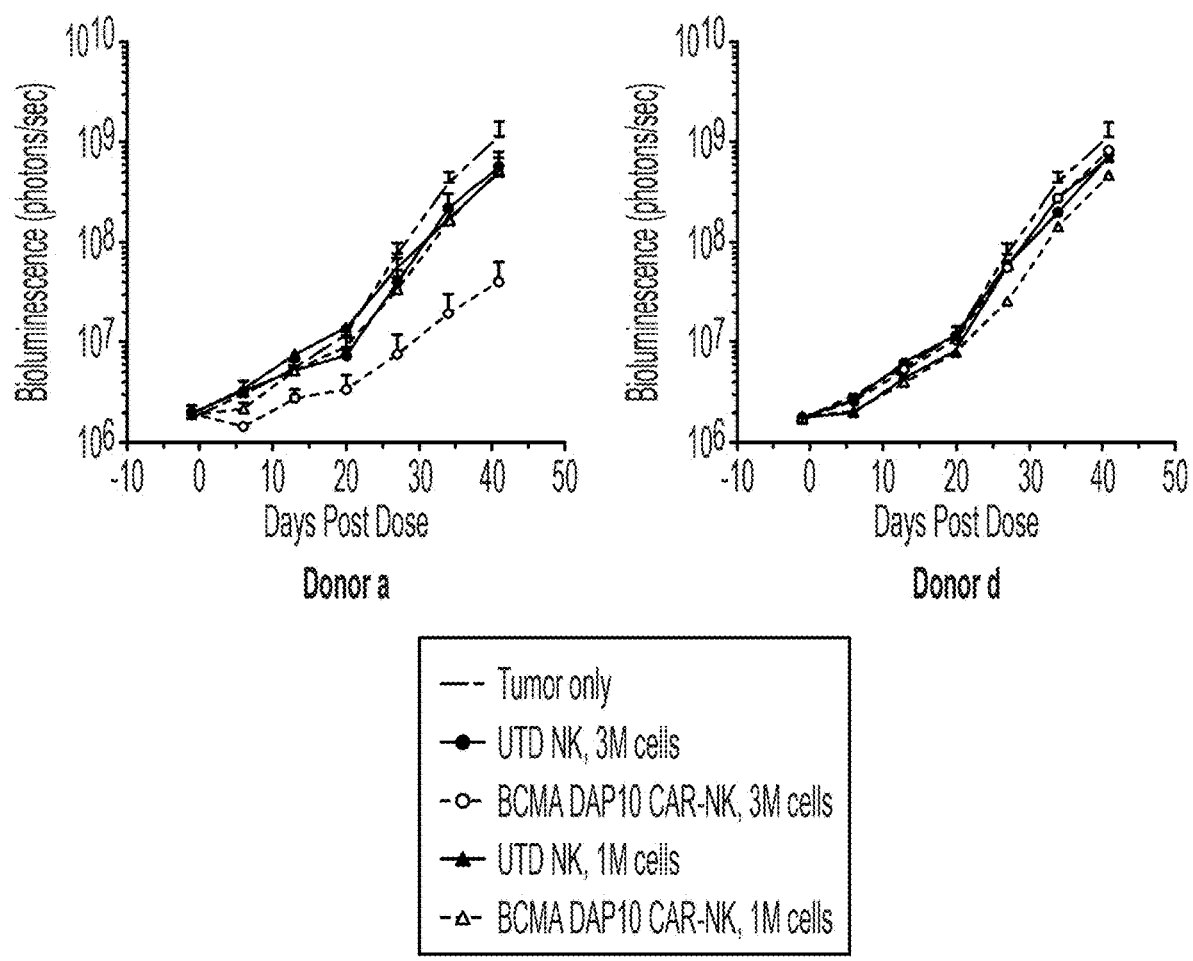

BCMA-DAP10-CAR showed highest efficacy in vivo at a dose of 3M CAR-NK cells per mouse (FIGS. 8A and 8B).

Example 8: In Vitro Efficacy of BCMA DAP10 CAR Against Tumor Lines Expressing Different Levels of Stress Ligands This Example shows the efficacy of BCMA-DAP10-CAR comprised in SEQ ID NO: 29 and BCMA-CD28-CAR comprised in SEQ ID NO: 45, expressed in CB-NK cells.

Figure 9:
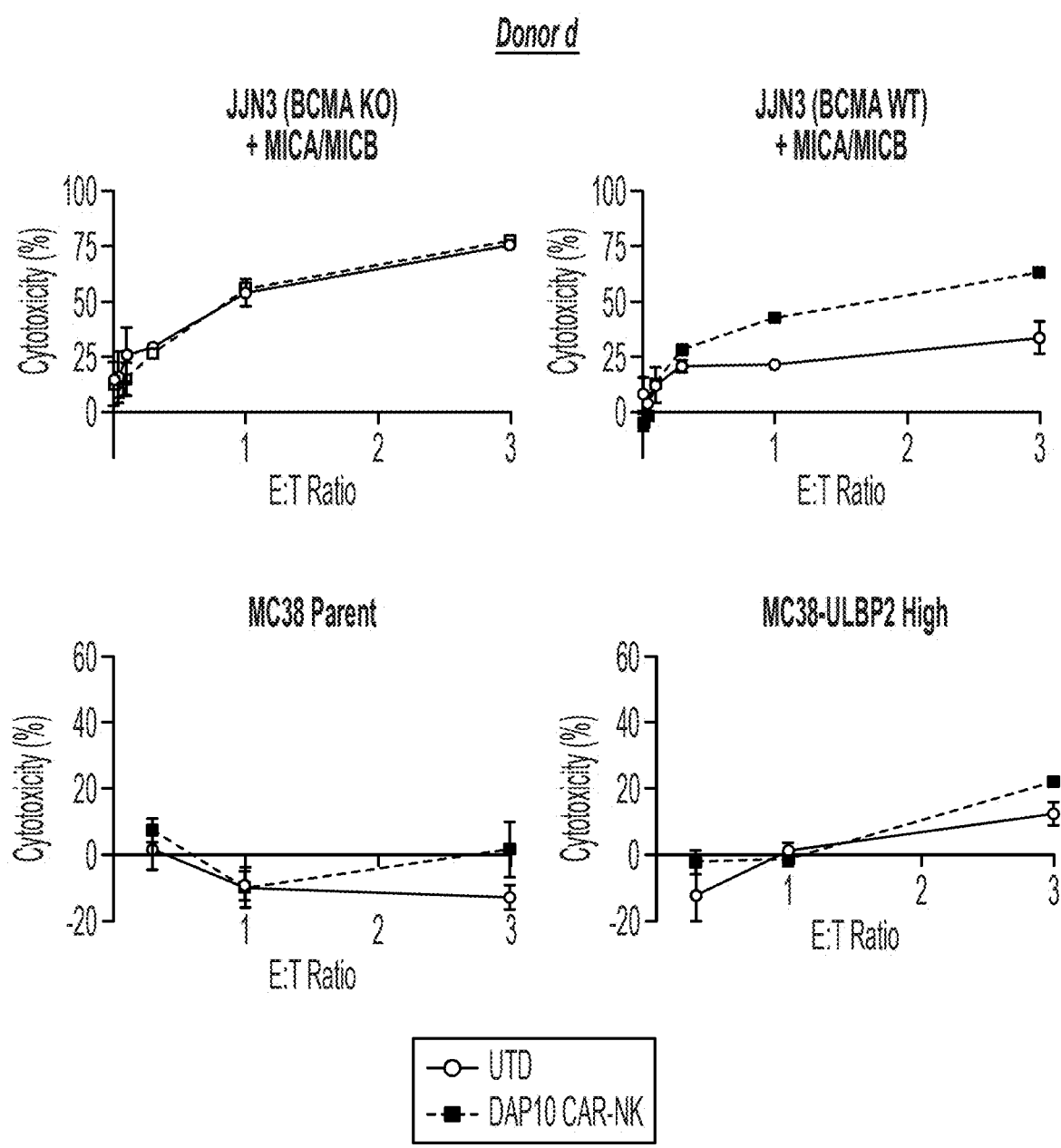
FIG. 9 shows in vitro efficacy of BCMA-DAP10 CAR against tumor lines expressing different levels of stress ligands (Donor d)
Figure 10:
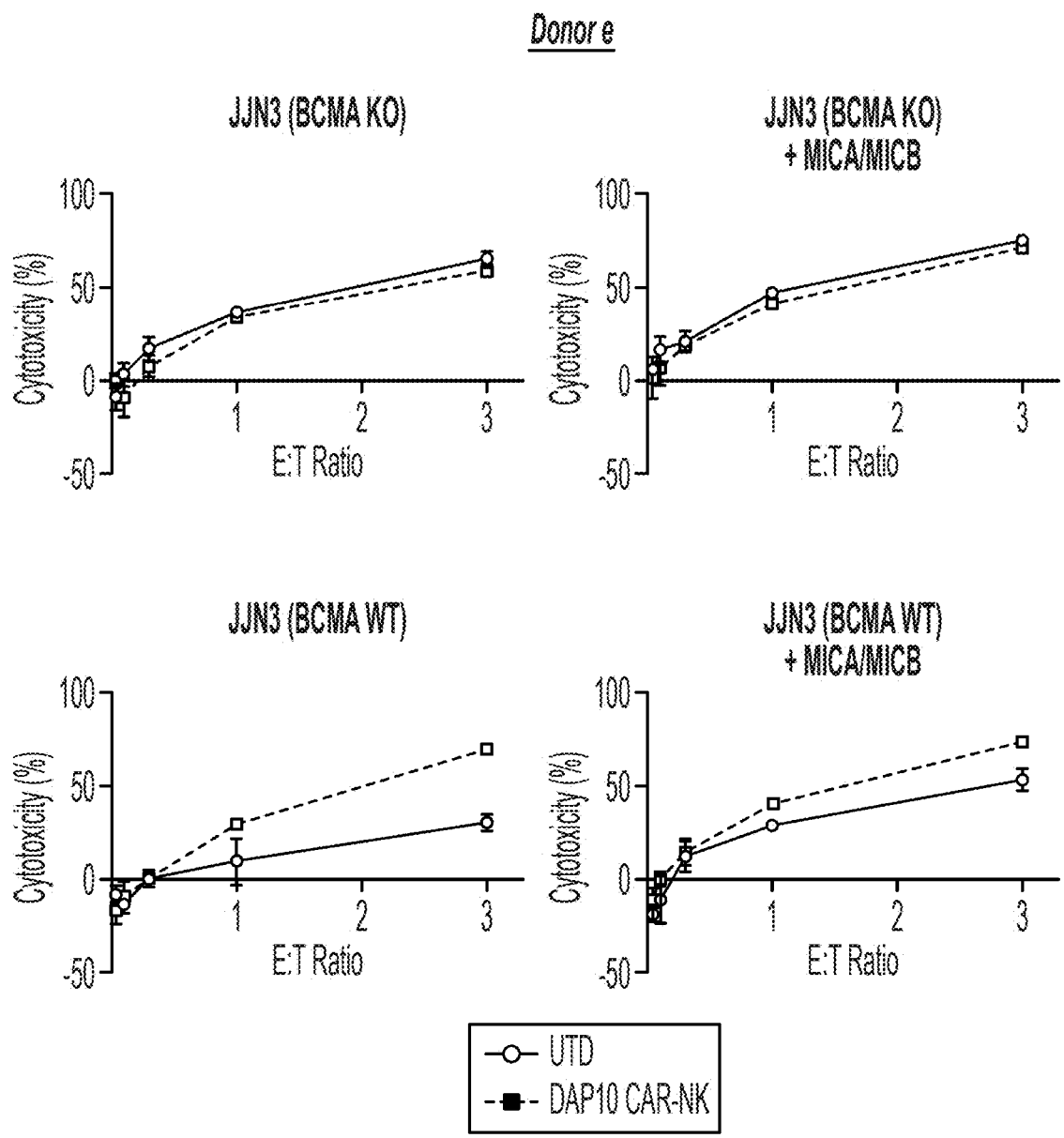
FIG. 10 shows In vitro efficacy of BCMA DAP10 CAR against tumor cell lines expressing different levels of stress ligands (Donor e)
Figure 11A:
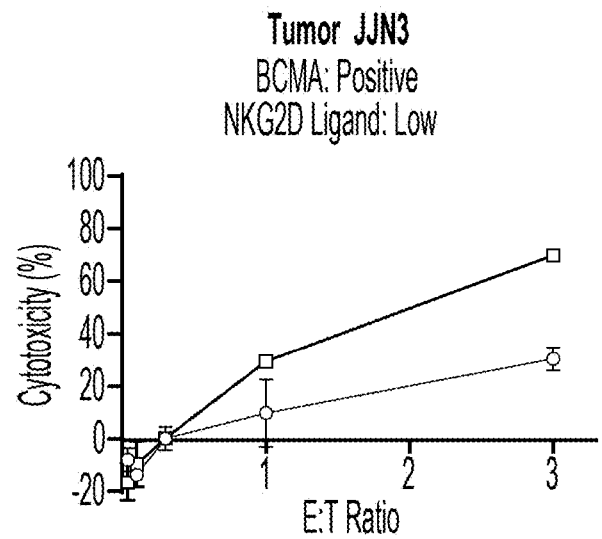
FIGS. 11A-C show in vitro efficacy of BCMA-DAP10-CAR against tumor cell lines expressing different levels of stress ligands and normal cells.
Figure 11B:
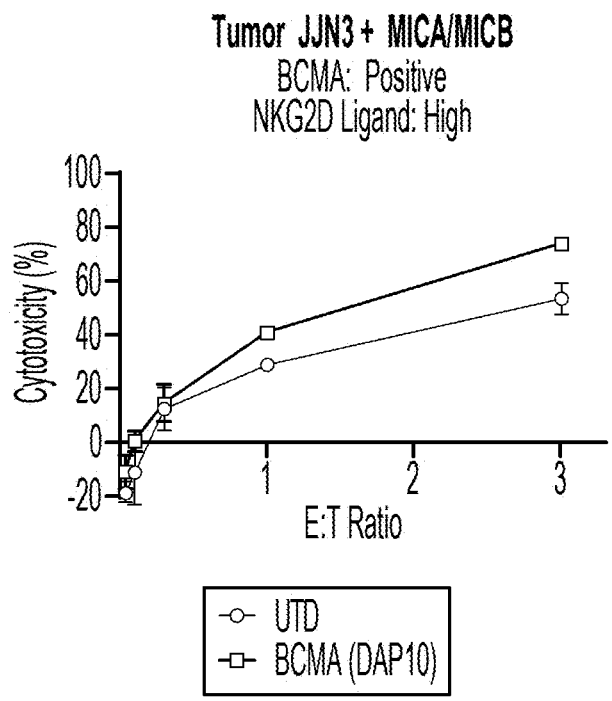
Figure 11C:
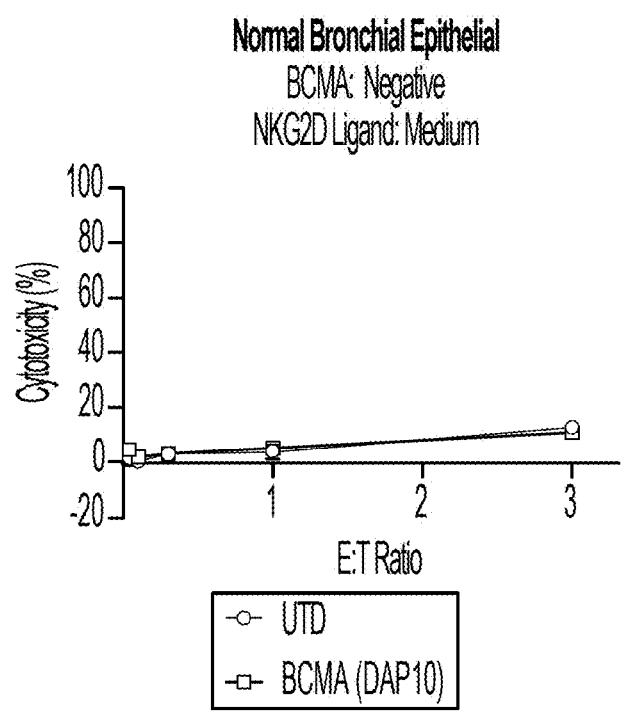

JJN3 (BCMA KO), JJN3 (BCMA KO)+MICA/MICB, JJN3 (BCMA WT), and JJN3 (BCMA WT)+MICA/MICB target cells were prepared and seeded in a 96 well plate in a 100 uL volume to obtain 20,000 target cells/well. The CAR expressing NK cells and control NK cells (Untransduced; UTD) were prepared and resuspended in assay medium at a concentration of 1.8 ×10^6 cells/mL. The effector cell suspensions were then diluted and 100 µL of the diluent was added to the plate containing target cells to achieve the effector-to-target (E:T) ratios indicated in the plots as shown in FIGS. 9-11. The cells were incubated in a 37 C/5% CO2 incubator for 20-24 hours.

Following the incubation, the cells were transferred to another round bottom 96-well plate for cell staining. The cells, after pelleted by centrifugation, were stained with fixable viability dye eFluor-780 (1:1000 dilution in PBS) for 15 minutes on ice in the dark. After washed and re-pelleted, the cells were resuspended in 50 µL of human Fc block (diluted 1:10 in staining buffer) and incubated at room temperature for 10 minutes in the dark. The cells were then stained with 50 µL of a fluorescently conjugated mouse anti-human CD138 antibody for 30 minutes on ice in the dark. The stained cells were washed, resuspended and recorded on an Attune flow cytometer.

Data were exported and analyzed using FlowJo v10.6.2. Live CD138+ target cells excluding the viability dye were quantified. The average live target cell count was determined for of all control wells (target cells alone; no treatment). The cytotoxicity was calculated using the following equation:

Cytotoxicity=100−(target cell count in test well/average target cell count in control wells)*100

Cell Titer Glo-Based Cytotoxicity Assay

MC38 parent, MC38-ULBP2 High, and primary bronchial epithelial target cells were prepared at a concentration of 2×10^5 cells/mL in assay medium (SCGM supplemented with 10% FBS). Target cells were seeded in a 100 uL volume to obtain 20,000 target cells per well in a flat 96-well plate, and allowed to adhere for 12-14 hours prior to effector cell addition. The CAR expressing NK cells and control NK cells (Untransduced; UTD) were prepared and resuspended in assay medium at a concentration of 1.8×10^6 cells/mL. The effector cell suspensions were then diluted and 100 µL of the diluent was added to the plate containing target cells to achieve the effector-to-target (E:T) ratios indicated in the plots in FIGS. 9-11. The cells were incubated in a 37 C/5% CO2 incubator for 20-24 hours.

Following the incubation, the cell supernatant was aspirated. Each well, after washed with 200 µL assay media, was supplemented with 100 µL of assay media and 100 µL of cell titer glo solution. Cells were incubated for ~7 minutes at room temperature with gentle shaking. Luminescence was measured on a Tecan spark instrument.

The average luminescence (relative luminescence unit, RLU) was determined for all control wells (target cells alone; no treatment). In addition, RLU was determine for each effector cell alone in the absence of target cell stimulation. Cytotoxicity was calculated using the following equation:

Cytotoxicity=100−(*RLU*(test well)−*RLU*(effector cell alone)/average *RLU* control)*100

Example 9: BCMA CAR Surface Expression Improvement Following Codon Optimization

This Example shows the surface expression of BCMA-DAP10-CAR using construct comprising SEQ ID NO: 25 and SEQ ID NO:55 in Table 5 on NK cells of 4 different CBU donors. In this example, construct comprising sequence represented by SEQ ID NO: 25 enhanced the surface expression of the BCMA CAR in all 4 CBU donors.

Serial dilution of virus was performed using 2-fold dilution for a total of 8 points. A 24-well plate was pre-coated with 40 μg/mL retronectin overnight then blocked with complete media for 10 minutes at 37° C. prior to use. 1 ml of virus dilution was added to the plate then centrifuged at 2000×g at 32° C. for 90 minutes. After centrifugation, plate was aspirated and 1×106 NK in 1 mL of media was added along with 1 ml of appropriate virus dilution. The plate was then centrifuged at 400×g for 5 mins at 32° C. and placed inside the incubator at 37° C. for 48 hrs.

Following the incubation, the cells were transferred to a v-bottom 96-well plate for cell staining. The cells, after pelleted by centrifugation and washed with flow buffer, were stained in 1:10 Fc block with fluorescently conjugated mouse anti-human CD3, mouse anti-human CD56, mouse anti-human NKG2D, and recombinantly produced human BCMA for 30 minutes on ice in the dark. The stained cells were washed, resuspended in Sytox Viability Dye and recorded on an MACSquant flow cytometer. Data were exported and analyzed using FlowJo v10.6.2. Live CD3-CD56+BCMA+ target cells excluding the viability dye were quantified.

Figure 12A:
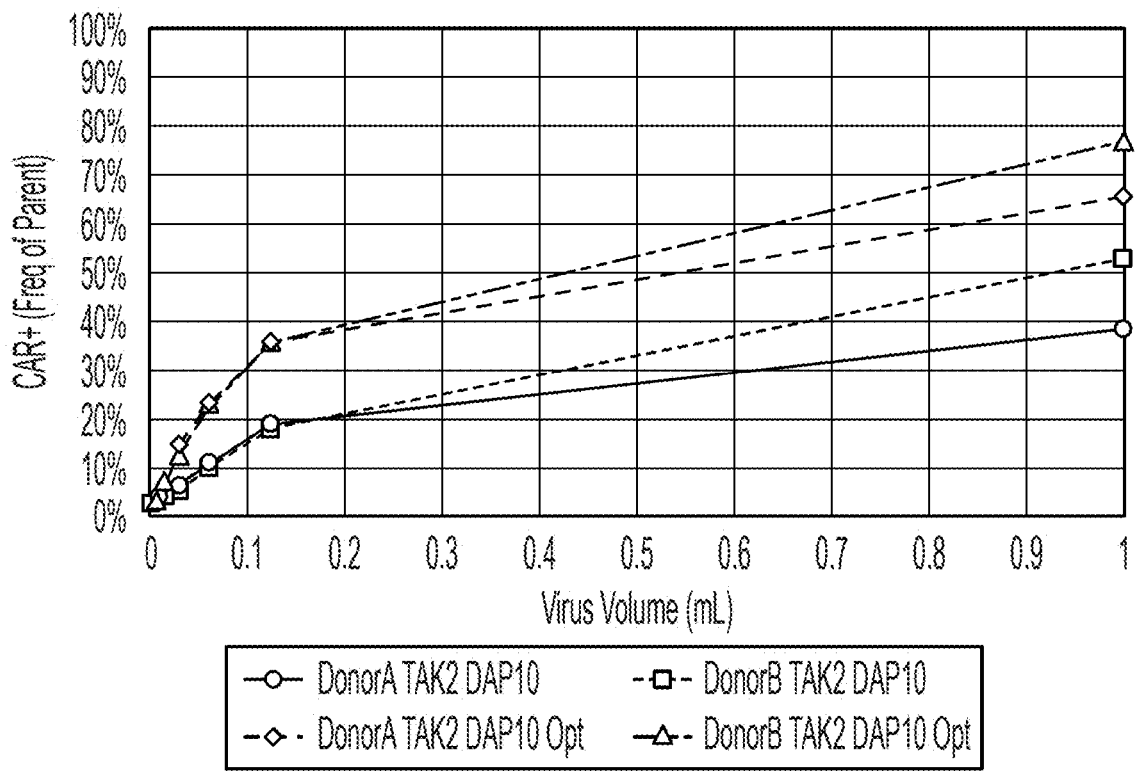
FIGS. 12A-B demonstrates CAR protein expression using codon-optimized nucleic acid sequence. The codon-optimized BCMA-DAP10 CAR construct (SEQ ID NO: 25) yielded higher transduction efficiency against the BCMA-DAP10 CAR (SEQ ID NO: 55) across all four Cord blood NK donors.
Figure 12B:
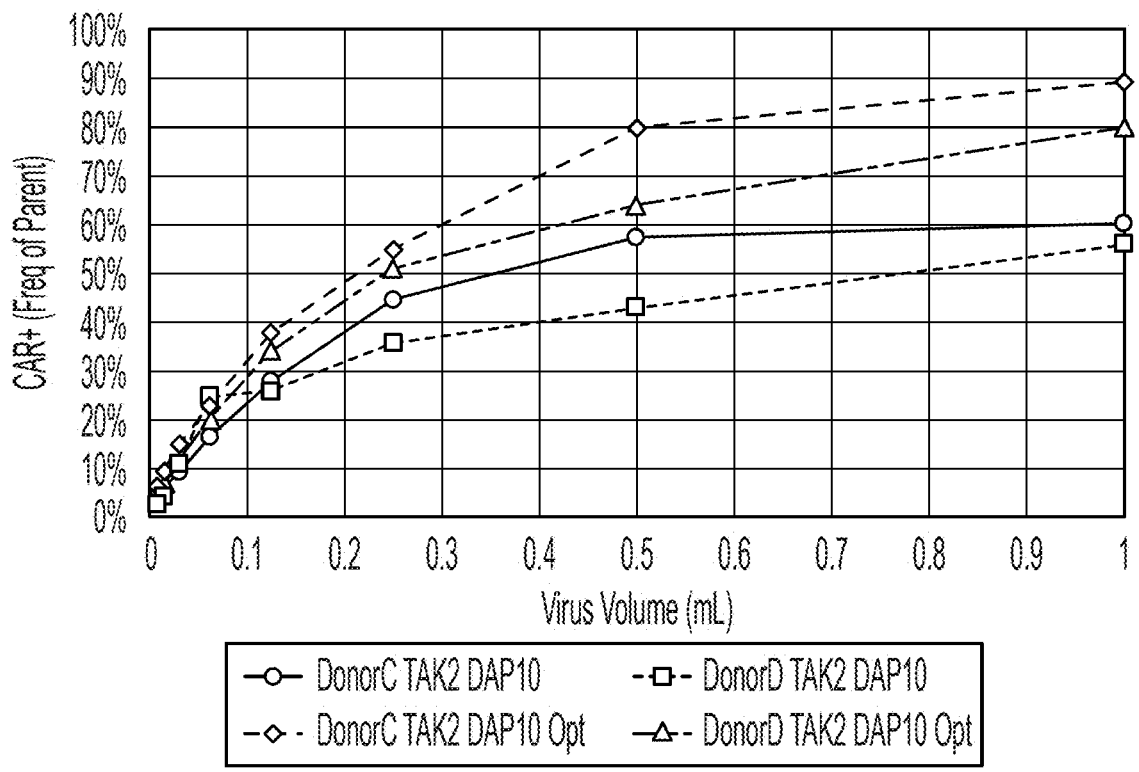

The surface expression of the BCMA CAR using construct comprising SEQ ID NO: 55 or SEQ ID NO: 25 in 4 CBU donors is shown in FIG. 12A and FIG. 12B. The surface expression of the BCMA CAR using construct comprising SEQ ID NO: 25 yielded higher transduction efficiency against the BCMA-DAP10 CAR construct comprising SEQ ID NO: 55 across all four Cord blood NK donors.

TABLE 5

Sequences of BCMA targeting CAR constructs

Amino acid sequence comprising BCMA-DAP10 CAR
MEFGLSWLFLVAILKGVQCQITLRESGGDVVQPGRSLRLSCAASGFTFSSYAIHWVRQAPGK
GLEWVAVTWHDGSNKYYAESVMGRFTISRDNSKNTLYLHMNSLRAEDTGVYYCARAKFG
EPQYFQHWGQGTLVTVSSGGGGSGGGGSGGGGSDIVMTQSPSFLSASVGDRVTITCRASQGI
NNYLAWYQQKPGIAPKLLIYAASTLQSGVPSRFGGSGSGTEFTLTISSLQPEDFATYYCQQLK
SYPFTFGPGTKVEIKRAAAIEVMYPPPYLDNEKSNGTIIHVKGKHLCPSPLFPGPSKPKDPKF
WVLVVVGGVLACYSLLVTVAFIIFWVLCARPRRSPAQEDGKVYINMPGRGRVKFSRSADAP
AYQQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPRGPQCTNYALLKLAGDVES
NPGPMRISKPHLRSISIQCYLCLLLNSHFLTEAGIHVFILGCFSAGLPKTEANWVNVISDLKKIE
DLIQSMHIDATLYTESDVHPSCKVTAMKCFLLELQVISLESGDASIHDTVENLIILANNSLSSN
GNVTESGCKECEELEEKNIKEFLQSFVHIVQMFINTS (SEQ ID NO: 13)

Nucleic acid sequence comprising BCMA-DAP10 CAR
atggagttcggcctgagctggctgttcctggtggccatcctgaagggcgtgcagtgccagatcaccctgagggagtctggaggcgacgtggtgc
agcctggaaggagcctgagactgagctgcgccgcctctggattcaccttcagcagctacgccatccactgggtcaggcaggctcctggcaaggg
actggagtgggtggccgttacctggcacgacggcagcaacaagtactacgccgagagcgttatgggcaggttcaccatcagcagggacaacagc
aagaacaccctgtacctgcacatgaactctctgagggccgaggacacaggcgtgtactactgcgccagggccaagttcggtgagcccagtact
tccagcactggggccagggaaccctggtgaccgtgtcttctggcgaggggatctggaggaggaggaagtggaggcggtggcagcgacatcgt
gatgacccagagccctagcttcctgtctgccagcgtgggagacagggtgaccatcacctgcagagccagccagggcatcaataatacctggcc
tggtaccagcagaagcccggcattgccccaagctcctgatctacgccgccagcaccctgcaaagcggcgtgccctctaggttcggcggatctg
gaagcggcaccgagttcaccctgaccattagcagcctgcagcccgaggacttcgccacctactactgccagcagctgaagagctacccttcac
cttcggccctggcaccaaggtggagatcaagagggccgccgccattgaggtgatgtaccccccccctacctggacaacgagaagaggcaacggc
accatcatccacgtgaagggcaagcacctctgccctagccccctgttccctggacccagcaagcccaaggaccccaagttctgggtgctggtcg
tggtgggaggcgttctggcctgctacagcctgctggtgacagtggcctttatcatcttctgggtcctgtgcgccagacctaggagaagccccgc
ccaggaagacggaaaggtctacatcaacatgcccggaagggaaggtcaagttcagccggtctgctgatgctcccgcctaccagcaaggccaa
aaccagctgtacaacgagctgaacctgggcaggagagaagagtacgacgtgctggacaagagagaggcagggacccgagatgggaggcaagc
ccagaaggaagaaccccaggagggcctgtacaatgagctgcagaaggacaagatggccgaggcctacagcgagatcggcatgaagggcgagag
aagaagggcaagggccacgacggattgtaccagggcctgagcaccgctaccaaggacacctacgacgccctgcatatgcaagctctgcctcct
aggggccctcagtgcaccaactacgccctgctcaagctggctggcgacgtggagagcaaccccgggaccccatgaggatcagcaagcctcacctga
ggagcattagcatccagtgctacctgtgcctgctcctgaactcccacttcctgaccgaggccggcatccacgtcttcatcctgggctgcttcag
cgctggcctgcccaaaaccgaggccaactgggtgaacgtgatcagcgacctcaagaagatcgaggacctgatccagagcatgcacatcgacgcc
accctgtataccgagagcgacgtgcacccagctgcaaggtgaccgccatgaagtgcttcctgctggagctgcaggtcatcagcctggagagcg
gcgatgccagcatccacgacaccgtggagaacctgatcatcctggccaacaacagcctgagcagcaacgggaacgtgaccgagtccggctgcaa
ggagtgcgaggagctggaggagaagaacatcaaggagttcctgcagtccttcgtgcacatcgtgcagatgttcatcaacaccagctga (SEQ ID NO: 25)

Nucleic acid sequence comprising BCMA-DAP10 CAR
atggaattcgggctgtcctggcttttcttggtcgcaattcttaagggcgtccaatgtcagataactctgcgcgagtcaggaggagacgtggtgc
aaccgggcagatctctcaggctttcatgtgccgccagtggcttcacatttagctcttatgcaatacattgggtcaggcaggctcctggcaaggg
cttggaatgggtagcggttacctggcatgatggatctaacaaatactacgccgagtctgttatgggtcgattcacaatttctcgagacaattca
aaaacacactctacctgcatatgaactcacttagagcagaggacactggtgtctattactgcgccagagcaaaattcggcgagccacagtatt
tccagcactggggacaaggaacctctgtaacagtatctagtggggagcggagggtctggaggaggggggagcggggggaggcggctctgatattgt
tatgacccaatcaccatcttttctgagcgctagtgtcggcgacagggttacaatcacatgccgagcaagccaaggaatcaacaattatctcgca
tggtatcaacaaaaaccaggtatcgccccgaaacttcttatttacgcagcatcaaccctgcaaagcggagttccttctagatttggtggcagcg
gctccgggactgaattcactcttactattcctccttcaacccgaagatttcgccacatattactgccagcagcttaagtcatacccctcac
ttttggccaggaactaaagttgaaatcaaacgggcgcaattgaagttatgtatcctcctcctaccctagacaatgagaagagcaatgga
accattatccatgtgaaaggaaacacctttgtccaagtccccctatttcccggaccttctaagcccaaagatcccaaattttgggtgctggtgg
tggttggtggagtcctggcttgctatagctgctagtaacagtggcctttattattttctgggtgctttgcgcacgcccacgccgcagcccgc
ccaagaagatggcaaagtctacatcaacatgccaggcaggggccgcgtgaagttcagcaggagcgcagacgccccgcgtaccagcagggccag
aaccagctctataacgagctcaatctaggacgaagagaggagtacgatgttttggacaaaagacgtgccgggacccctgagatgggggaaagc
cgagaaggaagaaccctcaggaaggcctgtacaatgaactgcagaaagataagatggccgaggcctacagtgagattggatgaaagcgagcg
ccggagggcaagggcacgatggcctttaccagggtctcagtacagccaccaaggacacctacgacgcccttcacatgcaggccctgccccct
cgcggaccgcagtgtactaattatgctctcttgaaattggctggagatgttgagagcaatcccgggcccatgcgcattagcaagcccacctgc
ggagcatcagcatccagtgctacctgtgcctgctgctgaacagccacttcctgaccgaggccggcatccacgtgttcatcctgggctgcttcag
cgccggactgcccaagaccgaggccaactgggtgaacgtgatcagcgacctgaagaagatcgaggacctgatccagagcatgcacatcgacgcc TABLE 5-continued Sequences of BCMA targeting CAR constructs accctgtacaccgagagcgacgtgcaccccagctgcaaggtgaccgccatgaagtgctttctgctggaactgcaggtgatcagcctggaaagcg
gcgacgccagcatccacgacaaccgtggagaacctgatcatcctggccaacaacagcctgagcagcaacggcaacgtgaccgagagcggctgcaa
agagtgcgaggaactggaagagaagaacatcaaagagtttctgcagagcttcgtgcacatcgtgcagatgttcatcaacaccagctga (SEQ
ID NO: 55)

Example 10: In Vivo Efficacy of Codon-Optimized BCMA CAR NK at Low Doses 10-12 week old female NSG mice were whole-body irradiated at 150 cGy 24 hours prior to tumor inoculation. MM. 1S-flluc-MDA cells were prepared in PBS suspension at a concentration of $2.5 \times 10^6$ cells/ml, for intravenous inoculation of cells at 0.5×106/animal. Bioluminescent images were taken 1 day prior to dosing, 6 days after tumor inoculation, and animals were randomized based on total flux into groups of 5 animals per arm. Animals were dosed 7 days after tumor inoculation. The CAR (coded by nucleic acid sequence represented by SEQ ID NO: 25) expressing NK (i.e., CAR NK) cells in the relevant concentrations were resuspended in PBS and transferred to the vivarium on ice in small batches to ensure timely infusion into the animals while maintaining the CAR expressing NK cell viability. Bioluminescent images were carried out weekly on a Xenogen IVIS to monitor tumor progression. Body weights were taken three times a week, alongside clinical observations to monitor for any signs of toxicity. Microsampling (via submandibular collection of blood) was carried out once a week for cellular kinetics analysis to quantify CAR NK expansion in vivo, either by ddPCR or flow cytometric analysis. At humane or study endpoint, necropsy of animals from studies of interest was carried out to obtain various tissues for tox/pathology assessment.

Figure 13:
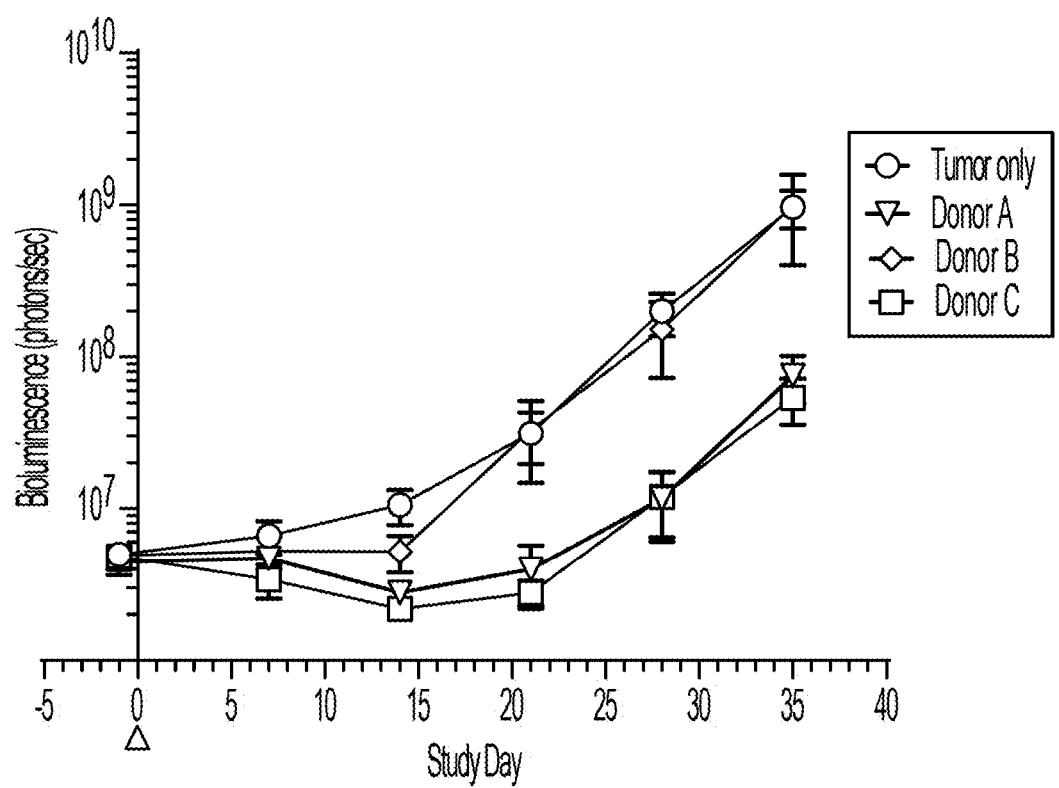
FIG. 13 demonstrates in vivo efficacy of NK cell expressing BCMA CAR (expressed using codon-optimized nucleic acid sequence) at a low CAR+ dose.

As shown in FIG. 13, CAR+NK cells were capable of suppressing tumor growth in 2 of the 3 groups tested.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

SEQUENCE LISTING

```
Sequence total quantity: 65
SEQ ID NO: 1            moltype = AA  length = 120
FEATURE                 Location/Qualifiers
source                  1..120
                        mol_type = protein
                        organism = synthetic construct
SEQUENCE: 1
QITLRESGGD VVQPGRSLRL SCAASGFTFS SYAIHWVRQA PGKGLEWVAV TWHDGSNKYY   60
AESVMGRFTI SRDNSKNTLY LHMNSLRAED TGVYYCARAK FGEPQYFQHW GQGTLVTVSS  120

SEQ ID NO: 2            moltype = AA  length = 5
FEATURE                 Location/Qualifiers
source                  1..5
                        mol_type = protein
                        organism = synthetic construct
SEQUENCE: 2
SYAIH                                                                 5

SEQ ID NO: 3            moltype = AA  length = 17
FEATURE                 Location/Qualifiers
source                  1..17
                        mol_type = protein
                        organism = synthetic construct
SEQUENCE: 3
VTWHDGSNKY YAESVMG                                                   17

SEQ ID NO: 4            moltype = AA  length = 11
FEATURE                 Location/Qualifiers
source                  1..11
                        mol_type = protein
                        organism = synthetic construct
SEQUENCE: 4
AKFGEPQYFQ H                                                         11

SEQ ID NO: 5            moltype = AA  length = 107
FEATURE                 Location/Qualifiers
source                  1..107
                        mol_type = protein
                        organism = synthetic construct
SEQUENCE: 5
```

```
DIVMTQSPSF LSASVGDRVT ITCRASQGIN NYLAWYQQKP GIAPKLLIYA ASTLQSGVPS     60
RFGGSGSGTE FTLTISSLQP EDFATYYCQQ LKSYPFTFGP GTKVEIK                 107

SEQ ID NO: 6            moltype = AA   length = 11
FEATURE                 Location/Qualifiers
source                  1..11
                        mol_type = protein
                        organism = synthetic construct
SEQUENCE: 6
RASQGINNYL A                                                         11

SEQ ID NO: 7            moltype = AA   length = 7
FEATURE                 Location/Qualifiers
source                  1..7
                        mol_type = protein
                        organism = synthetic construct
SEQUENCE: 7
AASTLQS                                                               7

SEQ ID NO: 8            moltype = AA   length = 9
FEATURE                 Location/Qualifiers
source                  1..9
                        mol_type = protein
                        organism = synthetic construct
SEQUENCE: 8
QQLKSYPFT                                                             9

SEQ ID NO: 9            moltype = DNA   length = 45
FEATURE                 Location/Qualifiers
source                  1..45
                        mol_type = other DNA
                        organism = synthetic construct
SEQUENCE: 9
gggggcggag ggtctggagg agggggagc ggggaggcg gctct                      45

SEQ ID NO: 10           moltype = DNA   length = 45
FEATURE                 Location/Qualifiers
source                  1..45
                        mol_type = other DNA
                        organism = synthetic construct
SEQUENCE: 10
ggcggagggg gatctggagg aggaggaagt ggaggcggtg gcagc                    45

SEQ ID NO: 11           moltype = DNA   length = 66
FEATURE                 Location/Qualifiers
source                  1..66
                        mol_type = other DNA
                        organism = synthetic construct
SEQUENCE: 11
ggaccgcagt gtactaatta tgctctcttg aaattggctg gagatgttga gagcaatccc    60
gggccc                                                               66

SEQ ID NO: 12           moltype = DNA   length = 66
FEATURE                 Location/Qualifiers
source                  1..66
                        mol_type = other DNA
                        organism = synthetic construct
SEQUENCE: 12
ggccctcagt gcaccaacta cgccctgctc aagctggctg gcgacgtcga gagcaacccc    60
ggaccc                                                               66

SEQ ID NO: 13           moltype = AA   length = 655
FEATURE                 Location/Qualifiers
source                  1..655
                        mol_type = protein
                        organism = synthetic construct
SEQUENCE: 13
MEFGLSWLFL VAILKGVQCQ ITLRESGGDV VQPGRSLRLS CAASGFTFSS YAIHWVRQAP     60
GKGLEWVAVT WHDGSNKYYA ESVMGRFTIS RDNSKNTLYL HMNSLRAEDT GVYYCARAKF    120
GEPQYFQHWG QGTLVTVSSG GGGSGGGGSG GGGSDIVMTQ SPSFLSASVG DRVTITCRAS    180
QGINNYLAWY QQKPGIAPKL LIYAASTLQS GVPSRFGGSG SGTEFTLTIS SLQPEDFATY    240
YCQQLKSYPF TFGPGTKVEI KRAAAIEVMY PPPYLDNEKS NGTIIHVKGK HLCPSPLFPG    300
PSKPKDPKFW VLVVVGGVLA CYSLLVTVAF IIFWVLCARP RRSPAQEDGK VYINMPGRGR    360
VKFSRSADAP AYQQGQNQLY NELNLGRREE YDVLDKRRGR DPEMGGKPRR KNPQEGLYNE    420
LQKDKMAEAY SEIGMKGERR RGKGHDGLYQ GLSTATKDTY DALHMQALPP RGPQCTNYAL    480
LKLAGDVESN PGPMRISKPH LRSISIQCYL CLLLNSHFLT EAGIHVFILG CFSAGLPKTE    540
ANWVNVISDL KKIEDLIQSM HIDATLYTES DVHPSCKVTA MKCFLLELQV ISLESGDASI    600
HDTVENLIIL ANNSLSSNGN VTESGCKECE ELEEKNIKEF LQSFVHIVQM FINTS         655
```

```
SEQ ID NO: 14            moltype = AA  length = 402
FEATURE                  Location/Qualifiers
source                   1..402
                         mol_type = protein
                         organism = synthetic construct
SEQUENCE: 14
MLEGVQVETI SPGDGRTFPK RGQTCVVHYT GMLEDGKKVD SSRDRNKPFK FMLGKQEVIR   60
GWEEGVAQMS VGQRAKLTIS PDYAYGATGH PGIIPPHATL VFDVELLKLE SGGGSGVDGF  120
GDVGALESLR GNADLAYILS MEPCGHCLII NNVNFCRESG LRTRTGSNID CEKLRRRFSS  180
LHFMVEVKGD LTAKKMVLAL LELAQQDHGA LDCCVVVILS HGCQASHLQF PGAVYGTDGC  240
PVSVEKIVNI FNGTSCPSLG GKPKLFFIQA CGGEQKDHGF EVASTSPEDE SPGSNPEPDA  300
TPFQEGLRTF DQLDAISSLP TPSDIFVSYS TFPGFVSWRD PKSGSWYVET LDDIFEQWAH  360
SEDLQSLLLR VANAVSVKGI YKQMPGCFNF LRKKLFFKTS AS                    402

SEQ ID NO: 15            moltype = AA  length = 15
FEATURE                  Location/Qualifiers
source                   1..15
                         mol_type = protein
                         organism = synthetic construct
SEQUENCE: 15
GGGGSGGGGS GGGGS                                                   15

SEQ ID NO: 16            moltype = AA  length = 19
FEATURE                  Location/Qualifiers
source                   1..19
                         mol_type = protein
                         organism = synthetic construct
SEQUENCE: 16
GGGGSGGGGS GGGSGGGGS                                               19

SEQ ID NO: 17            moltype = AA  length = 24
FEATURE                  Location/Qualifiers
source                   1..24
                         mol_type = protein
                         organism = synthetic construct
SEQUENCE: 17
GGGGSGGGGS GGGGSGGGSG GGGS                                         24

SEQ ID NO: 18            moltype = AA  length = 20
FEATURE                  Location/Qualifiers
source                   1..20
                         mol_type = protein
                         organism = synthetic construct
SEQUENCE: 18
GGGGSGGGGS GGGGSGGGGS                                              20

SEQ ID NO: 19            moltype = DNA  length = 60
FEATURE                  Location/Qualifiers
source                   1..60
                         mol_type = other DNA
                         organism = synthetic construct
SEQUENCE: 19
ggtggtggtg gttctggtgg tggtggttct ggcggcggcg gctccggtgg tggtggatcc   60

SEQ ID NO: 20            moltype = AA  length = 242
FEATURE                  Location/Qualifiers
source                   1..242
                         mol_type = protein
                         organism = synthetic construct
SEQUENCE: 20
QITLRESGGD VVQPGRSLRL SCAASGFTFS SYAIHWVRQA PGKGLEWVAV TWHDGSNKYY   60
AESVMGRFTI SRDNSKNTLY LHMNSLRAED TGVYYCARAK FGEPQYFQHW GQGTLVTVSS  120
GGGGSGGGGS GGGGSDIVMT QSPSFLSASV GDRVTITCRA SQGINNYLAW YQQKPGIAPK  180
LLIYAASTLQ SGVPSRFGGS GSGTEFTLTI SSLQPEDFAT YYCQQLKSYP FTFGPGTKVE  240
IK                                                                 242

SEQ ID NO: 21            moltype = AA  length = 47
FEATURE                  Location/Qualifiers
source                   1..47
                         mol_type = protein
                         organism = synthetic construct
SEQUENCE: 21
RAAAIEVMYP PPYLDNEKSN GTIIHVKGKH LCPSPLFPGP SKPKDPK                 47

SEQ ID NO: 22            moltype = AA  length = 27
FEATURE                  Location/Qualifiers
source                   1..27
                         mol_type = protein
                         organism = synthetic construct
```

```
SEQUENCE: 22
FWVLVVVGGV LACYSLLVTV AFIIFWV                                           27

SEQ ID NO: 23           moltype = AA  length = 112
FEATURE                 Location/Qualifiers
source                  1..112
                        mol_type = protein
                        organism = synthetic construct
SEQUENCE: 23
RVKFSRSADA PAYQQGQNQL YNELNLGRRE EYDVLDKRRG RDPEMGGKPR RKNPQEGLYN        60
ELQKDKMAEA YSEIGMKGER RRGKGHDGLY QGLSTATKDT YDALHMQALP PR               112

SEQ ID NO: 24           moltype = AA  length = 24
FEATURE                 Location/Qualifiers
source                  1..24
                        mol_type = protein
                        organism = synthetic construct
SEQUENCE: 24
LCARPRRSPA QEDGKVYINM PGRG                                              24

SEQ ID NO: 25           moltype = DNA  length = 1968
FEATURE                 Location/Qualifiers
source                  1..1968
                        mol_type = other DNA
                        organism = synthetic construct
SEQUENCE: 25
atggagttcg gcctgagctg ctgttcctg gtggccatcc tgaagggcgt gcagtgccag         60
atcaccctga gggagtctgg aggcgacgtg gtgcagcctg aaggagcct gagactgagc        120
tgcgccgcct ctggattcac cttcagcagc tacgccatcc actgggtcag gcaggctcct       180
ggcaagggac tggagtgggt ggccgttacc tggcacgacg gcagcaacaa gtactacgcc       240
gagagcgtta tgggcaggtt caccatcagc agggacaaca gcaagaacac cctgtacctg       300
cacatgaact ctctgagggc cgaggacaca ggcgtgtact actgcgccag ggccaagttc       360
ggtgagcccc agtacttcca gcactgggc cagggaaccc tggtgaccgt gtcttctggc        420
ggaggggat ctggaggagg aggaagtgga ggcgtggca gcgacatcgt gatgacccag         480
agccctagct tcctgtctgc cagcgtggga gacagggtga ccatcacctg cagagccag        540
cagggcatca ataactacct ggcctggtac agcagaagc ccggcattgc ccccaagctc        600
ctgatctacg ccgccagcac cctgcaaagc ggcgtgccct ctaggttcgg cggatctgga       660
agcggcaccg agttcaccct gaccattagc agcctgcagc ccgaggactt cgccacctac       720
tactgccagc agctgaagag ctaccccttc accttcggcc ctggcaccaa ggtggagatc       780
aagagggccg ccgccattga ggtgatgtac cccccccccct acctggacaa cgagaagagc      840
aacggcacca tcatccacgt gaagggcaag cacctctgcc ctagcccct gttccctgga       900
cccagcaagc ccaaggaccc caagttctgg gtgctggtcg tggtgggagg cgttctggcc      960
tgctacagcc tgctggtgac agtggccttt atcatcttct ggcctccgtg gccagacct     1020
aggagaagcc ccgccaggag agacggaaag gtctacatca acatgccgg aaggggaagg     1080
gtcaagttca gccggtctgc tgatgctccc gcctaccagc aaggccaaaa ccagctgtac     1140
aacgagctga acctgggcag agagaagag tacgacgtgc tggacaagag agagaggcagg     1200
gaccccgaga tgggaggcaa gcccagaagg aagaacccc agggggcct gtacaatgag       1260
ctgcagaagg acaagatggc cgaggcctac agcgagatcg gcatgaaggg cgagagaaga     1320
aggggcaagg gccacgacgg attgtaccag ggcctgagca ccgctaccaa ggacacctac     1380
gacgccctgc atatgcaagc tctgcctcct agggggcctc agtgcaccaa ctacgccctg     1440
ctcaagctgg ctggcgacgt cgagagcaac cccggaccca tgaggatcga caagcctcaa     1500
ctgaggagca ttagcatcca gtgctacctg tgcctgctcc tgaactccca cttcctgacc     1560
gaggccggca tccacgtctt catcctgggc tgcttcagcg ctggcctgcc caaaaccgag     1620
gccaactggg tgaacgtgat cagcgacctc aagaagatcg aggacctgat ccagagcatg     1680
cacatcgacg ccaccctgta taccgagagc gacgtgcacc ccagctgcaa ggtgaccgcc     1740
atgaagtgct tcctgctgga gctgcaggtc atcagcctgg agagcggcga tgccagcatc     1800
cacgacaccg tggagaacct gatcatcctg gccaacaaca gcctgagcag caacgggaac     1860
gtgaccgagt ccggctgcaa ggagtgcgag gagctggagg agaagaacat caaggagttc     1920
ctgcagtcct tcgtgcacat cgtgcagatg ttcatcaaca ccagctga                 1968

SEQ ID NO: 26           moltype = AA  length = 133
FEATURE                 Location/Qualifiers
source                  1..133
                        mol_type = protein
                        organism = synthetic construct
SEQUENCE: 26
GIHVFILGCF SAGLPKTEAN WVNVISDLKK IEDLIQSMHI DATLYTESDV HPSCKVTAMK        60
CFLLELQVIS LESGDASIHD TVENLIILAN NSLSSNGNVT ESGCKECEEL EEKNIKEFLQ       120
SFVHIVQMFI NTS                                                          133

SEQ ID NO: 27           moltype = AA  length = 22
FEATURE                 Location/Qualifiers
source                  1..22
                        mol_type = protein
                        organism = synthetic construct
SEQUENCE: 27
GPQCTNYALL KLAGDVESNP GP                                                22

SEQ ID NO: 28           moltype = AA  length = 19
```

| FEATURE | Location/Qualifiers |
|---|---|
| source | 1..19<br>mol_type = protein<br>organism = synthetic construct |

SEQUENCE: 28
MEFGLSWLFL VAILKGVQC                                                                 19

| SEQ ID NO: 29 | moltype = AA   length = 452 |
|---|---|
| FEATURE | Location/Qualifiers |
| source | 1..452<br>mol_type = protein<br>organism = synthetic construct |

SEQUENCE: 29
```
QITLRESGGD VVQPGRSLRL SCAASGFTFS SYAIHWVRQA PGKGLEWVAV TWHDGSNKYY  60
AESVMGRFTI SRDNSKNTLY LHMNSLRAED TGVYYCARAK FGEPQYFQHW GQGTLVTVSS 120
GGGGSGGGGS GGGGSDIVMT QSPSFLSASV GDRVTITCRA SQINNYLAW  YQQKPGIAPK 180
LLIYAASTLQ SGVPSRFGGS GSGTEFTLTI SSLQPEDFAT YYCQQLKSYP FTFGPGTKVE 240
IKRAAAIEVM YPPPYLDNEK SNGTIIHVKG KHLCPSPLFP GPSKPKDPKF WVLVVVGGVL 300
ACYSLLVTVA FIIFWVLCAR PRRSPAQEDG KVYINMPGRG RVKFSRSADA PAYQQGQNQL 360
YNELNLGRRE EYDVLDKRRG RDPEMGGKPR RKNPQEGLYN ELQKDKMAEA YSEIGMKGER 420
RRGKGHDGLY QGLSTATKDT YDALHMQALP PR                              452
```

| SEQ ID NO: 30 | moltype = DNA   length = 360 |
|---|---|
| FEATURE | Location/Qualifiers |
| source | 1..360<br>mol_type = other DNA<br>organism = synthetic construct |

SEQUENCE: 30
```
cagatcactt taagggagag cggaggcgat gtggtgcagc ccggtcgttc tttaagactg  60
agctgtgccg ccagcggctt caccttcagc agctacgcca tccactgggt gagacaagct 120
cccggtaaag gtttagagtg ggtggctgtg acttggcacg acggctccaa caagtactat 180
gccgagagcg tgatgggtcg tttcaccatc tctcgtgaca acagcaagaa cactttatat 240
ttacacatga actcttttaag ggccgaggac accggcgtgt actactgcgc cagagccaag 300
ttcggcgagc ccagtacttt ccagcactgg ggccaaggta cactggtgac cgtgtccagc 360
```

| SEQ ID NO: 31 | moltype = DNA   length = 117 |
|---|---|
| FEATURE | Location/Qualifiers |
| source | 1..117<br>mol_type = other DNA<br>organism = synthetic construct |

SEQUENCE: 31
```
atcgaagtta tgtatcctcc tccttaccta gacaatgaga agagcaatgg aaccattatc  60
catgtgaaag ggaaacacct tgtccaagt ccccctatttc ccggaccttc taagccc    117
```

| SEQ ID NO: 32 | moltype = DNA   length = 321 |
|---|---|
| FEATURE | Location/Qualifiers |
| source | 1..321<br>mol_type = other DNA<br>organism = synthetic construct |

SEQUENCE: 32
```
gacatcgtga tgacccagag ccctagcttt ttaagcgcca gcgtgggcga cagagtgacc  60
atcacttgtc gtgccagcca aggtatcaac aactatttag cttggtacca gcagaagccc 120
ggtatcgccc ccaagctgct gatctacgcc gccagcacac tgcagagcgg cgtgcctagc 180
agatttggtg gcagcggctc tggcacagag ttcactttaa ccatcagctc tttacagccc 240
gaggacttcg ccacctacta ctgccagcag ctgaagagct accccttcac cttcggcccc 300
ggcaccaagg tggagatcaa g                                          321
```

| SEQ ID NO: 33 | moltype = DNA   length = 57 |
|---|---|
| FEATURE | Location/Qualifiers |
| source | 1..57<br>mol_type = other DNA<br>organism = synthetic construct |

SEQUENCE: 33
```
atggaattcg ggctgtcctg gctttcttg gtcgcaattc ttaagggcgt ccaatgt      57
```

| SEQ ID NO: 34 | moltype = DNA   length = 57 |
|---|---|
| FEATURE | Location/Qualifiers |
| source | 1..57<br>mol_type = other DNA<br>organism = synthetic construct |

SEQUENCE: 34
```
atggagttcg gcctgagctg gctgttcctg gtggccatcc tgaagggcgt gcagtgc      57
```

| SEQ ID NO: 35 | moltype = DNA   length = 725 |
|---|---|
| FEATURE | Location/Qualifiers |
| source | 1..725<br>mol_type = other DNA<br>organism = synthetic construct |

SEQUENCE: 35

```
agataactct gcgcgagtca ggaggagacg tggtgcaacc gggcagatct ctcaggcttt    60
catgtgccgc cagtggcttc acatttagct cttatgcaat acattgggtc aggcaggctc   120
ctggcaaggg cttggaatgg gtagcggtta cctggcatga tggatctaac aaatactacg   180
ccgagtctgt tatgggtcga ttcacaattt ctcgagacaa ttcaaaaaac acactctacc   240
tgcatatgaa ctcacttaga gcagagaca ctggtgtca ttactgcgcc agagcaaaat    300
tcggcgagcc acagtatttc cagcactggg gacaaggaac cctcgtaaca gtatctagtg   360
ggggcggagg gtctggagga ggggggagcg gggggaggcg gctctgatatt gttatgaccc   420
aatcaccatc ttttctgagc gctagtgtcg gcgacagggt tacaatcaca tgccgagcaa   480
gccaaggaat caacaattat ctcgcaatggt atcaacaaaa accaggtatc gccccgaaac   540
ttcttattta cgcagcatca accctgcaaa gcggagttcc ttctagattt ggtggcagcg   600
gctccgggac tgaattcact cttactatttt cctcccttca acccgaagat ttcgccacat   660
attactgcca gcagcttaag tcatacccct tcacttttgg cccaggaact aaagttgaaa   720
tcaaa                                                               725

SEQ ID NO: 36          moltype = DNA  length = 726
FEATURE                Location/Qualifiers
source                 1..726
                       mol_type = other DNA
                       organism = synthetic construct
SEQUENCE: 36
cagatcactt taagggagag cggaggcgat gtggtgcagc ccggtcgttc tttaagactg    60
agctgtgccg ccagcggctt caccttcagc agctacgtca tccactggtg gagacaagct   120
cccggtaaag gtttagagtg ggtggctgtg acttggcacg acggctccaa caagtactat   180
gccgagagcg tgatgggtcg tttcaccatc tctcgtgaca cagcaagaa cactttatat   240
ttacacatga actcttaag ggccgaggac accggcgtgt actactgcgc cagagccaag   300
tcggcgagc cccagtactt ccagcactgg ggccaaggta cactggtgac cgtgtccagc   360
ggggcggag gtctggagg agggggagc ggggaggcg gctctgacat cgtgatgacc   420
cagagcccta gcttttttaag cgccagcgtg ggcgacagag tgaccatcac ttgtcgtgcc   480
agccaaggta tcaacaacta tttagcttgg taccagcaga agcccggtat cgcccccaag   540
ctgctgatct acgccgccag cacactgcag agcggcgtgc ctagcagatt tggtggcagc   600
ggctctggca cagagttcac tttaaccatc agctctttac agcccgagga cttcgccacc   660
tactactgcc agcagctgaa gagctacccc ttcaccttcg gccccggcac caaggtggag   720
atcaag                                                              726

SEQ ID NO: 37          moltype = DNA  length = 141
FEATURE                Location/Qualifiers
source                 1..141
                       mol_type = other DNA
                       organism = synthetic construct
SEQUENCE: 37
cgggcggccg caattgaagt tatgtatcct cctccttacc tagacaatga gaagagcaat    60
ggaaccatta tccatgtgaa agggaaacac ctttgtccaa gtccctatt tcccggacct   120
tctaagccca aagatcccaa a                                             141

SEQ ID NO: 38          moltype = DNA  length = 81
FEATURE                Location/Qualifiers
source                 1..81
                       mol_type = other DNA
                       organism = synthetic construct
SEQUENCE: 38
ttttgggtgc tggtggtggt tggtggagtc ctggcttgct atagcttgct agtaacagtg    60
gcctttatta ttttctgggt g                                             81

SEQ ID NO: 39          moltype = DNA  length = 72
FEATURE                Location/Qualifiers
source                 1..72
                       mol_type = other DNA
                       organism = synthetic construct
SEQUENCE: 39
ctttgcgcac gcccacgccg cagccccgcc caagaagatg gcaaagtcta catcaacatg    60
ccaggcaggg gc                                                       72

SEQ ID NO: 40          moltype = DNA  length = 336
FEATURE                Location/Qualifiers
source                 1..336
                       mol_type = other DNA
                       organism = synthetic construct
SEQUENCE: 40
cgcgtgaagt tcagcaggag cgcagacgcc ccgcgtacc agcagggcca gaaccagctc    60
tataacgagc tcaatctagg acgaagagag gagtacgatg tttggacaa agacgtggc   120
cgggaccctg agatggggggg aaagccgaga aggaagaacc ctcaggaagg cctgtacaat   180
gaactgcaga aagataagat ggcggaggcc tacagtgaga tgggatgaa aggcgagcgc   240
cggaggggca gggggcacga tggcctttac cagggtctca gtacagccac caaggacacc   300
tacgacgccc ttcacatgca ggccctgccc cctcgc                             336

SEQ ID NO: 41          moltype = DNA  length = 123
FEATURE                Location/Qualifiers
source                 1..123
                       mol_type = other DNA
```

```
                    organism = synthetic construct
SEQUENCE: 41
aggagtaaga ggagcaggct cctgcacagt gactacatga acatgactcc ccgccgcccc    60
gggcccaccc gcaagcatta ccagccctat gccccaccac gcgacttcgc agcctatcgc   120
tca                                                                 123

SEQ ID NO: 42           moltype = DNA   length = 66
FEATURE                 Location/Qualifiers
source                  1..66
                        mol_type = other DNA
                        organism = synthetic construct
SEQUENCE: 42
ggaccgcagt gtactaatta tgctctcttg aaattggctg agatgttga gagcaatccc     60
gggccc                                                               66

SEQ ID NO: 43           moltype = DNA   length = 66
FEATURE                 Location/Qualifiers
source                  1..66
                        mol_type = other DNA
                        organism = synthetic construct
SEQUENCE: 43
ggccctcagt gcaccaacta cgccctgctc aagctggctg gcgacgtcga gagcaacccc    60
ggaccc                                                               66

SEQ ID NO: 44           moltype = DNA   length = 1356
FEATURE                 Location/Qualifiers
source                  1..1356
                        mol_type = other DNA
                        organism = synthetic construct
SEQUENCE: 44
cagataactc tgcgcgagtc aggaggagac gtggtgcaac cggcagatc tctcaggctt     60
tcatgtgccg ccagtggctt cacatttagc tcttatgcaa tacattgggt caggcaggct   120
cctggcaagg gcttggaatg ggtagcggtt acctggcatg atggatctaa caaatactac   180
gccgagtctg ttatgggtcg attcacaatt tctcgagaca attcaaaaaa cacactctac   240
ctgcatatga actcacttag agcagaggac actggtgtct attactgcgc cagagcaaaa   300
ttcggcgagc cacagtattt ccagcactgg ggacaaggaa ccctcgtaac agtatccagt   360
gggggcggag gtctggagg aggggggagc ggggaggcg gctctgatat tgttatgacc     420
caatcaccat cttttctgag cgctagtgtc ggcgacaggg ttacaatcac atgccgagca   480
agcaaggaa tcaacaatta tctcgcatgg tatcaacaaa aaccaggtat cgccccgaaa    540
cttcttattt acgcagcatc aaccctgcaa agcggagttc cttctagatt tggtggcagc   600
ggctccggga ctgaattcac tcttactatt tcctcccttc aacccgaaga tttcgccaca   660
tattactgcc agcagcttaa gtcatacccc ttcactttg gcccaggaac taagttgaa    720
atcaaacggc cggccgcaat tgaagttatg tatcctcctc cttacctaga caatgagaag   780
agcaatggaa ccattatcca tgtgaaaggg aaacacctttg tccaagtcc ctatttccc    840
ggaccttcta gcccaaagat cccaaatttt ggggtgctgg tggtggttgg tggagtcctg   900
gcttgctata gcttgctagt aacagtggcc tttattattt tctgggtgct ttgcgcacgc   960
ccacgccgca gcccccccca agaagatggc aaagtctaca tcaacatgcc aggcaggggc  1020
cgcgtgaagt tcagcaggag cgcagacgcc cccgcgtacc agcagggcca gaaccagctc  1080
tataacgagc tcaatctagg acgaagagag gagtacgatg ttttggacaa aagacgtggc  1140
cgggaccctg agatggggg aaagccgaga aggaagaacc ctcaggaagg cctgtacaat  1200
gaactgcaga aagataagat ggcggaggcc tacagtgaga ttgggatgaa aggcgagcgc  1260
cggagggca aggggcacga tggcctttac caggtctca gtacagccac caaggacacc    1320
tacgacgccc ttcacatgca ggccctgccc cctcgc                           1356

SEQ ID NO: 45           moltype = AA   length = 672
FEATURE                 Location/Qualifiers
source                  1..672
                        mol_type = protein
                        organism = synthetic construct
SEQUENCE: 45
MEFGLSWLFL VAILKGVQCQ ITLRESGGDV VQPGRSLRLS CAASGFTFSS YAIHWVRQAP    60
GKGLEWVAVT WHDGSNKYYA ESVMGRFTIS RDNSKNTLYL HMNSLRAEDT GVYYCARAKF   120
GEPQYFQHWG QGTLVTVSSG GGGSGGGGSG GGGSDIVMTQ SPSFLSASVG DRVTITCRAS   180
QGINNYLAWY QQKPGIAPKL LIYAASTLQS GVPSRFGGSG SGTEFTLTIS SLQPEDFATY   240
YCQQLKSYPF TFGPGTKVEI KRAAAIEVMY PPPYLDNEKS NGTIIHVGK HLCPSPLFPG    300
PSKPKPDKFW VLVVVGGVLA CYSLLVTVAF IIFWVRSKRS RLLHSDYMNM TPRRPGPTRK   360
HYQPYAPPRD FAAYRSRVKF SRSADAPAYQ QGQNQLYNEL NLGRREEYDV LDKRRGRDPE   420
MGGKPRRKNP QEGLYNELQK DKMAEAYSEI GMKGERRRGK GHDGLYQGLS TATKDTYDAL   480
HMQALPPRGP QCTNYALLKL AGDVESNPGP MRISKPHLRS ISIQCYLCLL LNSHFLTEAG   540
IHVFILGCFS AGLPKTEANW VNVISDLKKI EDLIQSMHID ATLYTESDVH PSCKVTAMKC   600
FLLELQVISL ESGDASIHDT VENLIILANN SLSSNGNVTE SGCKECEELE EKNIKEFLQS   660
FVHIVQMFIN TS                                                      672

SEQ ID NO: 46           moltype = DNA   length = 2019
FEATURE                 Location/Qualifiers
source                  1..2019
                        mol_type = other DNA
                        organism = synthetic construct
SEQUENCE: 46
```

```
atggaattcg ggctgtcctg gcttttcttg gtcgcaattc ttaagggcgt ccaatgtcag    60
ataactctgc gcgagtcagg aggagacgtg gtgcaaccgg gcagatctct caggctttca   120
tgtgccgcca gtggcttcac atttagctct tatgcaatac attgggtcag gcaggctcct   180
ggcaagggct tggaatgggt agcggttacc tggcatgatg gatctaacaa atactacgcc   240
gagtctgtta tgggtcgatt cacaaatttct cgagacaatt caaaaaacac actctacctg   300
catatgaact cacttagagc agaggacact ggtgtctatt actgcgccag agcaaaattc   360
ggcgagccac agtatttcca gcactgggga caaggaaccc tcgtaacagt atctagtggg   420
ggcggagggt ctgaggagg ggggagcggg ggaggcggct ctgatattgt tatgacccaa   480
tcaccatctt ttctgagcgc tagtgtcggc gacagggtta caatcacatg ccgagcaagc   540
caaggaatca acaattatct cgcatggtat caacaaaaac caggtatcgc cccgaaactt   600
cttatttacg cagcatcaac cctgcaaagc ggagttcctt ctagatttgg tggcagcggc   660
tccgggactg aattcactct tactatttcc tcccttcaac ccgaagattt cgccacatat   720
tactgccagc agcttaagtc ataccccttc acttttggcc aggaactaaa agttgaaatc   780
aaacgggcgg ccgcaattga agttatgtat cctcctcctt acctagacaa tgagaagagc   840
aatggaacca ttatccatgt gaaagggaaa caccctttgtc caagtcccct atttcccgga   900
ccttctaagc ccaaagatcc caaattttgg gtgctggtgg tggttggtgg agtcctggct   960
tgctatagct tgctagtaac agtggccttt attatttct gggtgaggag taagaggagc  1020
aggctcctgc acagtgacta catgaacatg actccccgcc gccccgggcc caccgcaag  1080
cattaccagc cctatgcccc accacgcgac ttcgcagcct atcgctcacg cgtgaagttc  1140
agcaggagcg cagacgcccc cgcgtaccag cagggccaga accagctcta taacgagctc  1200
aatctaggac gaagagagga gtacgatgtt ttggacaaaa gacgtggccg ggaccctgag  1260
atggggggaa agccgagaag gaagaaccct caggaaggcc tgtacaatga actgcagaaa  1320
gataagatgg cggaggccta cagtgagatt gggatgaaag gcgagcgccg gaggggcaag  1380
gggcacgatg gcctttacca gggtctcagt acagccacca aggacaccta cgacgccctt  1440
cacatgcagg ccctgccccc tcgcggaccg cagtgtacta attatgctct cttgaaattg  1500
gctggagatg ttgagagcaa tcccgggccc atgcgcatta gcaagcccca cctgccgagc  1560
atcagcatcc agtgctacct gtgcctgctg ctgaacagcc acttcctgac cgaggccggc  1620
atccacgtgt tcatcctggg ctgcttcagc gccggactgc ccaagaccga ggccaactgg  1680
gtgaacgtga tcagcgacct gaagaagatc gaggacctga tccagagcat gcacatcgac  1740
gccaccctgt acaccgagag cgacgtgcac cccagctgca aggtgaccgc catgaagtgc  1800
tttctgctgg aactgcaggt gatcagcctg gaaagcggcg acgccagcat ccacgacacc  1860
gtggagaacc tgatcatcct ggccaacaac agcctgagcg caacggcaa cgtgaccgag  1920
agcggctgca aagagtgcga ggaactggaa gagaagaaca tcaaagagtt tctgcagagc  1980
ttcgtgcaca tcgtgcagat gttcatcaac accagctga                         2019

SEQ ID NO: 47          moltype = DNA   length = 360
FEATURE                Location/Qualifiers
source                 1..360
                       mol_type = other DNA
                       organism = synthetic construct
SEQUENCE: 47
cagataactc tgcgcgagtc aggaggagac gtggtgcaac cgggcagatc tctcaggctt    60
tcatgtgccg ccagtggctt cacatttagc tcttatgcaa tacattgggt caggcaggct   120
cctggcaagg gcttggaatg ggtagcggtt acctggcatg atggatctaa caaatactac   180
gccgagtctg ttatgggtcg attcacaatt tctcgagaca attcaaaaaa cacactctac   240
ctgcatatga actcacttag cagaggacac tggtgtctat tactgcgcgc agagcaaaaa   300
ttcggcgagc cacagtattt ccagcactgg ggacaaggaa ccctcgtaac agtatctagt   360

SEQ ID NO: 48          moltype = DNA   length = 360
FEATURE                Location/Qualifiers
source                 1..360
                       mol_type = other DNA
                       organism = synthetic construct
SEQUENCE: 48
cagatcaccc tgagggagtc tggaggcgac gtggtgcagc ctggaaggag cctgagactg    60
agctgcgccg cctctggatt caccttcagc agctacgcca tccactgggt caggcaggct   120
cctggcaagg gactggagtg ggtggccgtt acctggcacg acggcagcaa caagtactac   180
gccgagagcg ttatgggcag gttcaccatc agcagggaca cagcaagaa cacccctgtac   240
ctgcacatga actctctgag ggccgaggac acaggcgtgt actactgcgc cagggccaag   300
ttcggtgagc ccagtactt ccagcactgg ggccagggaa ccctggtgac cgtgtcttct   360

SEQ ID NO: 49          moltype = DNA   length = 321
FEATURE                Location/Qualifiers
source                 1..321
                       mol_type = other DNA
                       organism = synthetic construct
SEQUENCE: 49
gatattgtta tgacccaatc accatctttt ctgagcgcta gtgtcggcga cagggttaca    60
atcacatgcc gagcaagcca aggaatcaac aattatctcg catggtatca acaaaaacca   120
ggtatcgccc cgaaacttct tatttacgca gcatcaaccc tgcaaagcgg agttccttct   180
agatttggtg gcagcggctc cgggactgaa ttcactctta ctatttcctc ccttcaaccc   240
gaagatttcg ccacatatta ctgccagcag cttaagtcat accccttcac ttttggccca   300
ggaactaaag ttgaaatcaa a                                             321

SEQ ID NO: 50          moltype = DNA   length = 321
FEATURE                Location/Qualifiers
source                 1..321
                       mol_type = other DNA
                       organism = synthetic construct
```

```
SEQUENCE: 50
gacatcgtga tgacccagag ccctagcttc ctgtctgcca gcgtgggaga cagggtgacc    60
atcacctgca gagccagcca gggcatcaat aactacctgg cctggtacca gcagaagccc   120
ggcattgccc ccaagctcct gatctacgcc gccagcaccc tgcaaagcgg cgtgccctca   180
aggttcggcg gatctggaag cggcaccgag ttcaccctga ccattagcag cctgcagccc   240
gaggacttcg ccacctacta ctgccagcag ctgaagagct accccttcac cttcggccct   300
ggcaccaagg tggagatcaa g                                              321

SEQ ID NO: 51           moltype = DNA  length = 726
FEATURE                 Location/Qualifiers
source                  1..726
                        mol_type = other DNA
                        organism = synthetic construct
SEQUENCE: 51
cagatcaccc tgagggagtc tggaggcgac gtggtgcagc ctggaaggag cctgagactg    60
agctgcgccg cctctggatt caccttcagc agctacgcca tccactgggt caggcaggct   120
cctggcaagg gactggagtg ggtggccgtt acctggcacg acggcagcaa caagtactac   180
gccgagagcg ttatgggcag gttcaccatc agcagggaca acagcaagaa cacccctgtac  240
ctgcacatga actctctgag ggccgaggac acaggcgtgt actactgcgc cagggccaag   300
ttcggtgagc ccagtacttc cagcactggg gccagggaaa ccctggtgac cgtgtcttct   360
ggcggagggg gatctggagg aggaggaagt ggaggcggtg gcagcgacat cgtgatgacc   420
cagagcccta gcttcctgtc tgccagcgtg ggagacagag tgaccatcac ctgcagagcc   480
agccagggca tcaataacta cctggcctgg taccagcaga agcccggcat tgcccccaag   540
ctcctgatct acgccgccag caccctgcaa agcggcgtgc cctctaggtt cggcggatct   600
ggaagcggca ccgagttcac cctgaccatt agcagcctgc agcccgagga cttcgccacc   660
tactactgcc agcagctgaa gagctacccc ttcaccttcg gccctggcac caaggtggag   720
atcaag                                                               726

SEQ ID NO: 52           moltype = DNA  length = 486
FEATURE                 Location/Qualifiers
source                  1..486
                        mol_type = other DNA
                        organism = synthetic construct
SEQUENCE: 52
atgcgcatta gcaagcccca cctgcggagc atcagcatcc agtgctacct gtgcctgctg    60
ctgaacagcc acttcctgac cgaggccggc atccacgtgt tcatcctggg gctgcttcagc  120
gccggactgc ccaagaccga ggccaactgg gtgaacgtga tcagcgacct gaagaagatc   180
gaggacctga tccagagcat gcacatcgac gccacccctgt acaccgagag cgacgtgcac  240
cccagctgca aggtgaccgc catgaagtgc tttctgctga aactgcaggt gatcagcctg   300
gaaagcggcg acgccagcat ccacgacacc gtggagaacc tgatcatcct ggccaacaac   360
agcctgagca gcaacggcaa cgtgaccgag agcggctgca aagagtgcga ggaactggaa   420
gagaagaaca tcaaagagtt tctgcagagc ttcgtgcaca tcgtgcagat gttcatcaac   480
accagc                                                               486

SEQ ID NO: 53           moltype = DNA  length = 486
FEATURE                 Location/Qualifiers
source                  1..486
                        mol_type = other DNA
                        organism = synthetic construct
SEQUENCE: 53
atgaggatca gcaagcctca cctgaggagc attagcatcc agtgctacct gtgcctgctc    60
ctgaactccc acttcctgac cgaggccggc atccacgtct catcctggg ctgcttcagc   120
gctggcctgc ccaaaaccga ggccaactgg gtgaacgtga tcagcgacct caagaagatc   180
gaggacctga tccagagcat gcacatcgac gccacccctgt ataccgagag cgacgtgcac  240
cccagctgca aggtgaccgc catgaagtgc ttcctgctga gctgcaggt catcagcctg   300
gagagcggcg atgccagcat ccacgacacc gtggagaacc tgatcatcct ggccaacaac   360
agcctgagca gcaacgggaa cgtgaccgag tccggctgca aggagtgcga ggagctggag   420
gagaagaaca tcaaggagtt cctgcagtcc ttcgtgcaca tcgtgcagat gttcatcaac   480
accagc                                                               486

SEQ ID NO: 54           moltype = DNA  length = 141
FEATURE                 Location/Qualifiers
source                  1..141
                        mol_type = other DNA
                        organism = synthetic construct
SEQUENCE: 54
agggccgccg ccattgaggt gatgtacccc cccccctacc tggacaacga aaagagcaac    60
ggcaccatca tccacgtgaa gggcaagcac ctctgcccta gccccctgtt ccctggaccc   120
agcaagccca aggaccccaa g                                              141

SEQ ID NO: 55           moltype = DNA  length = 1968
FEATURE                 Location/Qualifiers
source                  1..1968
                        mol_type = other DNA
                        organism = synthetic construct
SEQUENCE: 55
atggaattcg gctgtcctg gcttttcttg gtcgcaattc ttaagggcgt ccaatgtcag    60
ataactctgc gcgagtcagg aggagacgtg gtgcaaccgg gcagatctct caggctttca   120
tgtgccgcca gtggcttcac atttagctct tatgcaatac attgggtcag gcaggctcct  180
```

```
ggcaagggct tggaatgggt agcggttacc tggcatgatg gatctaacaa atactacgcc   240
gagtctgtta tgggtcgatt cacaatttct cgagacaatt caaaaaacac actctacctg   300
catatgaact cacttagagc agaggacact ggtgtctatt actgcgccag agcaaaattc   360
ggcgagccac agtatttcca gcactgggga caaggaaccc tcgtaacagt atctagtggg   420
ggcgagggt ctggaggagg ggggagcggg ggaggcgct ctgatattgt tatgacccaa   480
tcaccatctt ttctgagcgc tagtgtcggc gacagggtta caatcacatg ccgagcaagc   540
caaggaatca acaattatct cgcatggtat aacaaaaac caggtatcgc cccgaaactt   600
cttatttacg cagcatcaac cctgcaaagc ggagttcctt ctagatttgg tggcagcggg   660
tccgggactg aattcactct tactatttcc tcccttcaac ccgaagattt cgccacatat   720
tactgccagc agcttaagtc ataccccttc acttttggcc caggaactaa agttgaaatc   780
aaacgggcgg ccgcaattga agttatgtat cctcctcctt acctagacaa tgagaagagc   840
aatgaaacca ttatccatgt gaagggaaa caccttgtc caagtcccct atttcccgga   900
ccttctaagc caaagatcc caatttggg gtgctggtgg tggttggtgg agtcctggct   960
tgctatagct tgctagtaac agtggccttt attattttct ggtgctttg cgcacgccca  1020
cgccgcagcc ccgccaaga gatggcaaa gtctacatca acatgccagg caggggccga  1080
gtgaagttca gcaggagcgc agacgccccc cgctaccagc agggccagaa ccagctctat  1140
aacgagctca atctaggacg aagagaggag tacgatgttt tggacaaaag acgtggccgg  1200
gaccctgaga tgggggaaa gccgagaagg aagaaccctc aggaaggcct gtacaatgaa  1260
ctgcagaaag ataagatggc ggaggcctac agtgagattg ggatgaaagg cgagcgccgg  1320
aggggcaagg ggcacgatgg cctttaccag ggtctcagta cagccaccaa ggacacctac  1380
gacgccttc acatgcaggc cctgcccct cgcggaccgc agtgtactaa ttatgctctc  1440
ttgaaattgg ctggagatgt tgagacaat cccggccca gtcgcattag caagcccac  1500
ctgcggagca tcagcatcca gtgctacctg tgcctgctgc tgaacagcca cttcctgacc  1560
gaggccggca tccacgtgtt catcctgggc tgcttcagcg ccggactgcc caagaccgag  1620
gccaactggg tgaacgtgat cagcgacctg aagaagatcg aggacctgat ccagagcatg  1680
cacatcgacg ccaccctgta caccgagagc gacgtgcacc ccagctgcaa ggtgaccgcc  1740
atgaagtgct ttctgctgga actgcaggtg atcagcctgg aaagcggcga cgccagcatc  1800
cacgacaccg tggagaacct gatcatcctg ccaacaaca gcctgagcag caacggcaac  1860
gtgaccgaga gcggctgcaa agagtgcgag gaactggaag agaagaacat caaagagttt  1920
ctgcagagct tcgtgcacat cgtgcagatg ttcatcaaca ccagctga             1968

SEQ ID NO: 56           moltype = DNA   length = 81
FEATURE                 Location/Qualifiers
source                  1..81
                        mol_type = other DNA
                        organism = synthetic construct
SEQUENCE: 56
ttctgggtgc tggtcgtggt gggaggcgtt ctggcctgct acagcctgct ggtgacagtg   60
gcctttatca tcttctgggt c                                            81

SEQ ID NO: 57           moltype = DNA   length = 72
FEATURE                 Location/Qualifiers
source                  1..72
                        mol_type = other DNA
                        organism = synthetic construct
SEQUENCE: 57
ctgtgcgcca gacctaggag aagccccgcc caggaagacg gaaaggtcta catcaacatg   60
cccggaaggg ga                                                      72

SEQ ID NO: 58           moltype = DNA   length = 336
FEATURE                 Location/Qualifiers
source                  1..336
                        mol_type = other DNA
                        organism = synthetic construct
SEQUENCE: 58
agggtcaagt tcagccggtc tgctgatgct cccgcctacc agcaaggcca aaaccagctg   60
tacaacgagc tgaacctggg caggagagaa gagtacgacg tgctggacaa gaggagaggc  120
agggaccccg agatgggagg caagcccaga aggaagaacc cccaggaggg cctgtacaat  180
gagctgcaga aggacaagat ggccgaggcc tacagcgaga tcggcatgaa gggcgagaga  240
agaaggggca agggccacga cggattgtac caggcctga gcaccgctac caaggacacc  300
tacgacgccc tgcatatgca agctctgcct cctagg                            336

SEQ ID NO: 59           moltype = AA    length = 29
FEATURE                 Location/Qualifiers
source                  1..29
                        mol_type = protein
                        organism = synthetic construct
SEQUENCE: 59
MRISKPHLRS ISIQCYLCLL LNSHFLTEA                                     29

SEQ ID NO: 60           moltype = DNA   length = 1356
FEATURE                 Location/Qualifiers
source                  1..1356
                        mol_type = other DNA
                        organism = synthetic construct
SEQUENCE: 60
cagatcaccc tgagggagtc tggaggcgac gtggtgcagc ctggaaggag cctgagactg   60
agctgcgccg cctctggatt caccttcagc agctacgcca tccactgggt caggcaggct  120
cctggcaagg gactggagtg ggtggccgtt acctggcacg acggcagcaa caagtactac  180
```

-continued

```
gccgagagcg ttatgggcag gttcaccatc agcagggaca acagcaagaa caccctgtac   240
ctgcacatga actctctgag ggccgaggac acaggcgtgt actactgcgc cagggccaag   300
ttcggtgagc cccagtactt ccagcactgg ggccagggaa ccctggtgac cgtgtcttct   360
ggcggagggg gatctggagg aggaggaagt ggaggcggtg gcagcgacat cgtgatgacc   420
cagagcccta gcttcctgtc tgccagcgtg ggagacaggg tgaccatcac ctgcagagcc   480
agccagggca tcaataacta cctggcctgg taccagcaga gcccggcat tgcccccaag    540
ctcctgatct acgccgccag caccctgcaa agcggcgtgc cctctaggtt cggcggatct   600
ggaagcggca ccgagttcac cctgaccatt agcagcctgc agcccgagga cttcgccacc   660
tactactgcc agcagctgaa gagctacccc ttcaccttcg ccctggcac caaggtggag    720
atcaagaggg ccgccgccat tgaggtgatg taccccccc cctacctgga caacgagaag    780
agcaacggca ccatcatcca cgtgaagggc aagcacctct gccctagccc cctgttccct   840
ggacccagca agcccaagga ccccaagttc tgggtgctgg tcgtggtggg aggcgttctg   900
gcctgctaca gcctgctggt gacagtggcc tttatcatct tctgggtcct gtgcgccaga   960
cctaggagaa gccccgccca ggaagacgga aaggtctaca tcaacatgcc cggaaggga   1020
agggtcaagt tcagccggtc tgctgatgct cccgcctacc agcaaggcca aaaccagctg   1080
tacaacgagc tgaacctggg caggagagaa gagtacgacg tgctggacaa gaggagaggc   1140
agggaccccg agatgggagg caagcccaga aggaagaacc ccaggaggg cctgtacaat   1200
gagctgcaga aggacaagat ggccgaggcc tacagcgaga tcggcatgaa gggcgagaga   1260
agaaggggca agggccacga cggattgtac cagggcctga gcaccgctac caaggacacc   1320
tacgacgccc tgcatatgca agctctgcct cctagg                            1356
```

```
SEQ ID NO: 61          moltype = AA   length = 39
FEATURE                Location/Qualifiers
source                 1..39
                       mol_type = protein
                       organism = synthetic construct
SEQUENCE: 61
IEVMYPPPYL DNEKSNGTII HVKGKHLCPS PLFPGPSKP                           39

SEQ ID NO: 62          moltype = DNA   length = 117
FEATURE                Location/Qualifiers
source                 1..117
                       mol_type = other DNA
                       organism = synthetic construct
SEQUENCE: 62
attgaagtta tgtatcctcc tccttaccta gacaatgaga agagcaatgg aaccattatc    60
catgtgaaag ggaaacacct ttgtccaagt cccctatttc ccggaccttc taagccc     117

SEQ ID NO: 63          moltype = DNA   length = 117
FEATURE                Location/Qualifiers
source                 1..117
                       mol_type = other DNA
                       organism = synthetic construct
SEQUENCE: 63
attgaggtga tgtacccccc ccctacctg gacaacgaga agagcaacgg caccatcatc     60
cacgtgaagg gcaagcacct ctgccctagc cccctgttcc ctggacccag caagccc     117

SEQ ID NO: 64          moltype = AA   length = 41
FEATURE                Location/Qualifiers
source                 1..41
                       mol_type = protein
                       organism = synthetic construct
SEQUENCE: 64
RSKRSRLLHS DYMNMTPRRP GPTRKHYQPY APPRDFAAYR S                        41

SEQ ID NO: 65          moltype = AA   length = 5
FEATURE                Location/Qualifiers
source                 1..5
                       mol_type = protein
                       organism = synthetic construct
REPEAT                 1..5
                       note = GGGGS can be repeated n times where n is an integer
                        of at least 1, 2, 3, 4, 5, 6, 7, 8, 9, or 10.
SEQUENCE: 65
GGGGS                                                                 5
```

The invention claimed is:

1. A chimeric antigen receptor (CAR) comprising an anti-B-cell maturation antigen antibody or antigen binding fragment thereof, a hinge domain, a transmembrane domain, a DAP10 costimulatory domain, and at least one intracellular signaling domain, wherein the CAR comprises the amino acid sequence of SEQ ID NOs: 13 or 29.

2. A polynucleotide encoding a chimeric antigen receptor (CAR) comprising an anti-B-cell maturation antigen antibody or antigen binding fragment thereof, a hinge domain, a transmembrane domain, a DAP10 costimulatory domain, and at least one intracellular signaling domain, wherein the polynucleotide comprises the nucleic acid sequence of SEQ ID NO: 25.

3. A polynucleotide encoding a chimeric antigen receptor (CAR) comprising an anti-B-cell maturation antigen antibody or antigen binding fragment thereof, a hinge domain, a transmembrane domain, a DAP10 costimulatory domain, and at least one intracellular signaling domain, wherein the polynucleotide comprises the nucleic acid sequence of SEQ ID NO: 60.

* * * * *